United States Patent
Davoodi et al.

(10) Patent No.: US 9,563,203 B2
(45) Date of Patent: Feb. 7, 2017

(54) CONTROLLABLE BUOYS AND NETWORKED BUOY SYSTEMS

(71) Applicant: CALIFORNIA INSTITUTE OF TECHNOLOGY, Pasadena, CA (US)

(72) Inventors: Faranak Davoodi, San Marino, CA (US); Farhooman Davoudi, Roissy-en-Brie (FR)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/729,011

(22) Filed: Jun. 2, 2015

(65) Prior Publication Data

US 2015/0346726 A1 Dec. 3, 2015

Related U.S. Application Data

(60) Provisional application No. 62/006,698, filed on Jun. 2, 2014, provisional application No. 62/153,322, filed on Apr. 27, 2015.

(51) Int. Cl.
| | |
|---|---|
| *G05D 1/00* | (2006.01) |
| *G05D 1/02* | (2006.01) |
| *B63B 22/24* | (2006.01) |
| *B63B 22/22* | (2006.01) |
| *B63B 22/20* | (2006.01) |
| *B63G 8/00* | (2006.01) |
| *B63B 22/02* | (2006.01) |
| *B63B 22/00* | (2006.01) |

(52) U.S. Cl.
CPC ............. *G05D 1/0088* (2013.01); *B63B 22/02* (2013.01); *B63B 22/20* (2013.01); *B63B 22/22* (2013.01); *B63B 22/24* (2013.01); *B63G 8/001* (2013.01); *G05D 1/0206* (2013.01); *B63B 2022/006* (2013.01); *B63B 2203/00* (2013.01); *B63B 2213/02* (2013.01); *B63G 2008/007* (2013.01); *Y02E 10/38* (2013.01)

(58) Field of Classification Search
CPC ..... G05D 1/0088; G05D 1/0206; E21B 7/008; E21B 7/14; E21B 7/146
USPC ........................................................ 701/21
See application file for complete search history.

(56) References Cited

U.S. PATENT DOCUMENTS

| 819,609 | A | 5/1906 | Shorthouse |
|---|---|---|---|
| 1,263,262 | A | 4/1918 | McFaul |

(Continued)

FOREIGN PATENT DOCUMENTS

EP    2207013    12/2010

OTHER PUBLICATIONS

Kenyon, K. E. (1969), Stokes drift for random gravity waves, J. Geophys. Res., 74(28), 6991-6994, doi:10.1029/JC074i028p06991.

(Continued)

*Primary Examiner* — John Q Nguyen
*Assistant Examiner* — Anshul Sood
(74) *Attorney, Agent, or Firm* — Steinfl & Bruno, LLP

(57) ABSTRACT

Buoyant sensor networks are described, comprising floating buoys with sensors and energy harvesting capabilities. The buoys can control their buoyancy and motion, and can organize communication in a distributed fashion. Some buoys may have tethered underwater vehicles with a smart spooling system that allows the vehicles to dive deep underwater while remaining in communication and connection with the buoys.

28 Claims, 25 Drawing Sheets

(56) References Cited

U.S. PATENT DOCUMENTS

| | | | |
|---|---|---|---|
| 2,949,696 A | | 8/1960 | Easterling |
| 3,798,835 A | | 3/1974 | McKeehan |
| 4,541,814 A | | 9/1985 | Martin |
| 5,060,206 A | * | 10/1991 | DeMetz, Sr. .......... G10K 11/04 367/136 |
| 5,593,332 A | | 1/1997 | Green |
| 6,289,263 B1 | | 9/2001 | Mukherjee |
| 6,679,118 B1 | | 1/2004 | Esashi et al. |
| 7,371,136 B2 | | 5/2008 | Hine et al. |
| 7,641,524 B2 | | 1/2010 | Hine et al. |
| 8,043,133 B2 | | 10/2011 | Hine et al. |
| 8,054,198 B2 | | 11/2011 | Spinelli et al. |
| 8,287,323 B2 | | 10/2012 | Hine et al. |
| 8,316,970 B1 | | 11/2012 | Tran |
| 8,912,892 B2 | | 12/2014 | Davoodi et al. |
| 2003/0055359 A1 | | 3/2003 | Halleck et al. |
| 2005/0200481 A1 | | 9/2005 | Wallach |
| 2009/0127861 A1 | * | 5/2009 | Sankrithi .............. F03B 13/264 290/54 |
| 2009/0299501 A1 | * | 12/2009 | Lankinen ............... A01K 91/08 700/56 |
| 2010/0066809 A1 | | 3/2010 | Cormack et al. |
| 2010/0212574 A1 | | 8/2010 | Hawkes et al. |
| 2010/0274488 A1 | | 10/2010 | Kenney et al. |
| 2011/0011323 A1 | | 1/2011 | Wiggins et al. |
| 2011/0066239 A1 | * | 3/2011 | Smoot ..................... A61F 2/141 623/6.64 |
| 2011/0115223 A1 | * | 5/2011 | Stahlkopf ............... F01K 13/02 290/7 |
| 2012/0174571 A1 | * | 7/2012 | Villanueva ............. F03G 7/065 60/527 |
| 2012/0244815 A1 | | 9/2012 | Altan et al. |
| 2012/0285544 A1 | | 11/2012 | Westby et al. |
| 2012/0289103 A1 | | 11/2012 | Hudson et al. |
| 2013/0222115 A1 | | 8/2013 | Davoodi et al. |
| 2014/0110252 A1 | * | 4/2014 | Cooper .................... C25B 9/00 204/275.1 |

OTHER PUBLICATIONS

Burkhardt, M. et al. "Energy Harvesting for Moball, A Self-Propelled Mobile Sensor Platform Capable of Long Duration Operation in Harsh Terrains" IEEE Int. Conf. Robotics and Automation, May-Jun. 2014, Hong Kong. p. 2665-2672.

Ramezani, H. et al. "Underwater Acoustic Localization Based on Collision Tolerant Packet Scheduling", IEEE Trans. Wireless Commun., May 2014. vol. 14; No. 5. 2584-2595.

L. Freitag et al. "Basin-Scale Acoustic Communication: A Feasibility Study Using Tomography M-Sequences", Proc. IEEE Oceans 2001 Conference, Honolulu, HI, Nov. 2001. 2256-2261.

Nesnas, I.A.D., et al. 2012, "Axel and DuAxel Rovers for the Sustainable Exploration of Extreme Terrains". J. Field Robotics, vol. 29, No. 4, pp. 663-685.

F. Davoodi "Exploiting Ekman Spiral Phenomena for Locomotion and Controlling the Trajectory and the Speed of the Buoys, AUVs, or Robo Jellies on the Surface and Near the Surface of the Open Seas" Caltech Patent Office CIT File No. CIT-6531-P-2 Filed: Apr. 24, 2014. 52 pages.

J. Asama, et al. "Design investigation of a coreless tubular linear generator for a Moball: A spherical exploration robot with wind-energy harvesting capability" 2015 IEEE International Conference on Robotics and Automation (ICRA) May 26030, 2015, pp. 244-251.

Tadessa, Y. et al. "Hydrogen-fuel-powered bell segments of biomimetic jellyfish" *Smart Mater. Struct.* 21 045013. doi:10.1088/0964-1726/21/4/045013. Published Mar. 20, 2012. 17 pages.

W. Trogler, M. Sailor Nanostructure Porous Silicon and Luminescent Polysiloles as Chemical Sensors for Carcinogenic Chromiom(VI) and Arsenic(V) http://cfpub.epa.gov/ncer_abstracts/index.cfm/fuseaction/display.abstractDetail/abstract/2368/report/ 5 pages.

Sadeghi M. et al. "Hair-based sensors for micro-autonomous systems" Proc. of SPIE 2012 vol. 8373 p. 83731L-1-83731L-8.

Ultra-Small, Low Power Digital Temperature Sensors TSYS02, MEAS Deutschland GmbH. (www.meas-spec.com/temperaturesensors/digital-temperature-sensors/digitaltemperature-sensors.aspx) 3 pages.

MEMS pressure sensor: LPS331AP. Mar. 2012. (www.st.com/web/catalog/sense_power/FM89/SC1316/PF25160) 36 pages.

STMicroelectronics "STMicroelectronics Launches Single-Chip Magnetometer, Extending Leading Sensor Portfolio for Mobile and Consumer Applications" (www.st.com/web/en/press/p3339) 2 pages.

Ocean Optics Inc. "USB2000 Miniature Fiber Optic Spectrometer". (www.oceanoptics.com/Products/usb2000.asp) 2010. 30 pages.

BTech Acoustics, LLC. "Model BT-1RCL" 2010. 1 page.

Free Spirit Energy. "Windwalker 250 and Mounting Options" 2015. 1 page.

QinetiQ North America "Underwater Optical Communications" downloaded from the internet Oct. 29, 2015. 1 page.

Buckle, J.R. et al. "Autonomous Underwater Vehicle Thermoelectric Power Generation" Journal of Electronic Materials vol. 42, (7), p. 2214-2220, Jul. 2013.

Villanueva, A. et al. "A biomimetic robotic jellyfish (Robojelly) actuated by shape memory alloy composite actuators" Bioinspiration & Biomimetics. 6 (2011) doi: 10.1088/1748-3182/6/3/036004. 16 pages.

Micro Electric Heaters. "Tubular Heaters" 2011. 2 pages.

Boedeker Plastics, Inc. "Tefzel ETFE Specifications" 2015. 2 pages.

Stofan, E. "Titan Mare Explorer (TiME): First Exploration of an Extraterrestrial Sea" 7 pages.

Oleson, S. et al. "Titan Submarine: Exploring the Depths of Kraken Mare" Space Conferences and Exposition. Aug. 31-Sep. 2, 2015. Pasadena, CA. AIAA Space 2015 Conference and Exposition. 15 pages.

R. Beckhusen "To See in the Arctic, DARPA Might Stick Sensors on Icebergs" Sep. 19, 2012. http://www.wired.com/2012/09/arctic-sensors/ 5 pages.

Demir et al. "Convex Optimization Formulation of Density Upper Bound Constraints in Markov Chain Synthesis" American Control Conference, Jun. 4-6, 2014. p. 483-488.

Acikmese et al. "Markov Chain Approach to Probabilistic Guidance for Swarms of Autonomous Agents" Asian Journal of Control, vol. 17, No. 4, pp. 1105-1124, Jul. 2015.

Acikmese et al. "Probabilistic Swarm Guidance for Collaborative Autonomous Agents" American Control Conference, Jun. 4-6, 2014. p. 477-482.

L. Daniel "Defense Department, services monitor Arctic melting". Jun. 28, 2011, American Forces Press Service. 2 pages.

M. Allouche, (2000) "The Integration of UAVs in Airspace", Operations & Safety, Air & Space Europe, vol. 2, No. 1, pp. 101-104.

P. V. Blyenburgh, (1999), "UAVs: an Overview", Uninhabited Aerial Vehicles (UAVs), Air & Space Europe, Wol 1, No. 5/6, pp. 43-47.

B.A. Warneke, et al. (2002) "An autonomous 16 mm3 solar-powered node for distributed wireless sensor networks", IEEE Sensors, vol. 2, pp. 1510-1515.

H. Cunfu, et al. (2000) "Theoretical and experimental studies of torsion deformation of a thin-walled tube with wound and pasted shape memory alloy wires", Journal of Smart Materials and Structures, vol. 9, pp. 660-664.

G. Park, et al. (2002) "Dynamic testing of inflatable structures using smart materials", Journal of Smart Materials and Structures, vol. 11, pp. 147-155.

A. Ansari. et al. (2011) "Gallium nitride-on-silicon micromechanical overtone resonators and filters," IEEE Electron Device Meeting (IEDM 2011), pp. 1-6.

H.D. Griffiths et al. (2005) "Passive coherent location radar systems. Part 1: performance prediction", IEEE Proceedings of Radar, Sonar and Navigation, vol. 152, No. 3, pp. 153-159.

T.B. Koay, et al. (2006), "Advanced PANDA for high speed autonomous ambient noise data collection and boat tracking—system and results", IEEE Oceans 2006—Asia Pacific, pp. 1-9.

(56) References Cited

OTHER PUBLICATIONS

N. Ghafouri et al. (2008) "A Micro Thermoelectric Energy Scavenger for a Hybrid Insect", IEEE Sensors, pp. 1249-1252.
I. Ferreira et al. (2010) "Self-Rechargeable Paper Thin-Film Batteries: Performance and Applications", IEEE Journal of Display Technology, vol. 6, No. 8, pp. 332-335.
K. Najafi et al. "Microsystems for Energy Harvesting," Invited Paper, *16th International Conference on Solid-State Sensors, Actuators, and Microsystems (IEEE Transducers)*, Beijing China, pp. 1845-1850, Jun. 2011.
D. S. Bayard et al. "Probabilistic Guidance for Earth Orbiting Spacecraft Swarms," Jet Propulsion Laboratory, JPL D-72983, Apr. 10, 2012.
B. Acikmese et al. "Probabilistic Guidance for Swarms of Autonomous Agents," Jet Propulsion Laboratory, JPL D-73778, Jun. 21, 2012.
Hadaegh, F. et al. "Chapter 2: New Guidance, Navigation, and Control Technologies for Formation Flying Spacecraft and Planetary Landing" *Advances in Control System Technology for Aerospace Applications*, Eric Feron (Ed.), Aerospace Decision and Control, Lecture Notes in Control and Information Sciences (LNCIS), Springer, 2016, pp. 49-80. ISBN: 978-3-662-47693-2.
A. Villanueva et al. "A bio-inspired shape memory alloy composite (BISMAC) actuator", Smart Mater. Struct. 19, 025013 (2010) 17 pages.
Joshi, K. et al. "Modeling of Artificial *Aurelia aurita* Bell Deformation", Marine Technology Society Journal 45, 165-184 (2011).
S. Priya, "Criterion for Material Selection in Design of Bulk Piezoelectric Energy Harvesters", IEEE Ultrason. Freq. Ferroelect. Cntrl. 57, 2610-2612 (2010).
V. Bedekar, et al. "Pen Harvester for Pulse Rate Sensor", J. Phys. D—Appl. Phys. 42 105105 (2009). 9 pages.
A. Marin, et al. "Multiple cell configuration electromagnetic energy harvester", J. Phys. D—Appl. Phys. 44, 295501 (2011). 11 pages.
A. Marin, et al. "Multimodal Vibration Harvester Using Inductive and Magnetostrictive Mechanisms", Integrated Ferroelectrics 125, 111-122 (2011).
Joshi, K. et al. "Estimation of Solar Energy Harvested for Autonomous Jellyfish Vehicles (AJVs)", IEEE Journal of Oceanic Engineering, vol. 36, No. 4, p. 539-551. Oct. 2011.
Landau, L.D. et al. (1976). Course of Theoretical Physics: vol. 1 Mechanics. Butterworth-Heinenann. pp. 33-34. ISBN 0750628960.
Zhao, B. et al. "Dynamics and motion control of a two pendulums driven spherical robot" Intelligent Robots and Systems (IROS), 2010 IEEE/RSJ International Conference on , vol., No., pp. 147,153, Oct. 18-22, 2010 doi: 10.1109/IROS.2010.565115.
D. V. Balandin, D.V. et al. "A motion control for a spherical robot with pendulum drive" Journal of Computer and Systems Sciences International Jul. 2013, vol. 52, Issue 4, pp. 650-663.
Basic, G. "Power-Scavenging Tumbleweed Rover" Graduate Department of Aerospace Engineering, University of Toronto (2010) 99 pages.
Oh, Y.S. et al. "Use of microorganism-immobilized polyurethane foams to absorb and degrade oil on water surface." Appl. Microbiol. Biotechnol. (2000) 54: 418-423.
Ervasti, M. et al."iShake: Mobile Phones as Seismic Sensors—User Study Findings", U.C. Berkeley. *MUM'11*, Dec. 7-9, 2011, Beijing, China. retrieved from http://glaser.berkeley.edu/glaserdrupal/pdf/cmum11%20Ervasti.pdf.
Van Gorp et al. "Optical design and performance of the Ultra-Compact Imaging Spectrometer" Proc. SPIE 8158 pp. 81580L-2-81580L-10 (2011): doi: 10.1117/12.892422.
Cunio et al. "Options in the solar system for planetary surface exploration via hopping", IEEE Aerospace Conference, paper #1680, Version 4, Updated Jan. 12, 2011. 10 pages.
"Remote Explosives Detection" www.gs.flir.com/products/icx-detection/explosives/fido-onboard/. Retrieved Jul. 2, 2013.
"TES and Cosmic Microwave Background Detection" www.microdevices.jpl.nasa.gov/capabilities/superconducting-devices/tes-bolometers.php. Retrieved Jul. 2, 2013.

Norford, L. et al. "Piezoelectric MEMS airflow sensor for wind velocity and direction measurement" www.pdfdownload.org/pdf2html/view_online.php?url=http%3A%2F%2Fcensam.mit.edu%2Fnews%2Fposters%2F2010%2Fnorford%2F4.pdf. Retrieved Jul. 2, 2013.
W. Carroll, "Submarine Numbers at Issue", Jun. 30, 2009, 2 pages, http://defensetech.org/2009/06/30/submarine-numbers-at-issue/ (defensetech.org/2009/06/30/submarine-numbers-at-issue/#ixzz2zs3TdeBB).
CBS News, "25 Countries now helping search for Malaysia Airlines Flight 370", Mar. 16, 2014, 6 pages. http://www.cbsnews.com/news/malaysia-airlines-flight-370-25-countries-helping-search-for-missing-plane/.
"Ocean", National Oceanic and Atmospheric Administration, United States Department of Commerce, downloaded from the internet Aug. 7, 2015. 2 pages. http://www.noaa.gov/ocean.html.
"Ocean in Motion: Ekman Transport-Background", Ocean Motion and surface currents, downloaded from the internet Aug. 7, 2015. 2 pages. http://oceanmotion.org/html/background/ocean-in-motion.htm.
A. Clites "Observation of Concurrent Drifting Buoy and Current Meter Measurements in Lake Michigan", Journal of Great Lakes Research 15(2) 1989: pp. 197-204.
DuPont "DuPont Tefzel ETFE Fluoroplastic Film" Downloaded from the internet Aug. 7, 2015. 3 pages. https://www.chemours.com/Teflon_Industrial/en_US/assets/downloads/Chemours_Tefzel_ETFE_Film_Properties_Bulletin_K26943.pdf.
K-Mac Plastics "Tefzel ETFE Properties" Downloaded from the internet Aug. 7, 2015. 2 pages. http://kmac-plastics.net/data/technical/etfe.htm.
M. Stojanovic, "Retrofocusing Techniques for High Rate Acoustic Communications", Journal of the Acoustical Society of America, vol. 117 (3), Pt. 1, Mar. 2005, pp. 1173-1185.
M. Stojanovic et al., "Multichannel Detection for Wideband Underwater Acoustic CDMA Communications", IEEE Journal of Oceanic Engineering, vol. 31, No. 3, Jul. 2006, pp. 685-695.
M. Stojanovic et al. "Phase-Coherent Digital Communications for Underwater Acoustic Channels", IEEE Journal of Oceanic Engineering, vol. 19, No. 1, Jan. 1994, pp. 100-111.
M. Stojanovic et al., "Adaptive Multichannel Combining and Equalization for Underwater Acoustic Communications" Journal of the Acoustical Society of America, vol. 94-(3), Pt. 1, Sep. 1993, pp. 1621-1631.
P. Abad-Manterola et al. "Wheel Design and Tension Analysis for the Tethered Axel Rover on Extreme Terrain", IEEE Aerospace Conference, Big Sky, MT, vol. 2009. pp. 1-8.
P. Abad-Manterola, et al. "Axel: A Minimalist Tethered Rover for Exploration of Extreme Planetary Terrains". IEEE Robotics and Automation Magazine, vol. 16 (4). 2009 pp. 44-52.
M. Tanner et al. (2013) "Online Motion Planning for Tethered Robots in Extreme Terrain". 2013 IEEE International Conference on Robotics and Automation (ICRA)., Piscataway, NJ, pp. 5557-5564.
F. Davoodi et al. (2014) "A Self-Powered Intelligent Network of Controllable Spherical Sensors to Explore Solar Planets and Moons", AIAA Space 2014 Conference & Exposition.
F. Davoodi et al. (2015) "Moball-Buoy Network: a Near-Real-Time Ground-Truth Distributed Monitoring System to Map Ice, Weather, Chemical Species, and Radiations, in the Arctic", 11th Annual Polar Technology Conference, Mar. 2015, Denver, CO.
F. Davoodi et al. (2014) " Re-Entry Hopper-Aero-Space-Craft System on Mars (REARM-Mars)", AIAA Space 2014 Conference & Exposition.
J.O. Dabiri (2005) "On the Estimation of Swimming and Flying Forces from Wake Measurements", Journal of Experimental Biology vol. 208., pp. 3519-3532.
J.O. Dabiri et al. (2005) "Vortex Motion in the Ocean: In Situ Visualization of Jellyfish Swimming and Feeding Flows", Physics of Fluids 17, 091108.
J.O. Dabiri et al.(2005) "The Role of Optimal Vortex Formation in Biological Fluid Transport", Proceedings of the Royal Society B: Biological Sciences 272: 1557-1560.

(56) References Cited

OTHER PUBLICATIONS

J.O. Dabiri et al. (2005) "Starting Flow Through Nozzles with Temporally Variable Exit Diameter", Journal of Fluid Mechanics vol. 538, pp. 111-136.
J.O. Dabiri et al. (2005) "Flow Patterns Generated by Oblate Medusan jellyfish: Field Measurements and Laboratory Analyses", The Journal of Experimental Biology vol. 208., pp. 1257-1265.
F. Davoodi et al. (2015) "A Phase-Changing Pendulum to Control Spherical Robots and Buoy Sensors", Tech Brief Journal, Feb. 1, 2015.
L. Freitag et al. "The WHOI Micro-Modem: An Acoustic Communications and Navigation System for Multiple Platforms" IEEE Oceans Sep. 19, 2005.
S. Mackay "Robotic Jellyfish Could One Day Patrol Oceans, Clean Oil Spills, and Detect Pollutants", VirginiaTech, May 29, 2012, 4 pages.
F. Davoodi et al. (2012) "Gone with the wind on Mars (GOWON): A wind-driven networked system of mobile sensors on Mars", Lunary and Planetary Institute Workshop on Mars Exploration Concepts and Approaches, Jun. 2012, http://www.lpi.usra.edu/meetings/marsconcepts2012/pdf/4238.pdf.
F. Davoodi et al., (2012) "A Design for the Structure and the Mechanic of Moballs", JPL & NASA Case Nos. NPO 48643. NASA Tech Briefs, Oct. 17-18, 2012.
R. Johnson, (2012) "Russia and Canada Move Troops to the North Pole to Assert Territorial Interests", Business Insider, last consulted on Jul. 4, 2012 at: http://articles.businessinsider.com/2011-07-07/news/30089753_1_fighter-jets-continental-shelf-barrels.
CBC news Canada, (2010) "Battle for the Arctic heats up", last consulted on Jul. 4, 2012 at http://www.cbc.ca/news/canada/story/2009/02/27/f-arctic-sovereignty.html.
Spiegel Online, (2007) "The Race for the Arctic", last consulted on Jul. 4, 2012 at http://www.spiegel.de/international/world/cold-wars-in-the-arctic-canada-takes-on-russiain-race-for-north-pole-a-499287.html.
C. Boyd, (2012) "Mine Kafon: Wind-blown landmine clearance", last consulted on Jul. 4, 2012 at http://www.bbc.com/future/story/20120503-blowing-in-the-wind.
P. Wadhams, (2012) "Arctic Ice Cover, Ice Thickness and Tipping Points", AMBIO—journal of the human environment, vol. 41, No. 1, pp. 23-33.
M.Bettwy, NASA, (2012) "Changes in the Arctic: Consequences for the World", last consulted on Jul. 4, 2012 at http://www.nasa.gov/centers/goddard/earthandsun/arctic_changes.html.
NCEP/NCAR Reanalysis data, (2007), last consulted on Jul. 4, 2012 at http://www.cdc.noaa.gov/cgi-bin/DataMenus.pl?dataset=NCEP.
Cooperative Institute for Research in Environment Sciences, (2011), last consulted on Jul. 4, 2012 at http://cires.colorado.edu/science/pro/parca/.
NASA. "Cryospheric Science at NASA" downloaded from http://ice.nasa.gov/ on Aug. 12, 2015.
National Defense and the Canadian Forces, (2012) "The Distant Early Warning (DEW) Line Clean-up Project", last consulted on Jul. 4, 2012 at http://www.forces.gc.ca/en/news/article.page?doc=the-distant-early-warning-line-clean-up-project/hnmx19pm.
J. Baglole, "North Warning System—Protecting North America's Backdoor", last consulted on Jul. 4, 2012 at http://usmilitary.about.com/od/weapons/a/northwarning.htm.
North American Aerospace Defense Command, (2012) " NORAD Agreement", last consulted on Jul. 4, 2012 at http://www.norad.mil/AboutNORAD/NORADAgreement/tabid/3428/mid/7417/dn-nprintmode/true/Default.aspx?SkinSrc=%5bG%5dSkins%2f_default%2fNo+Skin&ContainerSrc=%5bG%5dContainers%2f_default%2fNo+Container.
P. F. Gorder, (2003) "Sizing Up Smart Dust", Computing in Science & Engineering, vol. 5, No. 6, pp. 6-9.
I. Chatzigiannakis et al. (2003) "A Sleep-Awake Protocol for Information Propagation in Smart Dust Networks", Proceedings of the International Parallel and Distributed Processing Symposium (IPDPS 2003), pp. 1-8.
J.A. Jones, (2001) "Inflatable Robotics for Planetary Applications", 6th International Symposium on Artificial Intelligence, Robotics and Automation in Space, I-SAIRAS. Montreal, Canada.
A. Behar, NASA-JPL, (2004), "Tumbleweed Polar Rover", IEEE Aerospace Conference, Big Sky, Montana, Mar. 6-13, 2004. last consulted on Jul. 4, 2012 at http://trs-new.jpl.nasa.gov/dspace/bitstream/2014/39171/1/04-0014.pdf.
R. Amirtharajah, et al., (2006), "Circuits for Energy Harvesting Sensor Signal Processing", 43rd ACM/IEEE Design Automation Conference, pp. 639-644.
Niklaus et al. "MEMS-Based Uncooled Infrared Bolometer Arrays—A Review" Proceedings of SPIE, vol. 6836 68360D-2.
K. Najafi et al. (2012), "Energy Scavenging From Low Frequency Vibrations", NIST-funded project at the Engineering Research Center for Wireless Integrated MicroSystems, http://www.eecs.umich.edu/najafi/files/energyscavenging.pdf.
K. Najafi et al. (2012), "A Micro Thermoelectric Generator for Microsystems", DARPA-funded project at the Engineering Research Center for Wireless Integrated MicroSystems, http://www.eecs.umich.edu/najafi/files/microthermgen.pdf.
R.O. Warrington, et al. (2012), "MEMS-Based Energy Harvesting for Low-Frequency Vibrations", WIMS ERC-funded project at the Engineering Research Center for Wireless Integrated MicroSystems, http://www.eecs.umich.edu/najafi/files/MEMSbased.pdf.
D.Bouchouicha et al. (2010) "Ambient RF Energy Harvesting", International Conference on Renewable Energies and Power Quality (ICREPQ 2010), Granada, Spain, pp. 1-5.
K. Najafi et al. (2012), "Integrated Low-Power, High-Pressure, High-Flow Gas Micropump", WIMS ERC-funded project at the Engineering Research Center for Wireless Integrated MicroSystems, http://www.eecs.umich.edu/najafi/files/integratedlowpower.pdf.
W. Khun, et al. (2007) "Microtransceiver for UHF Proximity Links Including Mars Surface-to-Orbit Applications", Proceedings of the IEEE, vol. 95, No. 10, pp. 2019-2044.
B. Acikmese et al. (2012) "A Markov Chain Approach to Probabilistic Swarm Guidance," 2012 American Control Conference (ACC), Montréal, Canada. Jun. 27-29, 2012.
Y. Tadesse et al. (2010) "Tailoring the Response Time of Shape Memory Alloy Wires through Active Cooling and Pre-stress", J. Intell. Mater. Sys. Struct. 21, 19-40.
Rutgersprep.org (2008) "Aquabots: Robots of the Deep" downloaded from http://www.rutgersprep.org/kendall/7thgrade/cycleA_2008_09/zi/robo-AQUA4.html.
Marlow "EHA-PA1AN1-R02-L1 EverGen Energy Harvesters" downloaded from http://www.marlow.com/eha-pa1an1-r02-I1.html.
PCT International Search Report mailed Oct. 16, 2013 for PCT/US2013/046656 filed on Jun. 19, 2013 in the name of California Institute of Technology.
PCT Written Opinion mailed Oct. 16, 2013 for PCT/US2013/046656 filed on Jun. 19, 2013 in the name of California Institute of Technology.
Joyce B., "Development of an Electromagnetic Energy Harvester for Monitoring Wind Turbine Blades." MS Thesis. Virginia Polytechnic Institute and State University. Dec. 12, 2011. http://scholar.lib.vt.edu/theses/available/etd-12202011-195538/unrestricted/Joyce_BS_T_2011.pdf . Retrieved Jul. 2, 2013.
Kume, H. "Fujifilm Shows High-efficiency Thermoelectric Converter Using Organic Material." www.techon.nikkeibp.co.ip/enQlish/NEWS EN/20130206/264517/ . Retrieved Jul. 2, 2013.
Najafi K., et al. "Microsystems for Energy Harvesting," Invited Paper, 16th International Conference on Solid-State Sensors, Actuators, and Microsystems (IEEE Transducers), Beijing China, pp. 1845-1850, Jun. 2011.
"Waspmote Datasheet" www.libelium.com/documentation/waspmote/waspmote-datasheet_eng.pdf. Retrieved Jul. 2, 2013.
Repas, R. Sensor Sense: Metal-faced inductive sensors for Durability. Machine Design. Nov. 6, 2012. www.machinedesign.com/article/metal-faced-inductive-sensors-for-durability-1106. Retrieved Jul. 2, 2013.
Synkera Technologies Inc. www.Synkera.com. Retrieved Jul. 2, 2013.

(56) References Cited

OTHER PUBLICATIONS

Vectornav: Embedded Navigation Solutions www.vectornav.com. Retrieved Jul. 2, 2013.
Persaud, R."LEACH Protocol for Wireless Sensor Networks". www.cs.Qsu.edu/yli/teachinQ/Fall1 O/sensor/Slides/rp.pdf. Retrieved Jul. 2, 2013.
"Gamma Spectroscopy" www.ortec-online.com/Solutions/gamma-spectroscopy.aspx. Retrieved Jul. 2, 2013.
Nunez, J. I. et al. "The Multispectral Microscopic Imager (MMI) with Improved Spectral Range and Resolution" 40 Lunar and Planetary Science Conference. 2009.
Gellert, R. "Alpha Particle X-ray Spectrometer (APXS)" www.msl-scicorner.jpl.nasa.gov/Instruments/APXS/. Retrieved Jul. 2, 2013.
Jet Propulsion Laboratory Microdevices Laboratory. 2009 Annual Report. www.instrumentsystems.ipl.nasa.Qov/docs/MDL_AR09_041310.pdf. Retrieved Jul. 2, 2013.
Sinha, M.P. et al. "Laser ablation-miniature mass spectrometer for elemental and isotopic analysis of rocks" Review of Scientific Instruments. Sep. 2011. 82(9).
"The World's Largest Deserts". www.geology.com/records/largest-desert.shtml. Retrieved Jul. 2, 2013.
Harrington, P. et al, "Relationship between Reservoir Quality and Hydrocarbon Signatures Measured at the Surface" Search and Discovery Article #41078 (2012). Posted Nov. 26, 2012.
"Sensor Boards" www.libelium.com/products/waspmote/sensors. Retrieved Jul. 2, 2013.
Holstein-et al. Winds at the Phoenix landing site. J. Geophys. Res. 115, E00E18, doi:10.1029/2009JE003411, 2010.
Almeida et al. "Giant saltation on Mars". Proc. Natl. Acad. Sci. 105, 6222-6226, 2008.
Bertelsen et al. "Magnetic Properties Experiments on the Mars Exploration Rover Spirit at Gusev Crater". Science 305, 827 (2004). http://marsrovers.jpl.nasa.gov/newsroom/pressreleases/20110901a.html.
www.nasa.gov/offices/oct/early_stage_innovation/niac/short_printable_spacecraft.html.
Mandrake et al. "Automated Neutral Region selection using superpixels". Hyperspectral Image and Signal Processing: Evolution in Remote Sensing (Whispers). Jun. 14-16, 2010.
www.nasa.gov/vision/earth/technologies/tumbleweed.html.
Delin et al. "The Sensor Web: A New Instrument Concept." SPIE Symposium on Integrated Optics. Jan. 20-26, 2001. San Jose, CA.
Dubowsky et al. "A Concept Mission: Microbots for Large-Scale Planetary Surface and Subsurface Exploration" STAIF 2005 pp. 1449-1458.
Notice of Allowance mailed Sep. 25, 2014 for U.S. Appl. No. 12/776,652, filed in the name of Davoodi et al. on Feb. 25, 2013.
Notice of Allowance mailed Aug. 26, 2014 for U.S. Appl. No. 12/776,652, filed in the name of Davoodi et al. on Feb. 25, 2013.
Notice of Allowance mailed Aug. 14, 2014 for U.S. Appl. No. 12/776,652, filed in the name of Davoodi et al. on Feb. 25, 2013.
OCEANOPTICS "USB2000+ (Custom)" downloaded from the internet on Aug. 13, 2015.
SATPHONESTORE "Iridium Core 9523 Modem" downloaded from the internet on Aug. 13, 2015.
Ocean Portal Team "Gulf Oil Spill" downloaded from the internet on Aug. 13, 2015.
Lodolce et al. "Ice Surface Penetration Experiment for Arctic Research (Ice SPEAR) Final Report" Sep. 9, 2013.
Office of Naval Research et al. "Naval Operations in an Ice-Free-Arctic" Naval Operations in an Ice-Free Arctic Symposium, Apr. 17-18, 2001.
Parkinson et al. "Arctic sea ice variability and trends, 1976-2006", J. Geophys. Res. 113(C7), 2008.
Simpson et al. "Halogens and their role in polar boundary-layer ozone depletion" Atmos. Chem. Phys., 7, pp. 4375-4418, 2007.
Overland, J.E. "Meteorology of the Beaufort Sea", J. Geophys. Res. 114, C00A07, 2009.
Xiao L. et al. Simultaneous routing and resource allocation via dual decomposition: Communications, IEEE Transactions on 52.7 (2004): 1136-1144.
Houtan et al. "A Case Study of Participatory Data Transfer for Urban Temperature Monitoring" Web and Wireless Geographical Information Systems, Kyoto, Japan, Mar. 2011.
Houtan et al. "Using Location Based Social Networks for Quality-Aware Participatory Data Transfer" ACT SIGSPATIAL, LBSN, San Jose, California, Nov. 2010.
International Search Report for International Application No. PCT/US2015/033845 filed Jun. 2, 2014 on behalf of California Institute of Technology. Mailed Aug. 31, 2015.
Written Opinion for International Application No. PCT/US2015/033845 filed Jun. 2, 2014 on behalf of California Institute of Technology. Mailed Aug. 31, 2015.
International Search Report and Written Opinion for International Application No. PCT/US2015/033846 filed Jun. 2, 2015 on behalf of California Institute of Technology. Mailed Sep. 23, 2015.
Non-Final Office Action for U.S. Appl. No. 14/538,771, filed Nov. 11, 2014 on behalf of Faranak Davoodi. Mail Date: Oct. 13, 2016. 16 pages.

\* cited by examiner

CONTROLLABLE BUOYS AND NETWORKED BUOY SYSTEMS

CROSS REFERENCE TO RELATED APPLICATIONS

The present application claims priority to U.S. Provisional Application No. 62/006,698 filed on Jun. 2, 2014, and U.S. Provisional Application No. 62/153,322 filed on Apr. 27, 2015, the disclosures of which are incorporated herein by reference in their entirety. The present application may also be related to U.S. patent application Ser. No. 14/729,007, titled "CONTROLLABLE BUOYS AND NETWORKED BUOY SYSTEMS", and filed concurrently herewith, the disclosure of which is incorporated herein by reference in its entirety.

STATEMENT OF FEDERAL GOVERNMENT SUPPORT

The invention described herein was made in the performance of work under a NASA contract, and is subject to the provisions of Public Law 96-517 (35 USC 202) in which the Contractor has elected to retain title.

TECHNICAL FIELD

The present disclosure relates to a few specific architectures and designs of the controllable and reconfigurable networked buoy systems. More particularly, it relates to controllable and reconfigurable networked buoy systems capable of monitoring and providing communication over an area of interest on the surface, inside, or under the surface of the ice or water. The networked controllable buoy systems could provide monitoring, communication, positioning capabilities and exhibit persistence, intelligence and controllable maritime networking, between the above-sea communication nodes and instruments (e.g., satellites, airplanes and balloons) to the surface (e.g., vessels) and submerged underwater instruments and vehicles, such as submarines, and seabed oil-structure instruments and sensors over vast marine regions.

SUMMARY

In a first aspect of the disclosure, a buoy is described, the buoy comprising a shell; at least one communication device; at least one energy-providing device; and at least one tethered vehicle attached to the buoy by a tethering cable, the tethering cable being spooled in one of the shell or the at least one tethered vehicle.

In a second aspect of the disclosure, a buoy is described, the buoy comprising: a shell; at least one communication device; at least one energy-providing device; at least one propulsion unit; and an extendible tube comprising a means for penetrating ice.

In a third aspect of the disclosure, a method to organize a plurality of buoys is described, the method comprising: providing a plurality of buoys, each buoy comprising: a shell; at least one sensor; at least one communication device; at least one energy-providing device; at least one processor; a plurality of spoolers, each spooler comprising a motor, the motor configured to deploy and reel-in a tethering cable; and a plurality of tethered vehicles attached to the buoy by the tethering cable, the plurality of tethered vehicle each comprising a propulsion unit, at least one further communication device and at least one further sensor; and programming the plurality of buoys with a plurality of contingencies and behaviors.

In a fourth aspect of the disclosure, a method to organize a plurality of buoys is described, the method comprising: providing a plurality of buoys, each buoy comprising: a shell; at least one sensor; at least one communication device; at least one energy-providing device; at least one processor; and at least one propulsion unit; and programming the plurality of buoys with a plurality of contingencies and behaviors.

Controllable Buoys

The present disclosure describes controllable buoys (also referred to as just "buoys") and buoy systems deployed in a liquid environment, for example, a pool, lake, ocean, or even a liquid methane sea on an astronomical body.

The buoys are controllable in the sense that they are capable of controlled movement or getting configured to perform some certain tasks in some certain time, location, or situations. The task could be relaying data and communication signals from other buoys or external communication assets, such as the satellites, submarines, vessels, balloons, or airplane missioned in the area. The task could also be to perform environmental sensing and mapping some environmental factors (e.g., wind speed, temperature, water salinity, pollutants, bathometry, presence of the ice), perform computation on the collected data (e.g. getting average on them), and relaying the collected data back to the network and the system's stakeholders. Conversely, the movement can include buoy's movement along the surface of the water, and this can include changing the buoyancy of the buoy, to sink to a certain depth or return to the surface under certain predefined circumstances, to launch its tethered-underwater-vehicle into the deeper water, or to retrieve them by tethering them up to the surface, to move to a newly defined area, or to change location based on sensor readings from the buoy. Control can exist to the collection of the networked buoys and in a collaborative and distributed fashion. The buoys, which have peer-to-peer communication with each other, might decide to share tasks in order to optimize the performance of the system (e.g., covering an area of interest with the resolution given by the stakeholders), or to save the available resources of the system such as the power (for example not all neighboring buoys would repeat the same exact list of tasks when they are within a spatial resolution defined by the stakeholders). Instead, they can negotiate with each other such that each buoy would perform only a few of the tasks requested and they will finish all the tasks given with their collaboration. Control includes a buoy's learning from the experience of the other networked buoys. For example, if one buoys goes in a certain area where there exist a hazardous object or event (e.g., falling ice or crushing waves), it might warn the other networked buoys to avoid the hazardous area to stay safe. On the other hand if the stakeholders are interested to search for some certain event, such as the presence of methane plumes (valuable for oil companies), and if one buoy would find a considerable amount of them in an area, it might instruct the other networked buoys to leave their lower priority areas (e.g., where there has been no methane plume funded), and move to the higher priority area (e.g., where methane plume has been detected). Control can be directed from an external source through communication with the buoy and/or it can come from a controller within the buoy itself. Control could be centralized or decentralized fashion. The centralized control could include when an external source such as the stakeholders or a remote super computer, via the satellite or through the network of the buoys, would instruct a certain buoy to perform some certain task (e.g., to move to an exact geo location, take a picture of any moving object in the area, and send the data back to the stakeholder via the satellite). The decentralized control could include when some networked buoys would autonomously and collaboratively make decision on what should be done and by which networked buoy. For example, if a buoy needs to decide where to go next (e.g., to the east or to the west), it might query the other networked buoys on their location and decide to go to the area where it was on the plan for monitoring and that currently has no networked buoy there. One embodiment includes an internal controller that can be reconfigured by way of a communication from an external source. Control can include instructions, for example, to remain within a pre-defined area by altering the wind profile of the buoy. Spooling, tethered-underwater-vehicle carrying, controllable buoys as described in the present disclosure can provide a persistent (self-powered) and autonomous monitoring and communication network of mobile and configurable surface-underwater buoys that could be controlled in order to stay in an area of interest (for example, an area of an ocean delimited by GPS co-ordinates). These buoys do not require a vessel and crew present at the location for its operation. Additionally, the persistent buoys provide a detection of problems within the area of interest in a short matter of time, increasing the chance of handling the problems effectively.

The buoys may act in an individual or collective fashion. For example, a single buoy may be deployed in an area, or a group of buoys may be deployed together to form a sensory and/or communication network. The network may be configured to communicate between buoys and have autonomous or semi-autonomous behavior settings for each buoy, thereby allowing the network to act in an organized, collective manner. For example, a first buoy in the network may be dispatched to analyze a specific area. The data from the first buoy may be transmitted through the other buoys in the network in order to reach a location out of reach from the first buoy. The network may also be used to relay a message from vehicles (such as a ship at sea) that are within range of a buoy, to other locations in range of the network. Additionally, the network may be configured to transmit messages in a stealthy or hard-to-detect manner, so that communication can be affected through the network in a secure fashion. Some examples of vehicles that could connect to the network of devices are submarines, ships, airplanes, land vehicles on a coast within range of the network, spaceships, space stations, and satellites.

The buoys can float on the ocean surface or submerse underwater to a desired depth. In some embodiments, the buoys are spherical, but the buoys can be of any shape such as ovoid, cuboid, cone, cylinder, hemispherical, wing-shaped, or boat-shaped.

The buoys of the present disclosure could be made of, for example: a rigidized structure and light but sturdy materials such as fiberglass, carbon fibers; a softer fabric over a rigidized frame such as Dyneema™ or ETFE over fiber glass rods; or a flexible and inflatable materials such ETFE, as in Refs. [9-10]. A buoy can have controllable spools (similar to those in Refs. [17-20]) and tethers connected to the tethered-underwater-vehicle. The tethers, for example, could be made of strong and light materials such as Dyneema™ or Kevlar™. The electricity cords such as copper or nanocarbon cords covered by ETFE (such as those described in www.great-wire.com/product17.htm, the disclosure of which is incorporated herein by reference in its entirety) integrated inside the tether in order to transfer power from the mother-buoy to its TUVs. Fiber optic wires, RF wires, or other communication lines could also be integrated inside the connecting tethers in order to transfer optical communication signals between the mother-buoy and its tethered-underwater-vehicles.

Tethered Underwater Vehicles

In some embodiments, the buoys additionally comprise one or more tethered underwater vehicles (TUVs) attached, internally or externally, to the buoy. For example, a single buoy may be attached to a single TUV, or multiple TUVs may be attached to a single buoy. In some embodiments, the TUVs are attached to a spooling system. The spooling system allows the deploying of and reeling in of the tethering cable, in order for the TUV to move further away from, or be carried back towards, the buoy. The spool for the tether may be inside the buoy, inside the TUV, or external to both, for example in a spooling device underwater that is attached to both the buoy and to the TUV. The spooler may be, for example, a rotating cylinder operated by a motor. The tether may wind around the cylinder to deploy or reel in its length.

The TUVs attached to the buoys are underwater instruments or vehicles, such as a sounder, micro-submarine, an autonomous underwater vehicle (AUV), or a robot. In some embodiments, the buoys are able to move in the ocean, for example having an engine or other means of propulsion. The TUV can be securely attached inside a chamber of the buoy and deployed at a desired time, or attached externally to the buoy. In some embodiments, one or more of the TUVs are able to tow the buoy via the tether in a desired direction.

In some embodiments, the spooler for the TUVs is a tangle-free active spooling mechanism, comprising sensors to measure tether tension during active spooling, tether tension control algorithms, and tether payout scheduling algorithms. Active, tethered robotic systems which rappel upon and down steep terrestrial slopes are described in Refs. [17-20].

In some embodiments, torque sensors can be integrated with the spoolers to detect and adjust the tension of the tethers.

Propulsion

The buoys and TUVs may have a means of propulsion. Some examples of means of propulsion include any type of nautical engine used in submarines or ships, for example propulsions based on jetting (water streams), buoyancy engines, paddles, propellers, or impellers. In some embodiments, the mode of propulsion may be inspired by animals, for example jellyfish style propulsion, where water is pushed backwards by a mechanical action of sections of the buoy/TUV. The buoys and TUVs can also include steering mechanisms, such as wings, rudders, or deformable surfaces.

Some TUVs have multiple means of propulsion for different uses. For example, a TUV can have both a motorized propeller and a buoyancy engine: the propeller, being stronger, being used when the TUV is towing the buoy and the buoyancy engine, being more energy efficient, used when the TUV only has to control its own glide for non-towing activities. In some embodiments, the TUVs are specialized such that TUVs dedicated for towing the buoy have one means of propulsion and TUVs dedicated for non-towing tasks (such as sensing or communication) have a different means of propulsion. The more energy demanding means of propulsion may make use of a dedicated power line in the tether so that the TUV engine is powered by the buoy, whereas more efficient forms of propulsion may be powered by batteries or other energy storing system on the TUV itself. When the TUV is retracted, the buoy may have a recharging connection for the TUV batteries. In some embodiments, the buoys/TUVs may have means of recovering energy from the environment, for example generating electricity from gradients of temperature, solar energy, wind, waves, or water currents.

In some embodiments, there could be mechanical control systems inside the controllable buoy, such as the ones described in U.S. Pat. No. 8,912,892 "AUTONOMOUS AND CONTROLLABLE SYSTEMS OF SENSORS AND METHODS OF USING SUCH SYSTEMS", the disclosure of which is incorporated herein by reference in its entirety. These mechanical control systems could be used inside the controllable buoy in order to make it roll on the surface of the water. The motion, for example, could be similar to that of a human walking inside an inflated plastic ball. This motion could control the orientation of the controllable buoy, e.g. making the buoy rotate, or its speed and direction by changing and adjusting its center of mass.

Both the controllable buoy on the surface and its tethered underwater-vehicle can exploit various control mechanisms in order to stay stationary or to control their speed and trajectory. Some of the control mechanisms that could be used for the controllable buoy on the surface and its tethering underwater-vehicle are: propellers, sails, water or air jets, buoyancy engines, control systems in order to change its coefficient of drag. For example, smart materials and structures could be used, as described in U.S. Pat. No. 8,912,892 as referenced above. The shape of the controllable buoy on the surface or its underwater-vehicles could be changed in order to change their buoyancy and therefore the level of its submergence). Other locomotion methods could comprise artificial jellyfish limbs, rows, hydro-fins, and paddles or any other internal and external mechanics and control systems could be used for both. For example, Doel-Fin™ Hydrofoil Stabilizer could be used, or glider technics as employed by Liquid Robotics™.

The TUVs could also have mechanisms or structures similar to those proposed for the "AQUA robot" as described in www.rutgersprep.org/kendall/7thgrade/cycleA_2008_09/zi/robo-AQUA4.html, the disclosure of which is incorporated herein by reference in its entirety. The AQUA robot is equipped with sensors and cameras and can swim in the water and walk on the seabed.

In some embodiments, the buoys can control their speed and trajectory by controlling their submergence (by deflating and inflating) and adjusting the percentage of their body projected to the wind compared to the part projected to the currents. This method is based on Stokes drift and Ekman transport effects. These effects typically create a difference between wind speed and direction and underwater current speed and direction. For example, when the buoy is partially submerged, higher speed winds and wave motions on the surface would contribute significantly to its overall horizontal movement. However, by fully or nearly fully submerging the buoy, the effect of the high-speed winds will be eliminated and the typically slower currents (e.g., 1.6% to 3.6% of speed of wind) will help the buoys to slow down (this method is also described in Ref. [22]). In this disclosure, the buoys can be designed to exploit these phenomena to actively control their movement (speed and direction) over the surface of the ocean.

In some embodiments, movement of the buoys underwater can be carried out as follows, as referenced to animal movement methods. Crawling, and flying, in animals can be realized by effective coupling of rhythmic body movements with the surrounding environment. For jellyfish swimming, for example, the body acts as a "mechanical rectifier" when interacting with the environment (fluid), converting the local pulsing motion of the umbrella into the global forward velocity.

Biologists have found evidence, as described in Refs. [1] and [2], that such rhythmic body movements are controlled by certain neuronal elements called central pattern generators (CPGs). The CPG receives sensory feedback signals from the body and a high level (non-descriptive) command from the brain whose decision is made based on the environmental information. CPGs have been extensively studied for a wide variety of vertebrates and invertebrates, and their mathematical models have been developed and validated through carefully designed experiments as described in Refs. [3]-[6]. The cell membrane potentials of the neurons within a CPG oscillate at a certain frequency with specific phase relations, generating a pattern for the muscle activation. For instance, the body waves traveling from head to tail in the swimming motion of lampreys or leeches are generated by CPGs formed by weakly coupled segmental oscillators in a chain as described in Refs. [7]-[9]. With sensory feedback, the CPG modifies its oscillation pattern to conform to the biomechanical and environmental constraints as described in Refs. [10]-[14]. CPGs generate natural motion exploiting resonance: CPGs placed in the sensory feedback loop integrate the motion planning and feedback regulation into one step so that appropriate patterns are adaptively generated in response to environmental changes. Animals seem to utilize mechanical resonance to achieve efficient locomotion as described in Refs. [12], [18]. For instance, walking frequency scales with the square root of the reciprocal of the body height as described in Refs. [19]-[21]. The wing beat frequency of some insects and birds scales with the inertia raised to the power close to −0.5 as described in Ref. [22], and roughly with the inverse of the wing length as described in Ref. [23]. The CPG is capable of detecting the resonance and generating a gait that is natural for the given body biomechanics and environmental dynamics.

Studies, such as those described in Refs. [14] and [28], have shown that there are two basic mechanisms for entrainment of a CPG-to-mechanical resonance: positive rate feedback and negative integral feedback. In the former (latter) case, the CPG entrains to the resonance frequency lower (higher) than the intrinsic frequency of the CPG. The analytical result as described in Refs [28] also indicated that the oscillation frequency of the coupled system is closer to the resonance frequency if the intrinsic CPG frequency is further away from resonance. Hence, if a CPG has been optimized over generations to achieve efficient locomotion exploiting a biomechanical resonance, then its intrinsic frequency should be away from the resonance frequency. In fact, studies of certain animals have revealed that the intrinsic frequency of a CPG is much different from the frequency of rhythmic body movements during locomotion. For instance, undulation frequencies in swimming leeches and lampreys are typically larger than the intrinsic CPG frequency by a factor of two or more as described in Refs. [29]-[31]. In this manner, controllable buoys and TUVs can be fabricated with mechanical system that allow motion inspired by biological systems, for example comprising a feedback system that detects and readjust the motion of the mechanical structure (for example a paddle similar to a jellyfish propulsion structure) to perform a more efficient motion.

In some embodiments, the velocity of nonlinear balance flotsam (for example, a floating buoy), can be calculate as follows. The air, wind, drag can be calculated as:

$$F_a = \frac{1}{2} C_{da} P_a A_a |V_a - V_{flotsam}|(V_a - V_{flotsam})$$

while the water drag can be calculated as:

$$F_W = \frac{1}{2} C_{dw} P_w A_w |V_a - V_{flotsam}|(V_a - V_{flotsam})$$

where F is the drag, $C_{da} = C_{dw}$ is the drag coefficient (a function of Reynolds number and shape of the flotsam, 0.47 for sphere), $P_a$ is the air density, $P_w$ is the sea-water density, $A_a$ is the dry portion area of the flotsam influenced by the wind drag, $A_w$ is the wet portion area of the flotsam influenced by the water drag, $V_a$ is the velocity vector of the wind related to the flotsam, and $V_w$ is the velocity of the current and waves (water) related to the flotsam.

Under the assumption that when the buoy has been moving in steady state, interacting with the wind and the oceanic current drags, then $F_a + F_w = 0$. The following equations can then be derived:

$$k = \left(\frac{P_a C_{da} A_a}{P_w C_{dw} A_w}\right)^{\frac{1}{2}} \text{ and: } V_{flotsam} = \frac{V_w + k V_a}{1 + k}$$

thus obtaining the estimated velocity of flotsam, such as a buoy.

In some embodiments, a flooded fairing can be employed for the buoys, minimizing drag in the direction of travel, yet also distributing pressure so that the buoy is passively stable while in motion. Because rapid ascent and descent could be sought in some embodiments, it can be desirable to minimize drag along the heave (vertical) axis. Although shallow-water underwater vehicle systems are often volume-constrained, deeper-diving systems can also be mass-constrained. Because of the larger and heavier structures needed to withstand greater depths, system weight can easily become greater than the minimum displaced volume, and additional displaced volume must be added to the system to reach neutral buoyancy. Usually, extra volume is achieved using pressure-tolerant foam.

Vertical motion can be accomplishing using changes is buoyancy. Because rapid ascent and descent can be sought, a buoyancy engine can be employed that maximizes the total possible change in net buoyancy. For example, movement of oil to change the displaced volume of a buoy could be used. In this example, to increase buoyancy oil is moved from a reservoir inside of the pressure housing to an exterior bladder. To decrease buoyancy, the process is reversed.

In some embodiments, the lower hemisphere of a buoy may comprise arm segments, for example six segments. When fully contracted (closed), the segments form the lower half of the sphere. However, when relaxed (open), the arms can act as a means to provide traction on the ocean floor, as well as a means of rowing propulsion for fine-tuned movement, similar to oblate rowing jellyfish such as *Aurelia aurita*. This rowing propulsion mechanism achieved by jellyfish can be achieved through a cyclical contraction/relaxation of the jellyfish bell. Upon relaxation of the bell (upward stroke), the jellyfish form a stopping vortex in the subumbrellar structure. During contraction (downward stroke), a starting vortex is shed outside the bell margin of the jellyfish, coupling with the stopping vortex, and thus producing a pulsing thrust cycle. For example, these structures are described in Refs. [28]-[32].

Communication

In some embodiments, the TUV can glide as far as the bottom of the ocean. The range of the TUV is typically limited by the length of the tether used. In some embodiments, wired communication, for example through optical fiber or a radio frequency (RF) wire, may be carried out between the TUV and the buoy. A satellite may in turn be in RF communication with the buoy; therefore, a fast and near-real-time communication could be established between a TUV under the water, its corresponding buoy (or "mother-buoy") on the surface of the water, and a satellite in orbit.

Spooling TUV-carrier buoys can enable communication and positioning capabilities and provide near-real time controllable maritime networking for orbiting satellites, airborne vehicles, and vehicles on the sea surface, under the sea surface, and into the deepest points of the sea floors.

In some embodiments, the TUVs can dive underwater at a depth of 500 km to 1500 km or more, under the thermocline layer where the acoustic signals can travel reliably without distortion from turbulence and debris for distances as far as 90 km. For example, acoustic communication under water is described in Refs. [13-16]. Therefore, two or more TUVs under the thermocline layers can be able to communicate with each other and create a reliable acoustic communication network, capable of relaying the information from any tactical node, either on the surface (via the fiber-optic link with their mother-buoys), or an underwater tactical data network node, such as a submarine or seabed fixed fiber-optic base-station, with no distortion. Any node from the tactical data network, when connected to the mother-buoys on the surface, or to the TUV under the water, can connect to this relaying network, and establish two-way communication between specific desired tactical data nodes located several kilometers away. For example, with only 120 TUVs, sited roughly 90 km apart, it is possible to cover a 1,000,000 km² area.

In some embodiments, beam forming can be carried out, as explained in the present disclosure, above. This technique is especially feasible with the buoys of the present disclosure since the surface mother-buoys' positions are controllable, and therefore can be stabilized during the beam-forming process. The signal-to-noise ratio (SNR) gains from beam-forming can be further enhanced by using codes, together providing a long-range acoustic communication capability at many kilometers. Hence, deep and distant nodes can be alerted with simple signals even during multiple TUV failures. Cooperative beam-forming could similarly be enabled on the submerged TUVs, thereby enabling more remote assets to be reached even if their nearby TUV node is damaged.

In some embodiments, "long codes" can be used in the buoy and TUV communication, in order to detect signals reliably at low power. The codes can drive two candidate types of modulation, one intended for coherent detection, and another intended for non-coherent detection. The codes can target low power detection (for example, below 100 mW), for the ability, for example, to wake the receiver buoy from hibernation.

In some embodiments, the buoys with TUVs and the buoys without TUVs may share common communication capabilities, so that a network may be formed by buoys of both types. Buoy to buoy and TUV to TUV/asset communication can also include wireless RF and fiberless optical communications, such as laser or LED signaling.

Energy

Also both the controllable buoy and TUV can use various skills of the art in harvesting energy for the power that their electronics needs. For example, thin-film solar cells laminated in the middle of the outer layer, or thermoelectric systems that use the temperature differences found in the different depths of the water or temperature differences between the structure of the buoy and the cooler water below, can be used to harvest energy. Various electromagnetic or electro-mechanic methods that take advantage of the vibration and the motions caused by the winds, waves, and currents can be used. These are similar to the ones suggested in U.S. Pat. No. 8,912,892 referenced above.

The buoys/TUVs, in some embodiments, could use the temperature differences and natural thermal gradients of the environment in order to harvest energy. For example, when a mother-buoy made of ETFE or other polymers are under direct sunlight for several hours, the outer later and the gas inside the mother-buoy's large cavity can become heated. The temperature difference between the mother-buoy structure and the cooler deeper waters could be used to scavenge power using thermoelectricity techniques. One example of a thermoelectric method to generate power is described in EHA-PA1AN1-R02-L1 from www.marlow.com/products/power-generators/energy-harvesting-kits-1/eha-pa1an1-r02-l1.htm, the disclosure of which is incorporated herein by reference in its entirety. The tethered-underwater-vehicle could also harvest energy exploiting temperature differences between the different layers of water at different depths in the ocean similar to known techniques such as those used by gliders, AUVs, and Argos (for example, as described in: J. R. Buckle, A. Knox, J. Siviter, A. Montecucco "Autonomous Underwater Vehicle Thermoelectric Power Generation", the disclosure of which is incorporated herein by reference in its entirety).

The buoys/TUVs can also harvest energy using the motions vibrations caused by water currents or wind (for example using the techniques described in U.S. Pat. Nos. 7,371,136; 7,641,524; 8,043,133 and 8,287,323 and as described in liquidr.com/technology/energy-harvesting.html, the disclosure of all of which is incorporated herein by reference in its entirety).

Alternatively, hydrogen-fuel can be used as described in: iopscience.iop.org/0964-1726/21/4/045013 by Yonas Tadesse, Alex Villanueva, Carter Haines, David Novitski, Ray Baughman, and Shashank Priya "Hydrogen-fuel-powered bell segments of biomimetic jellyfish", the disclosure of which is incorporated herein by reference in its entirety.

In other embodiments, the buoys/TUVs can use various batteries or fuel for their mobility, control, and electronics. In some embodiments, buoys can use a combination of energy harvesting and storage.

In some embodiments, mechanical systems can be used to generate power. For example, a 10 kg eccentric pendulum mass driven by 1 meter swells in the water can generate 50 Watts of continuous power (accounting for generator inefficiencies), with that power increasing in proportion to the sea swell or pendulum mass. Hence, combined energy harvesting strategies can continuously harvest sufficient energy to power satellite communications as well as onboard computation and sensors. The additional energy harvested by the mother-buoy can be stored in its battery, and transferred to the TUVs, for example via inductive charging of their on-board batteries (when the TUVs are retrieved inside the mother-buoy) or directly to the TUV through a short range copper cable woven and protected inside the tether. This can provide for intermittent bursts of TUV towing. Small amounts of up power (for example about 1 continuous Watt) can also be transmitted over the fiber optic link to the TUV.

In some embodiments, the buoys/TUVs can harvest energy from its own passive motion, however other energy generation and energy scavenging technologies as described in Refs. [32] and [33] can be employed, comprising for example: thermoelectric generators (TEG) as described in Refs. [34] and [35]; Radioisotope Heating Unit (RHU); vibration-based energy harvesting systems as described in Ref. [36]; ambient RF energy harvesting as described in Ref. [37]; thin-film micro-batteries; flexible Solar Arrays embedded in the buoy fabric for summer time energy generation; and installing the buoy's electronics as a pendulum attached to a DC-motor mounted on the buoy rotation axis and back-driving it to generate electricity.

Based on environmental data and simulations, for example based on wind maps, it may be possible to estimate a range of available and probable power (energy) and use these estimates to control the location and energy harvesting of the buoys.

In some embodiments, a wave/vibration energy harvester can be housed inside the upper hemisphere of a buoy, which can be used in conjunction with flexible solar cells placed on the outer surface of the buoy to collect and store energy when the buoy is surfaced. Magnetic levitation based vibrational energy harvesting can be used due to its ability to operate at very low frequencies, as those seen by ocean currents. Also, the nonlinear magnetic stiffness of the energy harvesting device allows for a broadband operation of the harvester. The device can be highly scalable which makes it a logical choice for buoy. When surfaced, buoy can be over buoyant, allowing it to stay afloat using zero energy. This can maximize energy harvesting capabilities, as a buoy can stay afloat for an unlimited time.

At very low speeds, the electrical power needed for propulsion in water is small. This is due to the cubic relationship between speed and the propulsive power needed to overcome drag. For example, if speed is cut in half, then the propulsive power drops to ⅛th of what it was originally. Thus systems that move slowly through the ocean can traverse great distances with little propulsive energy. Of course, there are other efficiencies that do not easily scale with speed. For example, a propulsion system that is designed for optimum efficiency at 4 knots could be inefficient when operated by 0.5 knots. Thus, it is sometimes not advisable to simply run a system at a lower speed to increase energy efficiency. Rather, the propulsion system much be designed explicitly for the desired speed. The endurance that can be achieved by slow-speed motion depends on the specific vehicle system. Buoys, which can operate at very low power and harvest energy from the environment, can be capable of extraordinary long-endurance missions.

Positioning/Localization Awareness

The mother-buoys can also employ GPS since they can be located at the surface and in communication with the satellites. The TUVs can be tethered to the GPS intelligent surface-buoys, and could be equipped with an Inertial Navigation System (INS), for example MEMS Inertial Measurement Unit (3axisgyro/accelerometer/magnetic). The TUVs would then be able to be located when under water (exploiting known techniques and algorithms, for example when the TUVs are surveying oceanographic effects in a larger area and they are tasked to map the measurements with the exact location of where the measurements were made.

A TUV can perform localization by sending an acoustic signal back and up to the surface. Since the TUV can be communicatively connected through a wire or fiber to the tethered mother-buoy, the clocks of the TUV and buoy can be synchronized. Additionally, the mother-buoys on the surface can have access to the global clock (satellite), and therefore their clock could be synchronized with the satellite and among the buoys. After the TUV sends an acoustic signal to the surface, the neighboring mother-buoys can send an acknowledgment signal along with the time the signal was received back to the tethered mother-buoy via an RF signal. The tethered mother-buoy can calculate the exact location of the tethered-underwater-vehicle by finding the distance of each one of the receiver mother-buoys and the tethered-underwater-vehicle. This technique can be termed an "upward" triangulation method for localization and can give an accurate location of the tethered-underwater-vehicle. However, sending a large acoustic signal from a tethered-underwater-vehicle (under the water) can require a lot of energy that might not be possible if the tethered-underwater-vehicle is deep under water and far away from sunlight or other external sources of energy.

Another localization technique is explained as follows. Whenever the system (the tethered-underwater-vehicle itself, the mother-buoy, or any of the base-stations or buoys under the control of the distributed control system) wants to know the exact location of the tethered-underwater-vehicle under water, a communication signal can be exchanged between the mother-buoy and its tethered-underwater-vehicle or vehicles in order to make the necessary arrangements. Subsequently, the tethered mother-buoy can contact two or more of the neighboring mother-buoys in the area in order to synchronize their clocks. Since the buoys have access to the global clock from a satellite, they are able to report their differences with the global clock and therefore synchronize their clocks together. In a next step, each one of the mother-buoys can send an omnidirectional acoustic signal down into the water, comprising the time of its transmission to the mother-buoy that is tethered to the TUV whose location is being determined, for example via a RF communication signal. The tethered-underwater-vehicle can then send an acknowledgment signal to the tethered mother-buoy directly through the connecting wire. The TUV can send an acknowledgment signal for any received acoustic signal (that was sent by the neighboring mother-buoys) along with the time the signal was received by the TUV.

Subsequently, the positioning TUV's mother-buoy can send a communication signal (e.g., acoustic, optic, or RF) under water and the TUV can again send an acknowledgment signal along with the time that it received the communication signal, back to the tethered surface-buoy. Since the TUV and its mother-buoy are connected through a tethered wire, their clocks could be synchronized as well. The time of fly between the communication signals sent by the 3 or more mother-buoys and their geo-location when they had sent the communication signal can be used to locate the distance of the TUV from each one of buoys. In this way, the exact location of the TUV and therefore, the objects or areas witnessed and visited by TUV, can be found. This technique can be termed a "downward" triangulation method for localization.

The position of the TUV can then be determined based on the different time stamps of the signals sent and received by the buoys and the TUV. This embodiment has the advantage that the tethered-underwater-vehicle does not need to send an acoustic signal that requires a lot of energy. The TUV, therefore, can save power, which can be important for the tethered-underwater-vehicle since the TUV is deep under water and away from the major sources of energy harvesting, such as sunlight. When the acoustic signal is received by three different buoys on the surface and having access to the satellites and the global clock, the buoys can be able to perform synchronization and triangulation and determine the exact location of TUVs, other underwater and floating assets (e.g. other buoys, instruments, wellheads, structures, instruments, submarines, etc.), and incidents (e.g. pipe leakages, spillages, hydrographic or oceanographic information, etc.).

Sensors and Equipment

In some embodiments, the controllable buoys can be used to explore various lakes, ocean, rivers for scientific surveys and mapping the environmental factors (pressure, temperature, salinity, etc.). The buoys could also be used to find marine mines or other hazardous objects in the ocean. The buoys and/or their TUVs can be equipped with sonar (active or passive) sensors, various imagers, etc. in order to detect the submarines, or adversary activities. The buoys could also be used to facilitate the communication of industrial assets (such as buoys, wellheads, instruments of gas or oil companies, marine transportation, etc.) to the surface and the base stations such as satellites or ships deployed to the area. The buoys can be used to detect and localize any oil and gas, or any other pollutant leakage or spills in mid-water or on the surface. The buoys can also be used in order to clean up oil spills using special bacteria, or chemicals which are able to disperse or dissolve the oil spills. The buoys can also be equipped with various techniques such as sorbent foams or pumps which can absorb the oil (crude or processed) or any other pollutants. The buoys can also be used in order to detect and alert of tsunamis, hurricanes, etc. and let the endangered neighboring areas prepare for a crisis. The buoys can be used in the Arctic area. When the buoys are equipped by sonar or ultrasound sensors, the buoys can be used to measure the thickness of the ice. The buoys can also be used to measure the effect of any drilling for oil exploration either on the bed of the sea or lakes, or on the ice in the Polar Regions. The buoys can also map the topography of the ice in the Arctic, which could help marine transportation in the Arctic area.

The buoys can also have processing capabilities (for example using Microprocessor PCI-based 750 MHz PowerPC system or Conga BM57) in order to perform different tasks, for example computations and storage related to the data acquired by the sensors.

The buoys can, for example, use all the state of art electronics, software, methods, and materials such as the sensors, imagers, energy harvesting components and techniques, communication components and techniques (RF, optic, acoustic, wired or wireless, antenna), batteries and capacitors, data loggers and memories, controller and processors, data processors, avionics such a magnetometers, accelerometers, GPS, communication transceivers and techniques, navigation instruments and techniques, underwater vehicles and tools, movement controllers such as propellers, buoyancy engine, spooling systems and techniques, which are mentioned in this disclosure, in Table 1, or in the U.S. Pat. No. 8,912,892, can be integrated inside various example embodiments of the controllable networked buoy system and its individual buoys (including the mother-buoy and its TUV).

Customization for Oil Industry or Environmental Controls

The systems of the present disclosure can apply to applications such oil and gas explorations, drilling, as well as transferring oil and gas from the drilling sites to the destination using pipelines or various vessels in the open seas, as well as in the Polar Regions such as the Arctic. Therefore, it can be useful to have an autonomous system which is able to monitor these activities in order to check the health of the infrastructures and report any leakage or broken parts or instruments, to facilitate communication, to give feedback from the instruments (e.g., drilling) and the effect of the activity in the area around. For example, if directional drilling is carried out in an area, it can be useful to adjust the drilling parameters (e.g., speed, pressure, direction) and take into consideration the effects of drilling over the larger area around the drilling site, including in very harsh environments.

In some embodiments, the buoys and/or their TUVs can be equipped with sensors that detect the oil spills and plumes on the surface of or under the water. Some of the sensors and techniques have been described at cioert.org/flosee/detecting-oilgas-plumes/, the disclosure of which is incorporated herein by reference in its entirety. For example, the following devices may be used: 1) Fluorometers (for example Seapoint™ Turbidity Meters are low-power, miniature sensors for turbidity and suspended solids detection and measurement; 2) Acoustic Doppler Current Profiler, as used for example by NOAA to assess leak rate at the well site (for example with the SonTek™/YSI 16-MHz MicroADV™ (Acoustic Doppler Velocimeter); 3) Laser In Situ Scattering and Transmissometry (LISST) measures volume concentrations and size spectra of particles using laser diffraction, measuring the intensity of scattered laser light at different angles (LISST-100X); 4) PAH analysis: One type of hydrocarbon found in oil, polycyclic aromatic hydrocarbons are known carcinogens and detected using gas chromatography on lab samples (Nanostructured Porous Silicon and Luminescent Polysiloles as Chemical Sensors for Carcinogenic Chromium(VI) and Arsenic(V) as described at cfpub.epa.gov/ncer_abstracts/index.cfm/fuseaction/display.abstractDetail/abstract/2368/report/, the disclosure of which is incorporated herein by reference in its entirety; 5) A variety of underwater sensors that use spectrometry (e.g. mass spectrometry) to detect a variety of elements in seawater, including hydrocarbon gases and fluids. 6) Turbidity sensors integrated in the buoy can detect the oil spills since the water polluted with oil are usually darker than the areas with no pollution. Several example sensors to detect oil spills by measuring the turbidity or their methods are mentioned in Table 1 and U.S. Pat. No. 8,912,892.

In some embodiments the buoys or TUVs could be made of various known materials such as oleophilic and water repellent materials, for example comprising sorbent sheets, such as 3M™ Oil & Petroleum Sorbents or microorganism-immobilized polyurethane foams to absorb and degrade oil on water surface as described in www.ncbi.nlm.nih.gov/pubmed/11030581, the disclosure of which is incorporated herein by reference in its entirety, composite magnetic materials made of polyurethane foam, polytetrafluoroethylene spheres, magnetic iron oxide nanoparticles. Additionally, vacuum devices or pumps could be integrated in the structure of the mother-buoys and their tethered-underwater-vehicles in order to clean up the oil plumes on the surface or under the layers of the water. Furthermore, the mother-buoys and their TUVs can carry various chemical dispersants and hydrocarbon-eating bacteria and spread them over the area of the oil spill. The buoys and TUVs can also be designed to act as skimmers. One advantage of using the buoys and TUVs for cleaning up the spillage is that they can act as a controllable distributed system and can scan the area of interest and look for even smaller pockets of the spill. Subsequently, the buoys can report the polluted areas and even perform clean-up in a cost-effective and autonomous way.

One benefit of a mobile and controllable buoy system is for monitoring drilling in the seabed. It is important that the pressure of the injected gas inside the wellhead and the connected canals are controlled in order not to cause major fraction or leakage in the seabed plate (ground) and possibly cause an environmental disaster. Moreover, control of the injected gas that might leak in the wider area around the drilling site can also be important. The controllable spooling tethered-underwater-vehicle-carrier buoy system could monitor the area for any leakage or excess pressure on the seabed surface in order to give feedback to the drilling's controllers, to slow down or adjust the injected gas's flow into the wellhead and canals.

A spooling tethered-underwater-vehicle-carrier buoy system is able to patrol on the surface and under the water at the same time for any spill and leakage of pollutant (including the $CO_2$ extracts to the ocean due to the oil company's seabed activities), check on the health of the various underwater assets and report any leakage or breakage, in order to react in a timely manner to minimize the effect of any such disaster in a timely matter.

In the following, exemplary tasks that various embodiments of the controllable networked buoy system, can carry out to benefit the oil and gas industry are listed (non-exhaustively).

1. Environmental Monitoring: Oceanography, hydrography, situation awareness (reporting tsunamis), albedo, pollutants and anomalies (e.g. Co2), and weather situation.
2. Water and Waste Management: considering the injection of produced water, analyzing the pollutants; facilitate predicting environmental concentrations (PEC) of the pollutants in volume term as a function of various natural phenomena, such as currents, tides, waves, evaporation and biodegradation.
3. Detecting oil slicks on the surface, especially for those slicks that are thin, scattered, or several hours or days have passed from the incident. The oil slicks can become disintegrated into small droplets and mixed with the water and impossible to be observed by remote sensing (airplanes, satellites, etc.).
4. Oceanography, hydrography, situation awareness, weather and the environmental monitoring and survey which could help the oil company crews and personnel, or the structure to be prepared and stay safe (e.g. they might decide to leave an area which could be object to a tsunami or a strong hurricane).
5. Identifying areas with high exploration potential by predicting the distribution of hydrocarbon-bearing reservoirs and detecting the optimal hydrocarbon entrapment zone by surveying temperature. The hydrocarbon-bearing reservoirs have noticeably higher temperature compared to the areas with no oil or gas. The temperature in hydrocarbon-bearing reservoirs can be, for example, between 60 and 120° C. Therefore, by integrating a simple temperature sensor inside the buoy and its TUV and surveying temperature of various areas in the seabed, the areas with high potential hydrocarbon-bearing reservoirs can be detected.
6. Identifying areas with high exploration potential by predicting the distribution of hydrocarbon-bearing reservoirs and detecting the optimal hydrocarbon entrapment zone by surveying the maturity of the rocks (which geological period they are belonged to), tectonic changes, and net erosion. The buoy and its TUV with simple imagers (e.g. optic, radar, sonar, infrared), and sensors the buoy will be able to survey the basin and rocks in the seabed and provide those information mentioned above to the oil and gas experts and computers for further analysis. The monitoring, positioning, navigation, and relaying communication capabilities of the controllable networked buoy system can also be used for the search and rescue monitoring system.
7. The controllable networked buoy system is able to provide a cost and energy effective relaying communication infrastructure and navigation systems for the oil and gas marine transportation (e.g. vessels), on the surface or under the water oil ridges and seabed structures, other buoys and instruments and personnel.
8. The controllable networked buoys could use sensors to measure the gravity (similar to what is done by GRACE spacecraft or several oil companies) to measure and survey the amount that the seafloor of the oil and gas fields gets compacted and declines. The information could be used as a feedback to adjust the drilling activities and locations in the field.

Various example embodiments of the controllable networked buoys systems of the present disclosure can be equipped with camera, sonars, active and passive sensors to monitor the health of the assets under the water (e.g. pipelines) and report any leakage or defect. In some embodiments, the tethered-vehicles can be used as transponders which exploit their fast wired communication with the buoys to acknowledge and facilitate positioning under the water.

In some embodiments, the mother-buoys and the TUVs can be used to map the topography of the water (e.g. the currents and the waves, depth of the water, etc.), as well as measure different parameters such as hydrographical, oceanographical (physical such as temperature, pressure, flux, albedo, etc.) and chemical (salinity, OCO, etc.), or near the surface information such as the pressure, temperature, radiation fluxes (UV), albedo, cloud coverage, etc.

Some example instruments, sensors, modems, avionics, imagers, detectors that could be integrated inside the buoy (100) are provided in Table 1.

TABLE 1

| Science and task parameter | Electronics and Sensors (their references) | Sensitivity and specification |
|---|---|---|
| Wind on the Surface | Hair-based sensors for micro-autonomous systems (wims2.org/publications/papers/sadeghinajafiprocspieapril2012.pf) | 2 cm/s and dynamic range of more than 15 m/s<br>3.5 mW<br>1.5 g |
| Temperature | Ultra-Small, Low Power Digital Temperature Sensors TSYS02 (www.meas-spec.com/temperature-sensors/digital-temperature-sensors/digital-temperature-sensors.aspx) | $-40°$ C. to $+125°$ C.<br>High Accuracy up to $\pm0.1°$ C.<br>2.5 mm × 2.5 mm<br>0.045 mW |
| Pressure | MEMS pressure sensor: LPS331AP (www.st.com/web/catalog/sense_power/FM89/SC1316/PF25160) | 260 to 1260 mbar absolute pressure range<br>High-resolution mode: 0.020 mbar RMS<br>0.02-0.09 mW<br>$\sim 3 \times 3 \times 1$ mm |
| Pyranometer (Albedometer) | CS300-L Pyranometer (www.campbellsci.com/cs300-pyranometer) | Light Spectrum Waveband: 300 to 1100 nm<br>Measurement Range: 0 to 2000 W m$^{-2}$ (full sunlight $\approx 1000$ W m$^{-2}$)<br>Sensitivity: 0.005 kW m$^{-2}$ mV$^{-1}$<br>Weight: 65 g |
| Snow and water depth | SR50A acoustic sensor (www.campbellsci.com/sr50a-overview) | Measurement Range: 0.5 to 10 m<br>Resolution: 0.25 mm<br>Power 2.25-4.5 W<br>Weight: 1 kg (needs to get customized) |
| Humidity | Libelium Humidity Sensor - 808H5V5 | Measurement Range: 0~100% RH<br>Operating temperature: $-40$~$+85°$ C.<br>2.5 mW<br>few grams |
| Magnetic Forces | MEMS Magnetometer: STMicroelectronics Launches Single-Chip Magnetometer (www.st.com/web/en/press/p3339) | Measurement Range: $\pm 4/\pm 8/\pm 12/\pm 16$ gauss<br>$-40°$ C. to $+85°$ C.<br>power: 150 mW-250 mW<br>Weight: 3 grams |
| Optic Images | CMOS ultra-compact cameras OV9665 (www.ovt.com/products/sensor.php?id=5) | 4.5 × 5 mm<br>80 mW<br>Resolution: 1 MP |
| Spectrometry | USB2000 Miniature Fiber Optic Spectrometer (www.oceanoptics.com/Products/usb2000.asp) | 89.1 mm × 63.3 mm × 34.4 mm<br>1.25 W |
| Mass Spectrometry (Granularity) | Miniature Mass Spectrometer | Power: 30 mW<br>Mass: 0.3 g<br>Size: 0.27 cm$^3$ |
| Inertial Measurement Unit | MEMS Inertial Measurement Unit (IMU consisting of 3-axis gyro, accelerometer, and magnetometer) IMU-3000 Triple Axis Motion Processor ™ Gyroscope | Weighs: 3 grams<br>Power: 150 mW-250 mW<br>4 × 4 × 0.9 mm |

TABLE 1-continued

| Science and task parameter | Electronics and Sensors (their references) | Sensitivity and specification |
|---|---|---|
| Molecular Oxygen (O2) | Libelium's Molecular Oxygen (O2) Sensor - SK-25 | Measurement range: 0~30%<br>0.088 mW<br>Operating temperature: 5~+40. C.<br><10 g |
| Nitrogen Dioxide (NO2) | Libelium's Nitrogen Dioxide (NO2) Sensor - MiCS-2710 | Measurement range: 0.05~5 ppm<br>Sensitivity: 6~100<br>Operating temperature: −30~+85. C.<br>5 mW<br><10 g |
| Ammonia (NH3) | Libelium's Ammonia (NH3) sensor - TGS2444 | Gases: NH3, H2S<br>Measurement range: 10~100 ppm<br>Sensitivity: 0.063~0.63<br>Operating temperature: −10~+50. C.<br>6 mW<br><10 g |
| Methane (CH4) | Libelium's Methane (CH4) sensor - TGS2611 | Gases: CH4, H2<br>Measurement range: 500~10000 ppm<br>Sensitivity: 0.6 ± 0.06<br>Operating temperature: −10~+40. C.<br>35 mW |
| Liquefied Petroleum Gas | Libelium's Liquefied Petroleum Gas Sensor - TGS2610<br>few grams | Gases: CH3CH2OH, CH4, C4H10, H2<br>Measurement range: 500~10000 ppm<br>Sensitivity: 0.56 ± 0.06<br>Operating temperature: −10~+40. C.<br>35 mW |
| Carbon Monoxide (CO) | Libelium's Carbon Monoxide (CO) Sensor - TGS2442<br>few grams | Measurement range: 30~1000 ppm<br>Sensitivity: 0.13~0.31<br>Operating temperature: −10~+50. C.<br>1.5 mW |
| Solvent Vapors | Libelium's Solvent Vapors Sensor - TGS2620<br>few grams | CH3CH2OH, H2, C4H10, CO, CH4<br>Measurement range: 50~5000 ppm<br>Sensitivity: 0.3~0.5<br>Operating temperature: −10~+40. C.<br>250 mW |
| Ozone (O3) | Libelium's Ozone (O3) Sensor - MiCS-2610<br>few grams | Measurement range: 10~1000 ppb<br>Sensitivity: 2~4<br>Operating temperature: −30~+85. C.<br>68 mW |
| Ice detector | Ice*Meister Model 9732-OEM ice detecting transducer probe (www.controldevices.net/Defence/New%20Avionics/PDF/9732%20DATA%20SHEET.pdf) | 0.33 mW<br>−50° C. to +50° C. |
| Iridium Interface Board | 205102 Iridium 9523 Interface<br>acomms.whoi.edu/micro-modem/iridium-interface board/ | Iridium interface board with 9523 Iridium module, u-blox MAX-7Q-0 GPS module, Atemel SAM3S4CA-AU microprocessor and Actel AGLN250V2-VQG100 FPGA on a Micromodem sized form factor such that it can be mounted on the Micromodem stack in certain applications. On board microprocessor allows for custom applications to interface between the Micromodem or other sensors |
| Transducers, Arrays and Towfish | WH-BT-1 Single Ring 28 kHz<br>And others at<br>acomms.whoi.edu/micro-modem/transducers-arrays-and-towfish/ | |
| Modem Mainboard | Micromodem 1.3c DSP<br>And others at:<br>acomms.whoi.edu/micro-modem/modem-mainboard/ | |

TABLE 1-continued

| Science and task parameter | Electronics and Sensors (their references) | Sensitivity and specification |
| --- | --- | --- |
| Precision Time and Position Board | 205103 Precision Time and Position Board and others at acomms.whoi.edu/micro-modem/precision-time-and-position-board/ | Microsemi SA.45s CSAC module, u-blox NEO-6T-0 GPS module, Atemel SAM3X8EA-AU microprocessor and Actel AGLN250V2-VQG100 FPGA on a Micromodem sized form factor such that it can be mounted on the Micromodem stack in certain applications. On board microprocessor allows for custom applications to interface between the Micromodem or other sensors. |
| Several sensors and electronics mentioned in the U.S. Pat. No. 8,912,892 | All the sensors (to detect oil and gas leaks, radiations, environmental sensors, etc.), modems, batteries, processors, controllers, avionics, antenna, memories and data loggers, energy harvesting devices, devices and materials to clean up the oil spills, materials, etc. suggested in the US Patent U.S. Pat. No. 8,912,892 [23] could also be used for this disclosure and to be integrated inside the controllable buoy (100) as well | |
| acoustic modem | WHOI's Micro-Modem [34] Texas Instruments ™ TMS320C5416 DSP | |
| Several micro sensors and electronics for planetary and Earth applications | Several JPL Micro Devices Laboratory's sensors and electronics for Earth and Planetary deployments could be found at: microdevices.jpl.nasa.gov/capabilities | |
| Lighter autonomous underwater vehicles | REMUS 100 www.km.kongsberg.com/ks/web/nokbg0240.nsf/AllWeb/ D241A2C835DF40B0C12574AB003EA6AB?OpenDocument Or Slocum Glider: http://www.webbresearch.com/slocumglider.aspx | REMUS—Remote Environmental Measuring UnitS 100 is a compact, light-weight, Autonomous Underwater Vehicle - AUV designed for operation in coastal environments up to 100 meters in depth Slocum Glider: www.webbresearch.com/pdf/ Slocum_Glider_Data_Sheet.pdf |
| Several sensors, electronics, solar cells, avionics, controllers, batteries, data loggers, etc. from Libelium.com and its Waspmote products | Several sensors, imagers (infrared, optical, etc.), ice and water detectors, solar cells, avionics, controllers, batteries, data loggers, peer to peer wireless RF modems, memories, and other electronics from Waspmote product of Libelium.com can be integrated and used in the controllable buoy (100) (both the mother-buoy and its TUV) www.libelium.com/products/waspmote/ | |
| Wind turbine to generate power | WindWalker M SUPER LOW wind turbine 48 DC 100 watts in breeze 750 watt max LOW or WINDWALKER 250 www.freespiritenergy.com/products.html | WindWalker M SUPER LOW wind turbine 48 DC 100 watts in breeze 750 watt max LOW |
| Underwater Optical Communications | www.qinetiq-na.com/products/pscs/ underwater-optical-communications/ | www.qinetiq-na.com/wp-content/uploads/ data-sheet_underwater-optical-communications.pdf |
| Robotic parts and tools: For example JPL's Microspine Grippers | JPL's Microspine Grippers: Foot Mechanisms for Anchoring and Mobility in Microgravity and Extreme Terrain robotics.jpl.nasa.gov/tasks/ taskVideo.cfm?TaskID=206&tdaID=700015&Video=147 | JPL's Microspine Grippers could be integrated to the structure of some example embodiment buoys in this disclosure, or the buoys introduced in U.S. Pat. No. 8,912,892 to keep the buoy grasp in a location on the hard terrains or on the seafloor. |

Ice—Water Buoys:

The controllable buoy's structure can be customized such that it could be used both on the hard surface (for example, ice in the polar regions) and on the surface of the water. This is especially useful when the system is used in the Arctic or Polar Regions when there are areas covered by water as well as ice near each other. Therefore, the buoy can move around on hard surfaces (e.g., ice) by wind or on the surface of the water. For example, the buoy can move in ice using internal control mechanical system, as described in the U.S. Pat. No. 8,912,892 referenced above.

Buoy Network

The buoys can be deployed over a vast area in the ocean. In some embodiments, the buoys can autonomously distribute themselves uniformly such that a majority of them is located at the bottom of the deep sea for a long time, while a few of them are deployed at the surface, employing camouflage techniques in order to remain concealed. The buoys can be designed to be ecology friendly, long-lived, and controllable and can exploit natural resources in the sea environment for their locomotion, part of their communication, and energy harvesting. The buoys on the surface can exploit strong winds and currents, and sun for their locomotion and energy harvesting. They can have a peer-to-peer RF and acoustic communication with the other buoys on the surface and in deep sea underwater. The buoys could also have communication with the orbiter and the ships, airplanes, and submarines missioned in the area. The buoys can control their wind-driven locomotion by letting water inside the large cavity in them and submerge into the water, which is at least 30 times slower, and with a velocity angle caused by the Ekman Spiral (as discussed above and in Ref. [1]), in order to slow down and not to exit an area of interest. The buoys can opportunistically wait for the desired wind direction in order to resume their wind-driven motion by emptying their internal water and controlling their buoyancy. The buoys can also use different mechanical and actuators in order to initiate locomotion and control their location.

The buoys can also have acoustic communication capabilities, which would allow them to exchange messages to other buoys and entities in the water when necessary. They can use very low frequency signals (VLF) (for example, acoustic signals), in order to trigger a sleeping node very deep in the ocean. The buoys can be large, therefore they can provide large directed antennas which could be used in order to send signals, even signals as brief as triggering a triggering signal to assets down in the deep sea. This is possible because the location of the specific sleeping nodes that need to be contacted can be almost precisely known, and, due to the controllable distributed nature of the buoys on the surface, these buoys can collaboratively use phase-array techniques to send a powerful signal directly to the sleeping nodes that need to be woken up. This strategy not only makes sending the VLF communication signal to the deep ocean possible but since the signal energy is confined to a particular direction, makes the triggering signal more concealed and less susceptible to interception. The buoys could thus facilitate communication and energy harvesting for any fixed sleeping nodes containing payloads that might have been placed for years in the bottom of the deep ocean. The buoys are able to "learn" different layers and distances under the water, which will be used to help and guide any riser buoy that needs to be at a specific location on the surface, or under the sea reliably and quickly. The buoy can be a payload itself.

Furthermore, the buoys can be concealed using various camouflage techniques and can keep the acoustic communications to a minimum, since acoustic communications are more prone to be detected by intruders. Moreover, the buoys can be equipped with different sensors and detectors such as vibration, radar, passive sonars, as described in Ref. [1], in order to be aware of the surrounding situation. If a hazardous or suspicious event happens, the buoys can react (using their control system's strategy to get away from the hazardous event) in order to be safe or, as a last resort, self-destruct.

Buoys on the surface can use distributed phase-array techniques to focus the energy of their command and triggering signals in the direction of the target buoys on the bottom of the sea. Sleeping buoys can periodically rise to the surface to use GPS signals to determine their location. When the buoys submerge themselves back into the sea they can do so in such a manner as to make their descent as vertical as possible. This ensures that their location at the bottom of the sea will be as close as possible to the GPS-measured location on the surface. Such near vertical descent can be possible using accelerometers and the fact that there is very little water current once the buoy is sufficiently deep. When the buoys determine their location on the surface, immediately prior to their submersion and vertical descent, they can transmit their location to neighboring buoys, as a result of which the system can have a fairly reliable estimate of the buoy's final resting location at the sea floor. The buoys can also periodically resurface to replenish their energy storing batteries, in some embodiments where solar energy is employed. In fact, the buoys can use energy harvesting techniques such as those described for the buoys with TUVs in the present disclosure. For example, the buoys may have a transparent upper dome with a solar array underneath the dome. Similarly, techniques and structures described with reference to the buoys may also be applied in some embodiments of the buoys.

In some embodiments, buoys can have a flexible communication system capable of supporting several distinct communication requirements, comprising for example: (i) between buoys that are on ocean's surface, (ii) asynchronous wake-up signal sent to sleeping buoys on ocean bed in order to activate them under latency constraints, (iii) between buoys on the surface and external entities such as a ship, and (iv) between proximate submerged buoys on the ocean bed. To meet these requirements, in some embodiments it is possible to combine radio-frequency (RF) wireless for above surface and acoustic wireless underwater. Given the depth requirements of a few thousand meters and energy and size constraints, acoustic can be used for underwater communication needs.

Buoys on the surface can self-organize into a multi-hop network, communicating with each other via RF in the UHF band. Therefore, a message from a buoy can hop through intermediate buoys to reach a target location. In some embodiments, with precise knowledge of time and location through GPS, and the use of steerable antennas the surface-to-surface communication can be long range and energy efficient. For example, off-the-shelf 20 dBm Zigbee radios with directional antennas are able to achieve 100 Kbps at 10 s of km. Waking up of the buoys on the ocean floor can be done acoustically. To perform this, in some embodiments the surface buoys can cooperate via RF networking to perform distributed acoustic beamforming. Normally, beamforming is carried out using fixed arrays. However, distributed beamforming is also possible and applicable to the buoys of the present disclosure. With distributed acoustic beamforming, the surface buoys can cooperatively direct acoustic wake-up signals towards the specific locations on the ocean bed where sleeping buoys are located. The signal-to-noise (SNR) gains from beamforming can be further enhanced by using codes, together providing a long-range wake-up capability at many kilometers. The submerged buoys can be duty-cycled with a very low ratio so as to minimize power consumption, and use a preamble-sampling approach (similar to that used in low-power RF sensor networks) to wake-up when the acoustic wake-up signal is sent to them.

In some embodiments, the buoy's autonomy in terms of communication time with its peers can be important since that exchange of information constitutes the basic link unifying the mobile mesh network. In some embodiments, the expected energy scavenging level per day is about 30,000-40,000 Joules, and the maximum power consumption of the transceiver in each buoy can be designed to be less than 100 mW, which is equivalent to more than 100 hours of consecutive peer-to-peer communication. In order to increase the communication distance with a reasonable data rate, quadrature phase shift keying (QPSK) can be used as a modulation technique for both uplink and downlink communication. QPSK provides a spectrum efficiency of about 1.6 bits/Hz and requires a SNR of at least 14 dB for a bit-error-rate (BER) of at most 10-6. In order to maximize the propagation distance given an antenna size of less than 10 cm (which can be smaller than the diameter of a buoy), the 433 to 434 MHz frequency band available for ISM applications can be the most suitable ones. Based on this selection, the link budget can be calculated. In some embodiments, the maximum communication distance is estimated to be 100 km with a maximum date rate of 320 kb/s. An exemplary expected number of buoys can be of the order of 1000 for a global coverage exceeding 10M km$^2$. However, this exemplary number may be increased to increase the overall robustness of the system when considering possible buoy failures in the field due to rare but extreme environmental conditions such as extreme winds or solar storms.

In some embodiments, the majority of the buoys could be distributed at the bottom of the sea sleeping, where carrying out minimum activities such as reporting their status (e.g. available power, health of their electronics) using acoustic communication when they are asked to. A smaller number of buoys could be on or near the surface of the sea. The sleeping buoys can periodically ascend to the surface using either self-powered hydrogen fueled artificial muscle or other low-powered actuators. The ascending buoy can decide to rise-up based on the time that has elapsed since its most recent sleep or its most recent reception of any outside signal, the level of its batteries, the topology and the concentration of the other sleeping buoys in its proximity, and the priority ranking of the region where it sleeps. The ascending buoy can exchange acoustic signals with the buoys in the range of its proximity while ascending, in order to gather information regarding their location, the topology and the health status (e.g. if the signal transceivers work fine, available power, etc.). When the ascending buoy reaches the surface, it can empty the water inside its inner cavity in order to increase its buoyancy, and better to be able to exploit wind- and current-driven motion. The buoy could also join the controllable and dynamic wireless mesh network of the buoys on the surface. The buoy could also transfer any information gathered from the deep down sleeping nodes to the network. The information can be fused to those of the rest of the buoys on the surface providing a collective topology and status of the entire buoy network (on the surface and deep at the bottom of the sea), which can be used by the distributed control architecture of the buoy network. The distributed control architecture can intelligently distribute tasks and positions among the buoys in the network in order to optimize the coverage of the area, the resources (e.g., memory, power, bandwidth), and the performance of the entire system (e.g., how soon a random sleeping buoy could awaken). The ascended buoy can stay on the surface for a time in order to recharge its batteries (using its solar cells and other techniques), updating and upgrading its software (e.g. its decoy codes might be outdated while it was sleeping underwater) and become part of the surveillance and monitoring system on the surface. The distributed control architecture of the buoys network can use the topology map, the health status, and the resources of the buoys on the surface and those at the bottom of the sea to decide where it should leave a specific buoy on the surface submerge in the water at the specific location, in order to organize a uniform distribution of the buoys and their available resources, on the surface and at the bottom of the sea. When an invoking event happens, for example a requirement that a certain number of buoys are deployed in a specific location, the command can be sent to any of the buoys on the surface. The Distributed Control Architecture (DCA) for the buoys network can notify those leading buoys on the surface, which will be able to send the acoustic signals used to awaken the sleeping buoy nodes. If the sleeping buoys are acoustically reachable, they can be awakened right away and can acknowledge the leading buoys either by sending an acoustic signal or by their actual upward motion, which could be detected by the leading buoys and would confirm that the sleeping buoys have been awakened. The awakened buoys can use their strong actuators and their emergency power in order to rise all the way up to the surface or perhaps a location inside the sea where they are missioned.

A global controller, which can be a pre-defined buoy, a buoy selected by the network according to a set of rules, or a non-buoy vehicle or satellite, can be in charge of controlling the optimum distribution of groups of buoys for all sub regions. This optimization can take in account, for example, the following variables that are evaluated for each sub region: (i) the number of buoys, (ii) the total amount of memory available, (iii) each buoys' energy reserve, (iv) the bandwidth available, (v) the energy that can be harvested based on the sub region local conditions, e.g. wind intensity, and (vi) the sub region's priority.

The number of buoys entering, leaving, or staying in a sub-region can be governed by the resulting distribution of the global controller's optimization process which is performed at regular time intervals. The instructions can be sent to each buoy via the satellite communication and/or through existing ground stations using the buoy peer-to-peer communication link if available.

In addition to receiving centralized commands, the buoys within each sub region can negotiate with each other to share tasks and optimize the use of local system resources. The buoys in each grid can further negotiate with each other to decide if they should allow an outside buoy to join them in the sub region grid or just pass by. They may also let an insider buoy leaves the grid for a neighboring grid. Finally, it is the responsibility of the buoy's own controller to either keep its position stable within a sub region or move to a new designated one. In both cases the buoy can determine by itself which winds to follow and when to stop and wait for other buoys that will agree with its instructions.

For example, a distributed coordination approach based on a "probabilistic swarm guidance" methodology can be carried out, as described in Ref. [42]. In some embodiments, the domain of coverage is split into sub-regions, or cells. The global controller can periodically determine the optimal desired buoy distribution over the cells based on available data. Then the desired distribution can be communicated to each buoy. Each buoy can now act semi-independently (it can negotiate with its neighbors to avoid local conflicts) in such a way that the desired distribution will be achieved. In its simplest form, the probabilistic guidance approach as described in Refs. [42]-[44] can be decentralized and not require communication or collaboration between buoys. In addition to being decentralized, the probabilistic guidance approach can have an autonomous self-repair property: once the desired swarm density distribution is attained, the buoys automatically repair damage to the distribution with minimal or no collaboration and without explicit knowledge that damage has occurred. The global controller intervenes as it produces an update on the desired target distribution. Buoy control using local wind fields fits this process well since it provides the statistical variation needed in motion for this algorithm to function properly.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 3 also illustrates the way the tethered underwater vehicles can check on the health of the underwater or sea-bed instruments or perform communication with them.

DETAILED DESCRIPTION

Figure 1A:
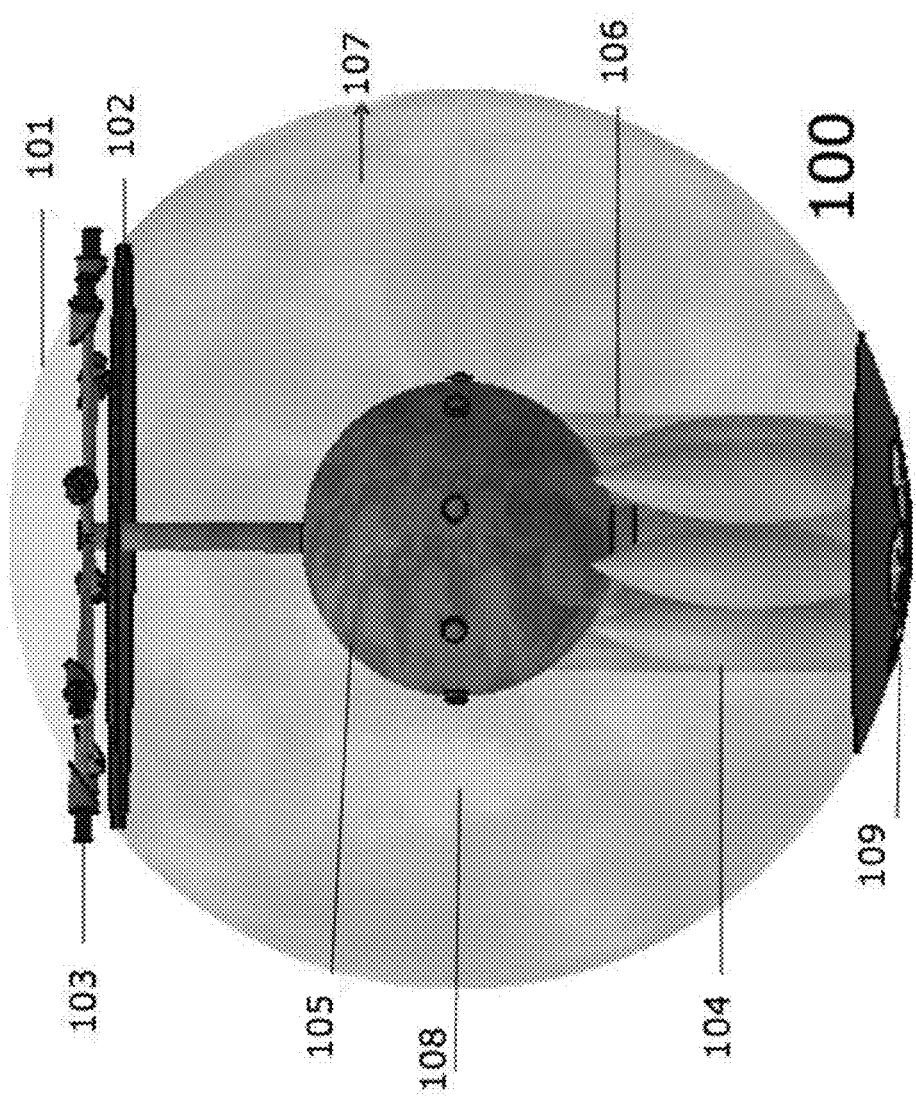
FIG. 1A illustrates an example of a controllable buoy of the present disclosure.
Figures 1B, 1C:
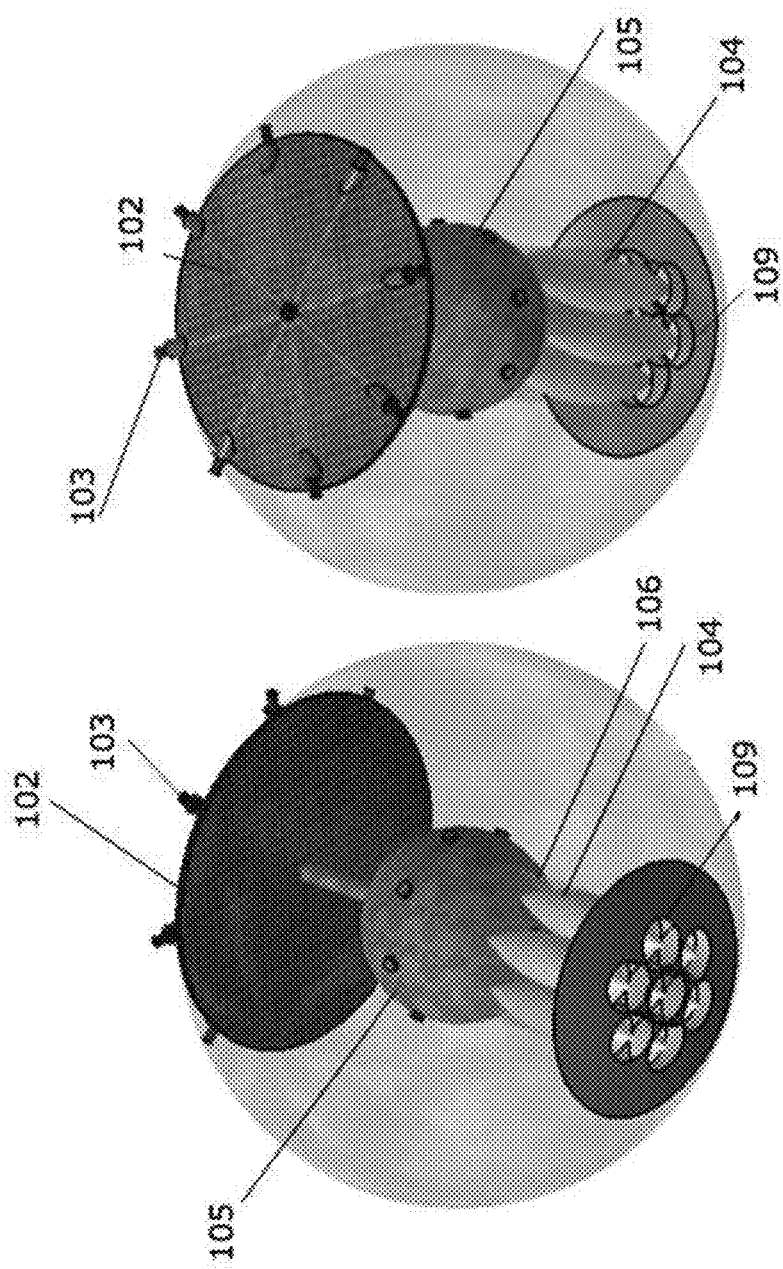
FIG. 1B illustrates a bottom view of the exemplary buoy of FIG. 1A with multiple attached tethered underwater vehicles.
FIG. 1C illustrates a top view of the exemplary buoy of FIG. 1A with multiple attached tethered underwater vehicles.

For the above, and other, applications, the present disclosure describes controllable buoys with optional attached TUVs. FIGS. 1A-1C illustrate an example of a buoy (100) with one or more TUVs (104). The controllable buoy (100) can be of any shape, in this embodiment spherical. The buoy (100) can be sized appropriately for the use, for example 1 to 3 meter.

There is a cavity (108) inside the buoy (100) which can be filled with air. There is a separate chamber (101) creating a positive buoyancy, separated from the cavity (108) by a panel (102). The outer layer of the buoy (107) can be made of flexible materials or elastomer foams, such as ETFE (Ethylene tetrafluoroethylene), or aerogels foams. Metallic microlattices could be laminated between the layers of the ETFE, or other polyurethane foams, in order to make the outer layer (107) light so that it can take advantage of the winds and surface water-currents for mobility. There can be printed circuits, sensors, antennae, micro modems, micro imagers, micro spectrometers, etc., incorporated in the structure of the buoy (100) and printed on polyimide film and laminated between the layers of the outer layer (107). The materials used for the outer layers of the buoy (100) and the TUVs (104) can be appropriate for marine environments: for example, no algae should be able attach to them. ETFE, polyurea, etc., are appropriate choices of materials for this very reason. A biofouling or anti-stick coating can also be applied.

The TUVs (104) can be held in a special protective container (106) for deployment and retrieval through openings (109) at the bottom of the buoy (100). Two or more fiberglass (or similar material) tubes (106) integrated inside the mother-buoy can hold the TUVs (104) in a stowed position. For example, each TUV may be stowed in one tube. The end of each TUV-stow and launch tube can be connected to the protective chamber while the other end comprises of a circular opening that allows the TUVs to be launched and retrieved inside the mother-buoy.

In some embodiments, a fiberglass protective chamber (105) can encapsulate the control, communication, and the power electronics subsystems inside the buoy. Other or alternative materials could comprise light and sturdy materials such as titanium. The chamber (105) can also allow access between the cavity (108) and the air pump holes (103).

Figure 1D:
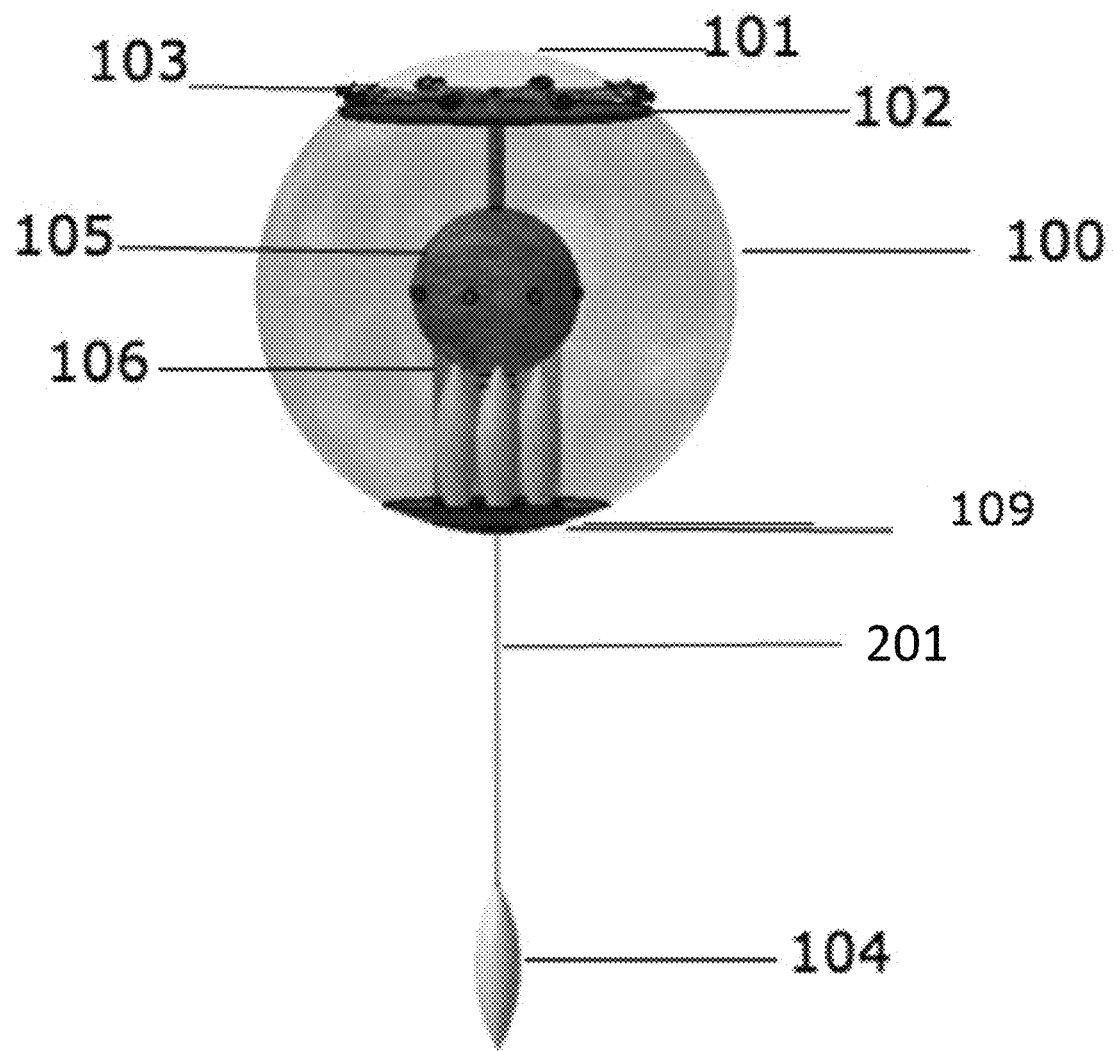
FIG. 1D illustrates an exemplary controllable buoy with a tethered underwater vehicle deployed.

FIG. 1D illustrates an exemplary buoy with multiple TUVs attached, where one of the gliders (104) is deployed while the remaining TUVs are attached inside the buoy (100). On top of the buoy (100), there is a positive buoyancy chamber (101) that can be filled with, for example, air or oil in order to create positive buoyancy that would control how far the buoy can submerge and ensure that the buoy (100) remains in the stable upright position shown in this figure. The buoy can comprise a panel (102) that includes solar arrays that are able to harvest sunlight to generate the electricity needed for the electronics used in the spooling tethered-underwater-vehicle buoy (100). The panel (102) can also be used as an RF antenna for transmitting and receiving signals from the orbiter (190), as shown in FIG. 1A, or as an acoustic antenna when communication needs to be carried out with any instruments that are under the water. In some embodiments, the panel (102) is enclosed within the buoy and is covered by a protective transparent dome on top of the array. For example, the transparent buoyancy chamber (101) also serves the function of protecting the panel (102). In some embodiments, an array of cameras and sensors are available on the buoy (100). The positive buoyancy chamber (101) can be made of flexible materials such as ETFE. A hydrophone can be used in the center of the positive buoyancy chamber (101) and could be coupled with any source of low frequency acoustic signals sent by any buoy, or instrument deeper in the ocean, and sent to the controllable spooling tethered-underwater-vehicle buoy (100). In this way, the flexible membrane of the positive buoyancy chamber (101) can resonate with the received low frequency signal as described for example in US Patent No. 2003/0055359, the disclosure of which is incorporated herein by reference in its entirety.

One or more underwater-vehicles (104) could be carried by the controllable spooling tethered-underwater-vehicle buoy (100). The underwater-vehicles (104) could be any state-of-the-art sounders, micro-submarines, gliders, jellyfish robots, or any other AUVs or underwater robots or instruments. As shown in FIG. 1D, the underwater-vehicle (104) is connected to the spooling tethered-underwater-vehicle buoy (100) via a cord (170). The cord (170) can transfer communication signals, and in some embodiments also power, directly between the spooling tethered-underwater-vehicle buoy (100) and the underwater-vehicle (104).

The cord (201) can be tethered around reels inside the chamber in the center of the buoy (105). The central chamber (105) can also contain and protect sensors or electronics such as modems, batteries, etc. The cords (201) could be made of light but strong materials such as carbon fibers that could transfer signals and electricity. The reels and the central chamber (105) could be made out of carbon fibers, proper polyurethanes or ETFE, covered by polyurea coating in order to make them strong and light. The underwater-vehicles (104) can be tethered down into the water, through a special opening (109) in the buoy, using the reel and controllers inside the central chamber (105). The underwater-vehicles (104) can be made of pressure resistant materials and structures in order to be able to dive deeper in the water where the ambient pressure is high. For example, the TUVs could be fabricated with pressure resistant and flexible structures such as ETFE. There could be circuits, sensors, antenna, micro modems, micro imagers, micro spectrometers, etc., printed on Kapton™ and laminated between the layers of the ETFE in the structure of the underwater-vehicle (104).

The tethered underwater-vehicles (104) can be reeled up into their special protective container (106). Furthermore, the imagers and sensors (103) in the buoy (100) can be drawn inside the tubes and inside the chamber (101) in order to remain protected. Therefore, the controllable spooling tethered-underwater-vehicle buoy (100) can roll freely with the wind or surface water-currents, or with the wind on ice surface when the buoy (100) is deployed in partially frozen areas such as the Arctic (or in any other area that is a combination of hard surface and water, such as on Titan or in Greenland in the summer time, etc.).

In some embodiments, a cavity (108) inside the spooling tethered-underwater-vehicle buoy (100), such as in FIG. 1B, can be either inflated or deflated. For example, the cavity (108) could be filled with air and inflated using an air pump that could be integrated in the structure of the buoy (100)—for example, in (103).

Figure 1E:
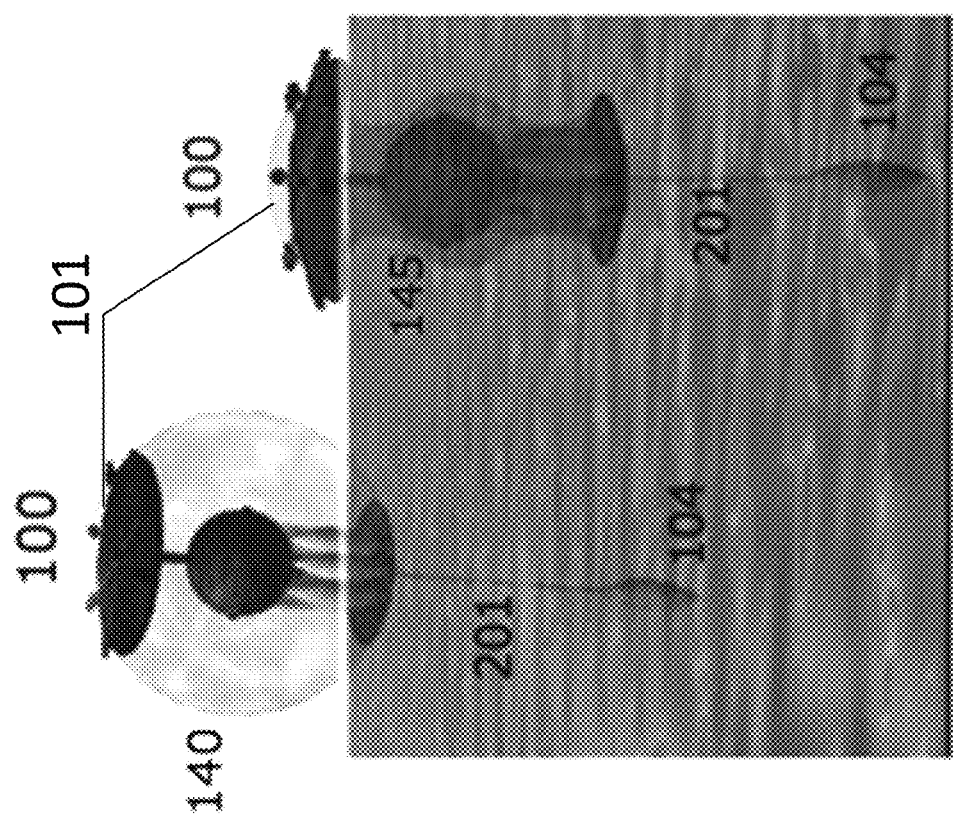
FIGS. 1E and 1F illustrate an example controllable buoy in inflated and deflated states.

FIG. 1E illustrates an example of an inflated buoy (140) and a deflated buoy (145). When the spooling tethered-underwater-vehicle buoy (100) is inflated (140) its body is on the surface and projected to the wind and currents on the surface. Therefore, the buoy can move around at great speed. On the other hand, when the cavity (108) is deflated, for example by emptying the air in the cavity using an air pump, the buoy (100) is deflated and its density increases making it submerge in the water (145). When the spooling tethered-underwater-vehicle buoy (100) is submerged in the water, its body is less projected to the wind and therefore, its speed decreases.

The mother-buoy (145) could remain submerged until a wind in the desired direction blows and then it could re-inflate itself (140) in order to move in the direction of interest. Moreover, if the wind continuously blows off the shore and in the open-seas this creates an Ekman spiral. In this case, by submerging the controllable buoy (100) even deeper, the Ekman spiral could be used to further slow down the motion of the controllable buoy (100) or make it move in a different direction. The underwater-vehicles (104) in the water can also be used as stabilizers. When the underwater-vehicle (104) is deployed deep in the still layers of water it can act as an in-the-water anchor and can keep the controllable buoy (100) from moving around on the surface. Moreover, the underwater-vehicle (104) can use its hydrofins, propellers, and other controlling devices in order to move the buoy (100) on the surface in the direction of the interest, or to prevent it (100) from moving in an undesired direction.

Figure 1F:
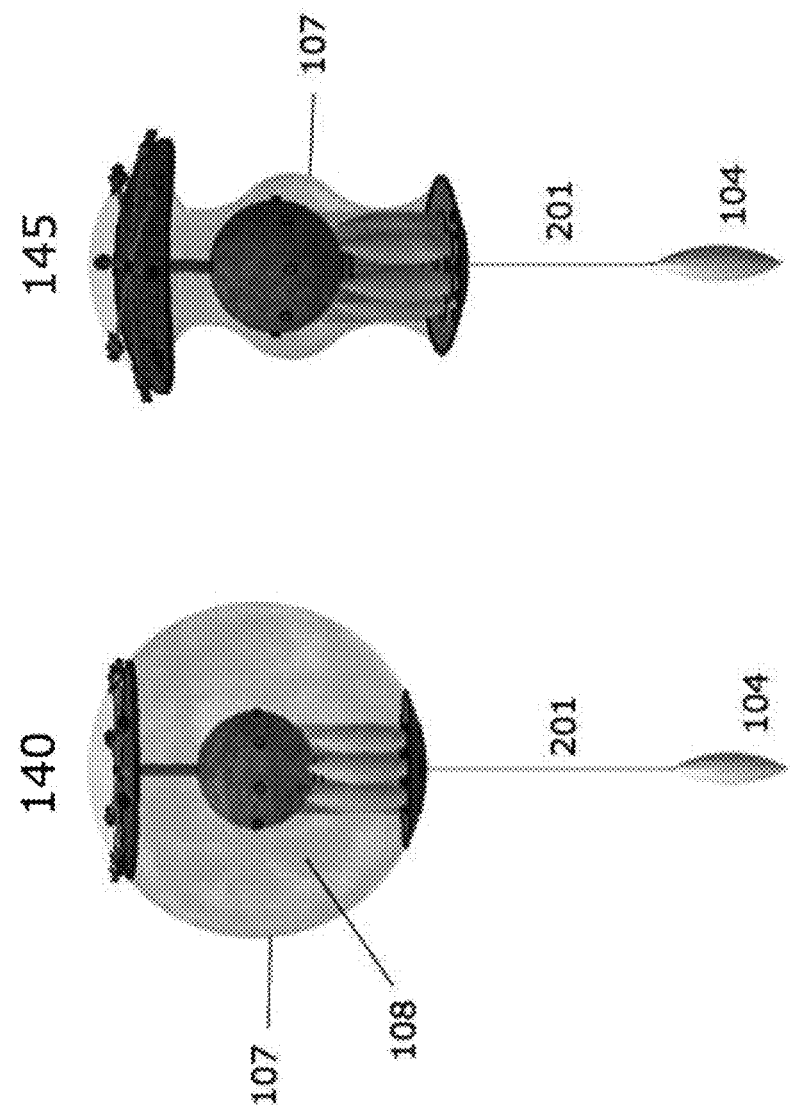

FIG. 1F illustrates an example of inflated (140) and deflated (145) buoy. In some embodiments the controllable buoys can change their form, for example by inflation (140) and deflation (145), in order to adjust their buoyancy and level of submergence, which would result in control of their speed and direction. Additionally, if a buoy is temporarily travelling on ice, it can control its bounciness, hence its motion, by inflation and deflation. Alternatively or in addition, a buoy can alter its buoyancy by taking in and expelling surrounding water in a reservoir within the buoy.

In some embodiments, the tethered underwater-vehicle (104) is connected through a cord (201) (for example made out of carbon nano fibers that can transfer power) or a small bundle of chords (for example a fiber optic communication cable bundled with a high tensile towing chord) to the controllable buoy (100) on the surface. The cord (201) can transfer the communication signals and facilitate communication between the underwater vehicle (104) and the buoy (100) on the surface. The tethered underwater-vehicle (104) can be connected through a cord (201) to the controllable buoy (100) on the surface. Therefore, if an inertial navigation system (INS) comprised of motion sensors (accelerometers) and rotation sensors (gyroscopes) are employed, the location of the tethered underwater-vehicle (104) under the water can be determined using the known techniques of the art.

The tethered underwater-vehicle (104) that is connected through a cord (201) (for example, carbon nano fiber cords that can transfer power) to the controllable buoy (100) on the surface can also transfer power using the known techniques of the art.

Figure 2:
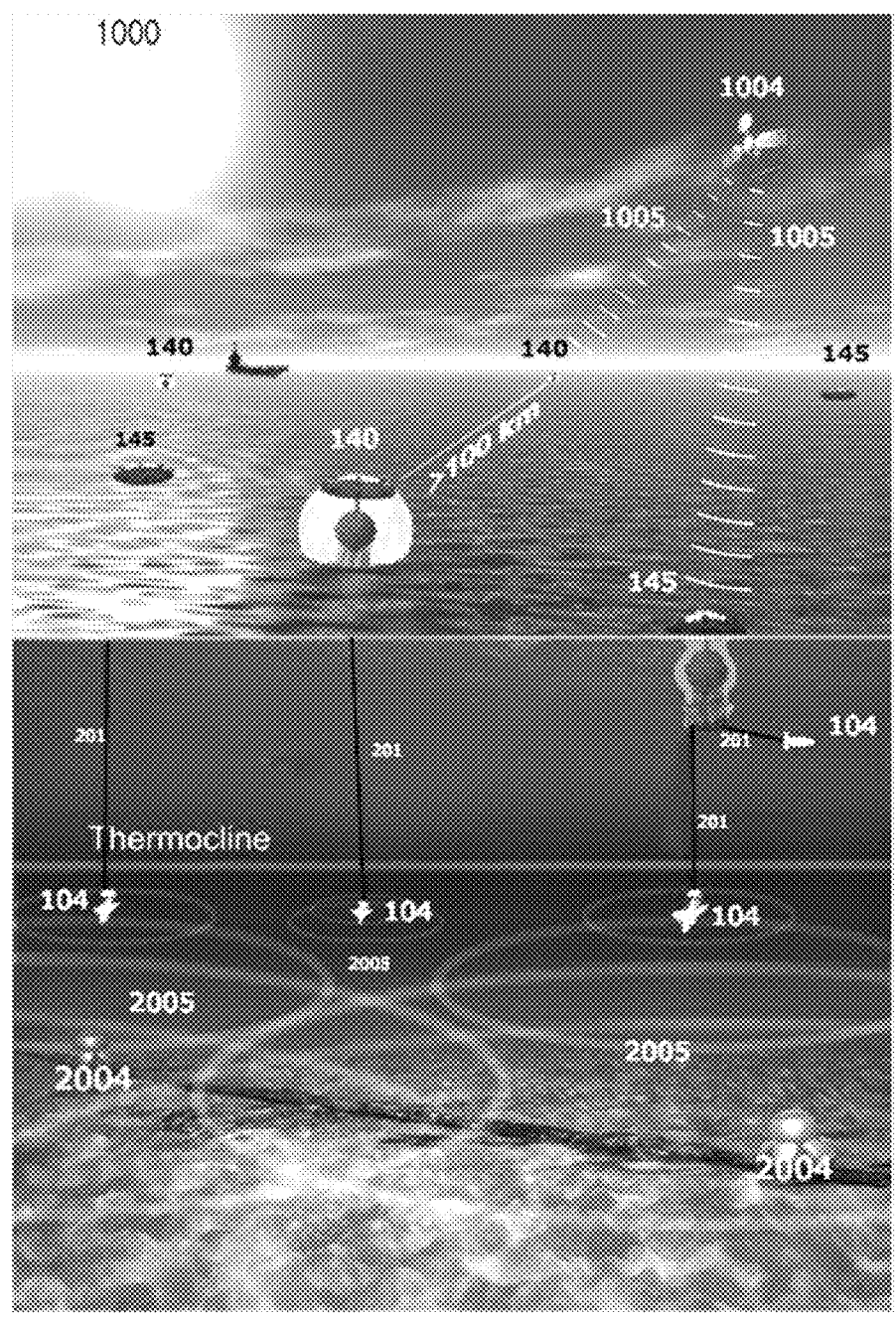
FIG. 2 illustrates an exemplary network of controllable buoys.

FIG. 2 illustrates an exemplary network of spooling tethered-underwater-vehicle-carrier buoys. The mother-buoys on the surface could tether up and down their tethered-underwater-vehicles using their spooling system. When the tethered-underwater-vehicles (104), equipped with acoustic signal modems, dive into the deep water and descend beneath the thermocline layer, they could send broadcasting acoustic signals to the underwater and sea-bed structures and instruments miles away with no distortion, as described in Refs. [11-16]. A mother-buoy on the surface could control its speed and trajectory by adjusting its submergence and by towing from tethered-underwater-vehicles (104). The TUVs (104) can be equipped with a hydrodynamic structure and a propeller. The tethers (201) could carry fiber optic cords in order to transfer optical communication signals between the mother-buoy and its tethered-underwater-vehicles. TUVs from different mother-buoys can communicate to each-other directly by acoustic signaling, or they can communicate through their mother-buoys. For example, with the mother-buoys communicating to each other via RF and the TUVs communicating with their respective mother-buoys via wire, the TUVs can communicate with each-other through a wire-RF-wire network.

The TUVs do not have to wait until they resurface from the deep ocean in order to transfer data to a satellite. The system can transfer data and information from the deepest areas under the water (the TUVs) through the mother-buoy to a satellite in a near-real-time manner.

Mother-buoys could stabilize their movement or stay stationary using their tethered and towing tethered-vehicles and their submergence for motion control. The buoys could also communicate with other buoys through RF communication either in a peer-to-peer manner or through a satellite. The buoys could also collaborate with each other in order to perform acoustic beam-forming, where two or more beams, as visible in FIG. 3 (2005), from two or more buoys converge at a single location (2004) to form a signal through constructive interference. The buoys could also perform collaborative triangulation to locate under water structures, instruments, or areas with diagnosed oil or gas leakage, etc.

Figure 4:
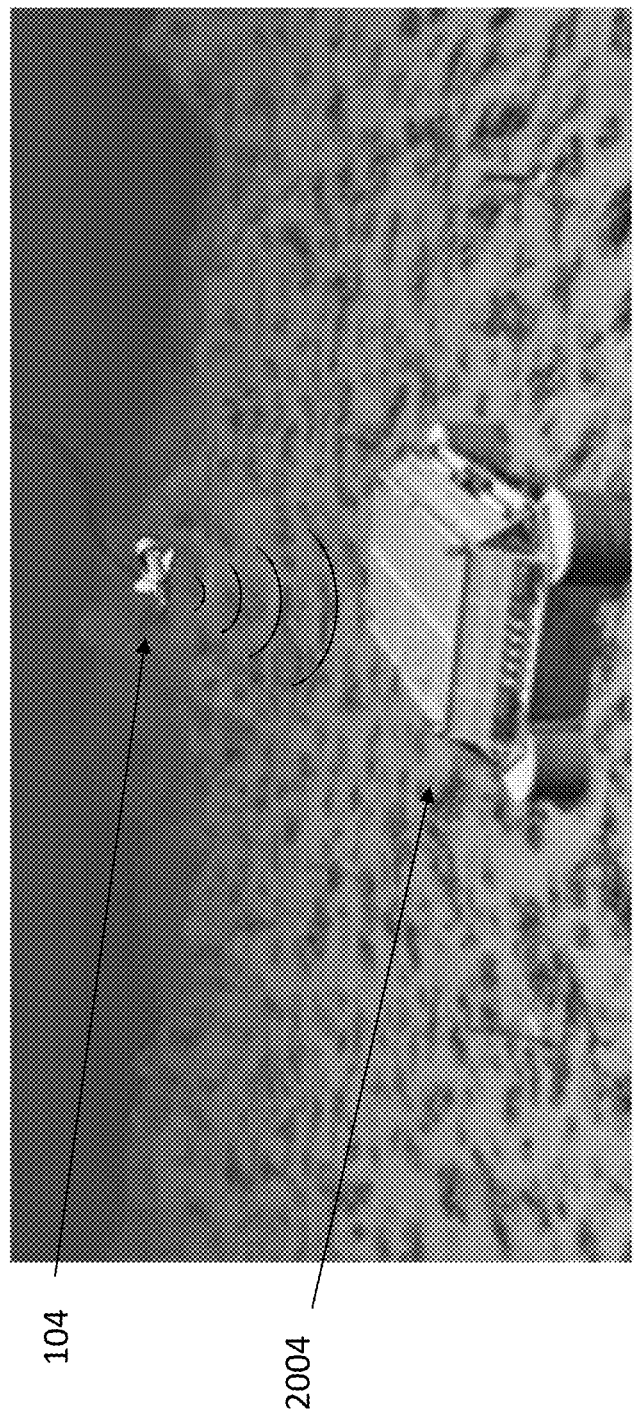
FIG. 4 illustrates an example of a tethered underwater vehicle communicating with an underwater asset.

In addition, the buoys can also give feedback on the leakage of the hazardous materials or land uplifting in the wider area around the drilling site, or feedback on the leakage of the injected gas to the well-head, and the hazardous materials or land uplifting in the wider area around the drilling site. This information can be used in order to control the pressure and the speed of the drilling and steam or water injection to prevent a disastrous event, such as exploding or leakage, etc. The buoys can also facilitate communication from the base station to the assets deep in the water, for example to update the software of the underwater assets. Tethered-underwater-vehicle could recharge the battery of the underwater assets. The TUVs can perform such task using the state of the art induction mechanisms. FIG. 4 illustrates an example of a TUV (104) communicating with an underwater asset (2004).

Figure 5:
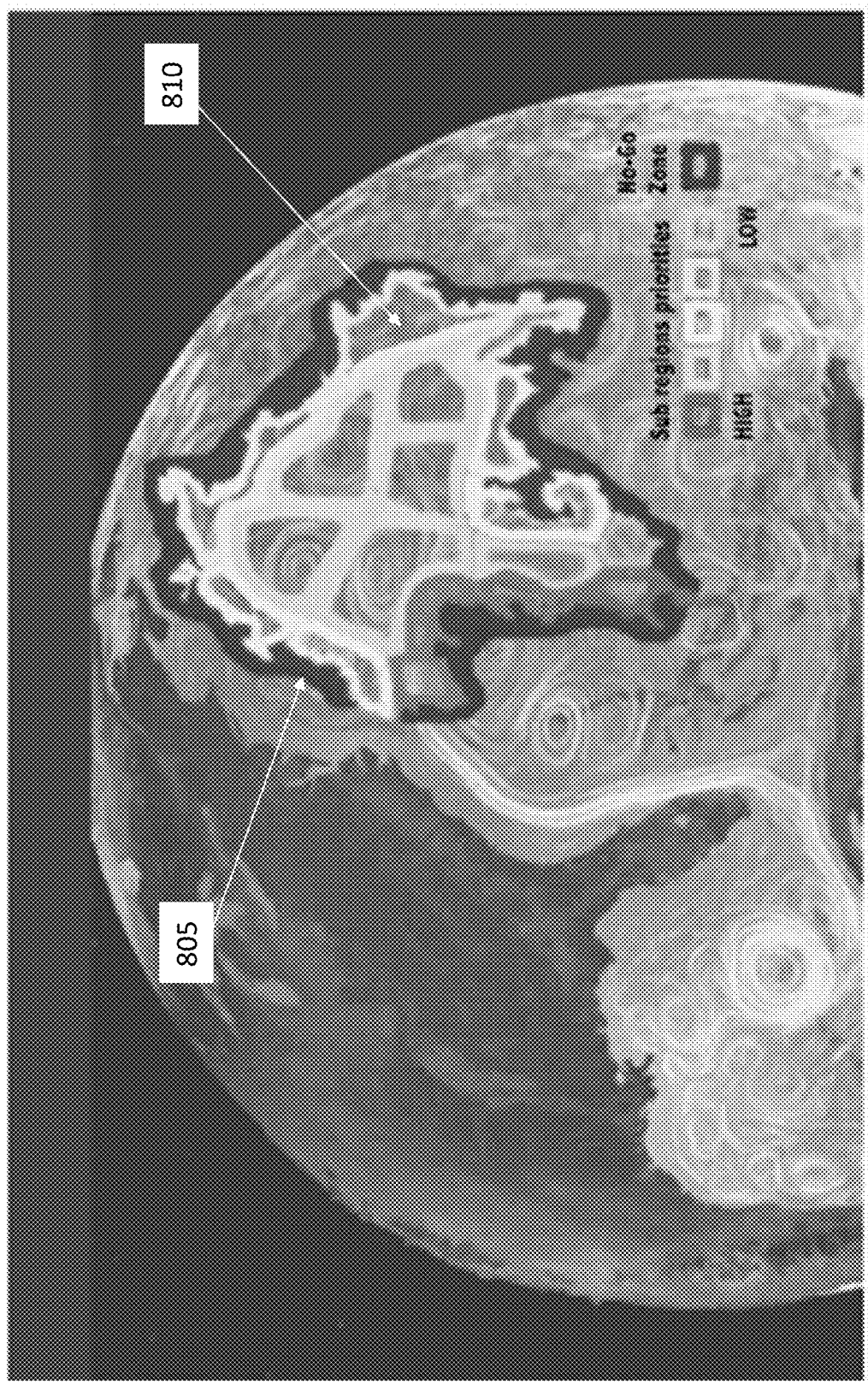
FIG. 5 illustrates an example of a prioritized region.

FIG. 5 illustrates an example of a priority region assignation. The buoy system may be directed to deploy in a specific area of the ocean, where certain regions are assigned a higher priority, for example the internal regions (810), while other regions are assigned a lower priority, for example the outer regions (805). Some regions may also have a no-go priority, meaning that the buoys should avoid such regions. The no-go priority may also be an internal region to the overall assigned region, for example because of a hazardous area (such as an underwater semi-submerged structure or an active volcano) within an area of interest.

Figure 3:
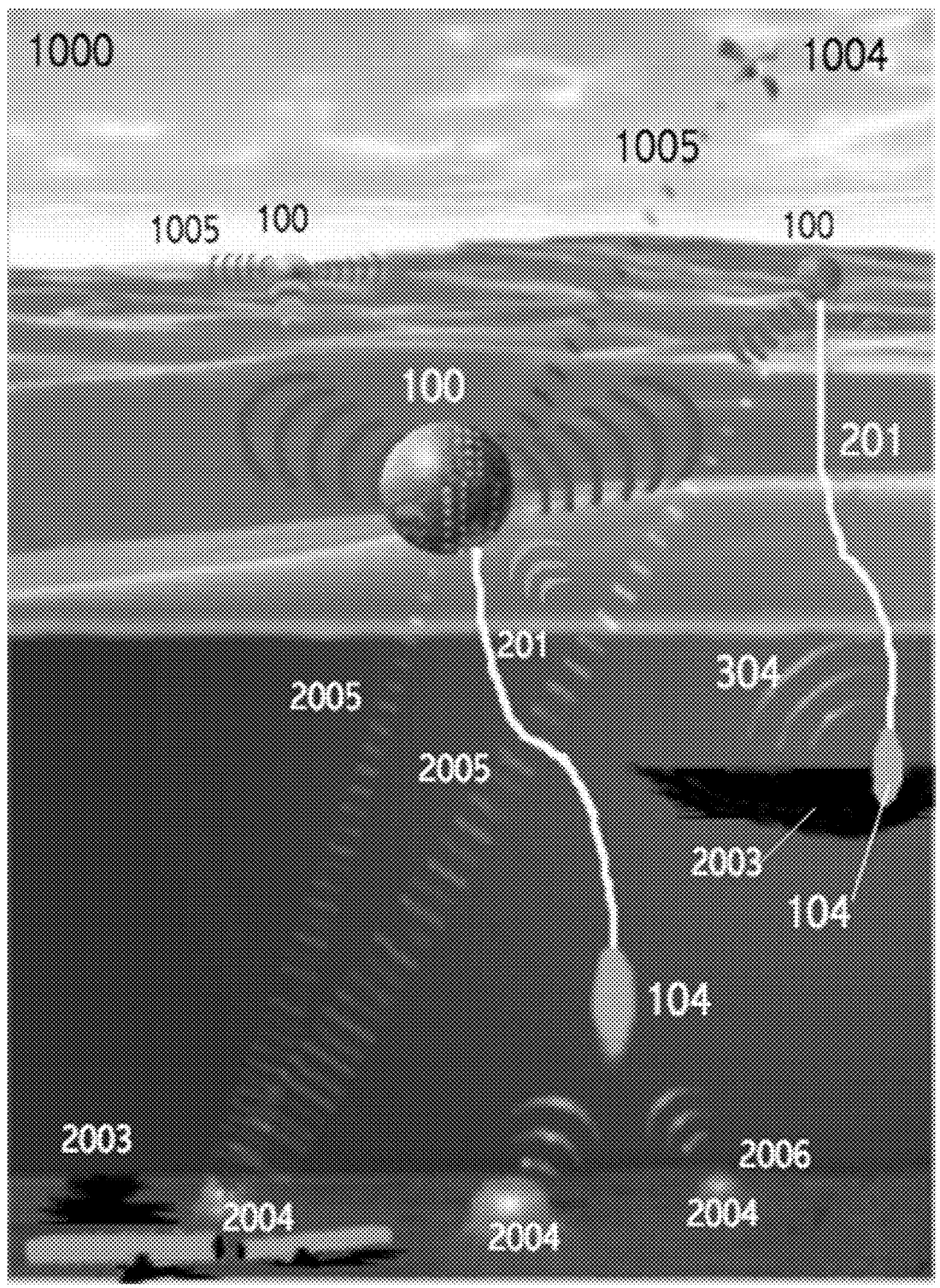
FIG. 3 illustrates an example of the way the controllable buoys can stay stationary and perform acoustic beam forming and triangulation and positioning.

In some embodiments, the TUVs can triangulate their position (and the position of a detected event) by sending acoustic signals to nearby buoys as illustrated in FIG. 3, for example. The TUVs (104) are able to locate themselves and an incident (2003), such as an oil leak, and objects that they observe (2004), such as an ocean floor sensor, by sending an acoustic signal (2005) that could be received by the mother-buoys on the surface (100) in order to perform the triangulation. Since the exact location of assets under the water (2004) can be determined, the mother-buoys are able to send directional acoustic beams (2005) to communicate with the assets (2004) already localized. This is possible since the mother-buoys are able to remain stationary through their motion control. The buoys (100) also have access (1005) to global clocks (1004) and are able to synchronize their clocks in order to communicate with the assets via phase-arrayed beams (2005). Sending directional acoustic beams (2005) has the advantage of not only saving power but also sending effective acoustic signals (2005) with higher rates deeper under water. Furthermore, it does not disturb the mammals and also does not get easily detected by adversary agents in the oceans the way larger angled acoustic signals do. Moreover, the TUVs (104) could be sent deeper under water in order to communicate (2006) to the assets (2004) under water and check their status.

Figure 6:
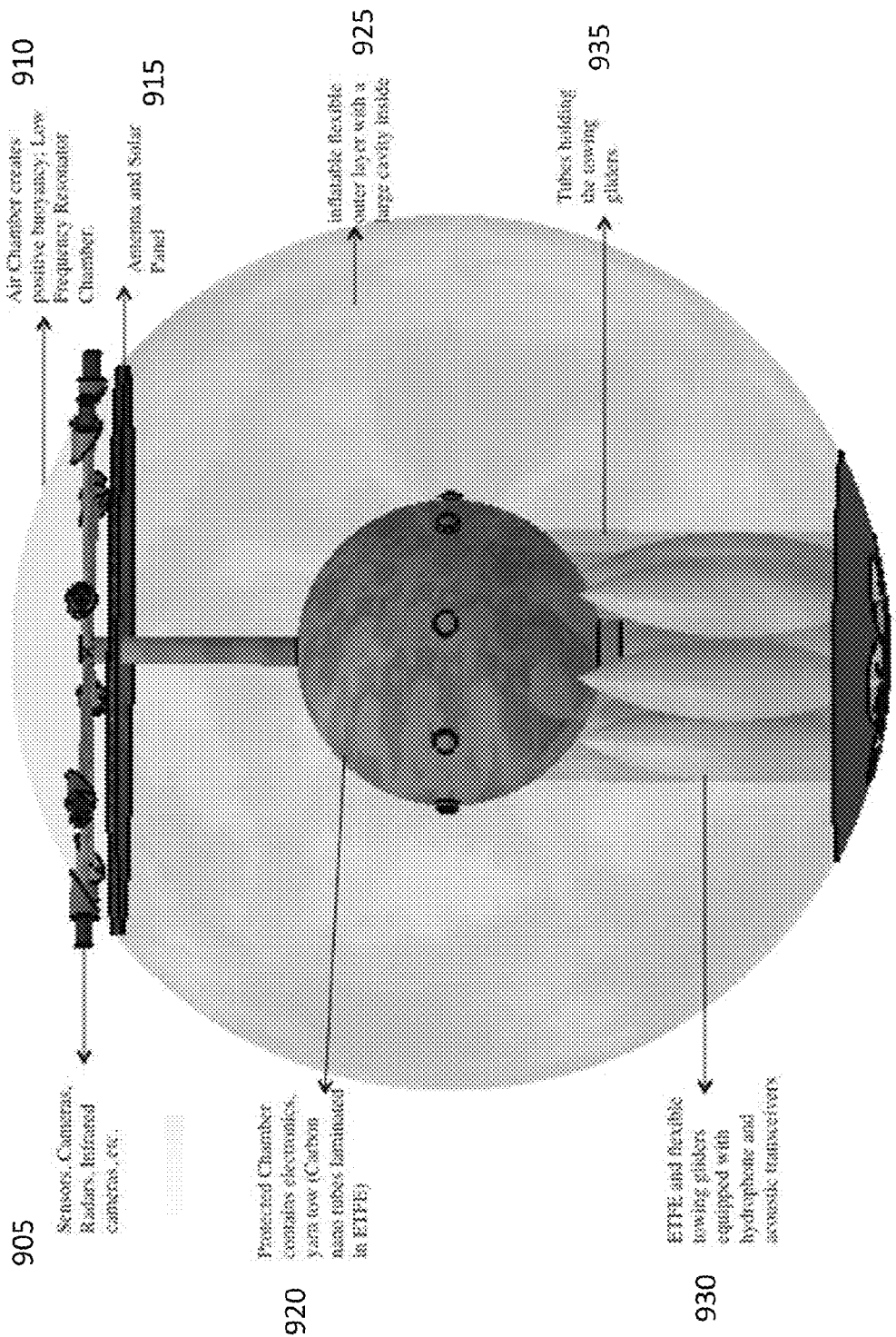
FIG. 6 illustrates an exemplary controllable buoy with docked underwater vehicles.

FIG. 6 illustrates an exemplary buoy with docked TUVs. The buoy can comprise sensors, cameras, radars in a platform at the top of the buoy (905); an air chamber to control buoyancy and act as a low frequency resonator chamber (910); an antenna and solar panel (915); an internal protected chamber comprising electronics and a tow line such as carbon nanotubes (920); an inflatable outer layer with a large cavity inside (925); towing TUVs with hydrophones and acoustic transceivers (930); and housing tubes (935) for the TUVs.

Figure 7:
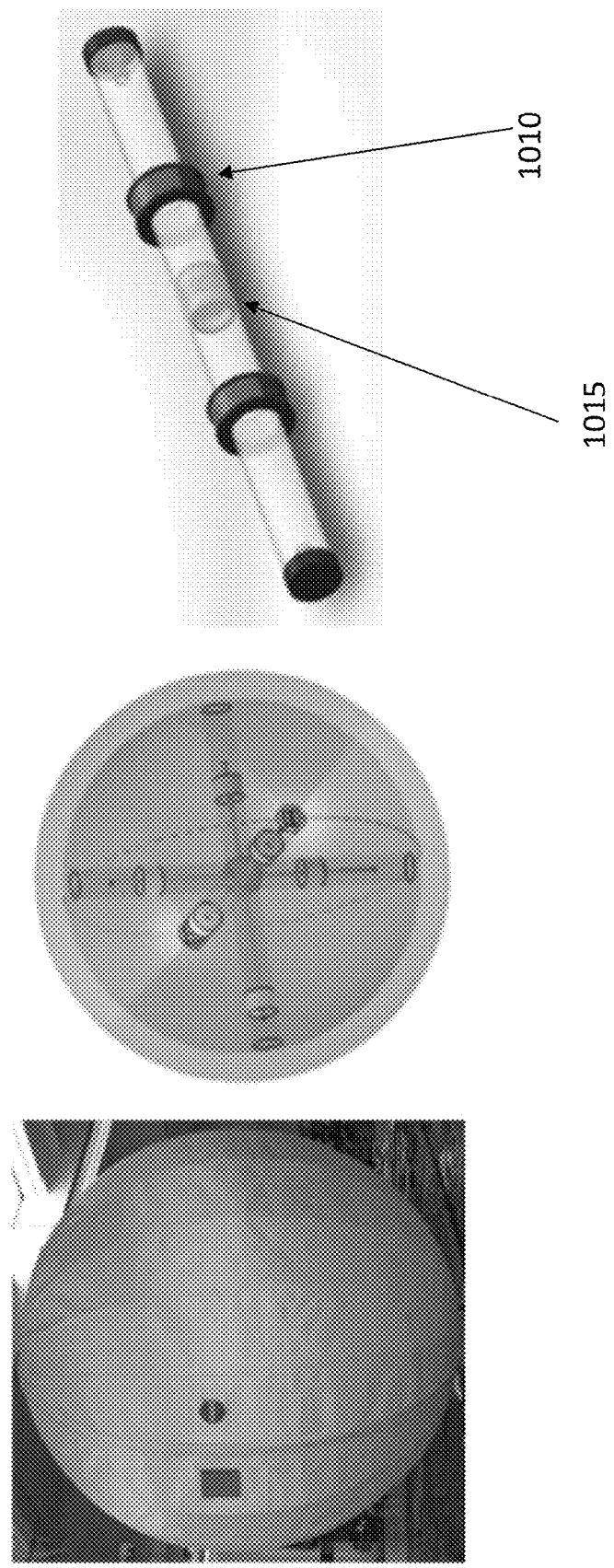
FIG. 7 illustrates a prior art energy harvesting method.

In some embodiments, the buoys can harvest energy from the motions caused by the waves, wind, and currents. For example, a linear induction system could be used, comprising light tubes covered by solenoids (1010) with moving magnets (1015) inside, as illustrated in FIG. 7 and as described in U.S. Pat. No. 8,912,892, he disclosure of which is incorporated herein by reference in its entirety.

Figure 8:
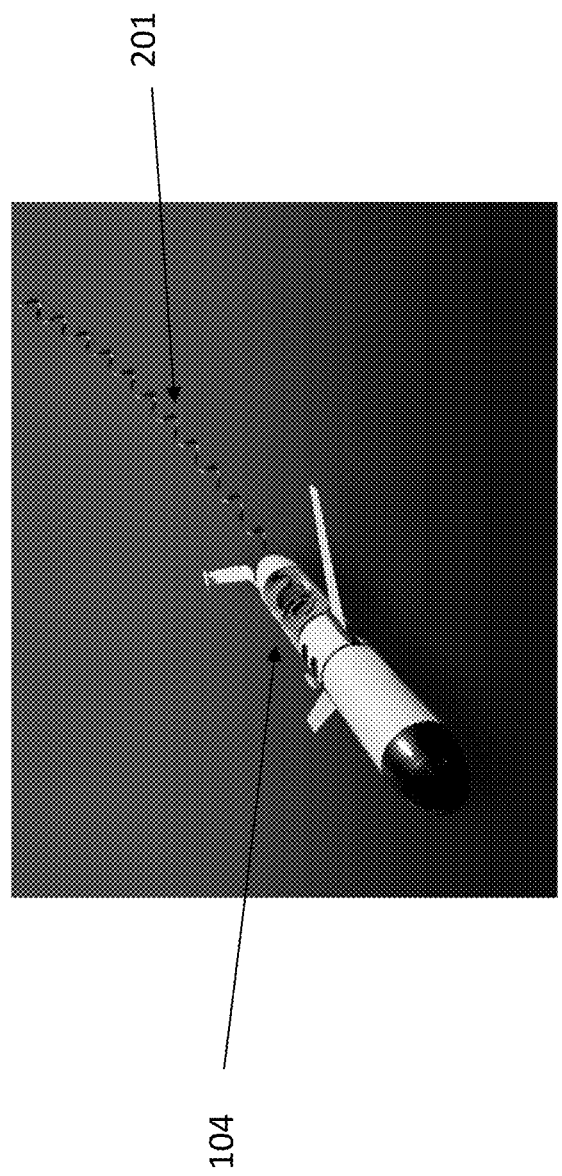
FIG. 8 illustrates an exemplary embodiment for a spooling cable for a tethered underwater vehicle.

FIG. 8 illustrates an exemplary embodiment for a spooling cable for a TUV. The spooling cable (201) can have a curled shape and be housed inside the TUV (104). Alternatively, the cable could also unwind from the buoy instead. Therefore, a buoy's TUV could be equipped with its own internal controllable spool and tethers integrated inside its shell to help the TUV maneuver at large depths, where the drag on the trailing cable may be substantial. When deployed from the TUV, the trailing tether need not contend with the drag from the long drop of the tether from the mother ship.

Figure 9:
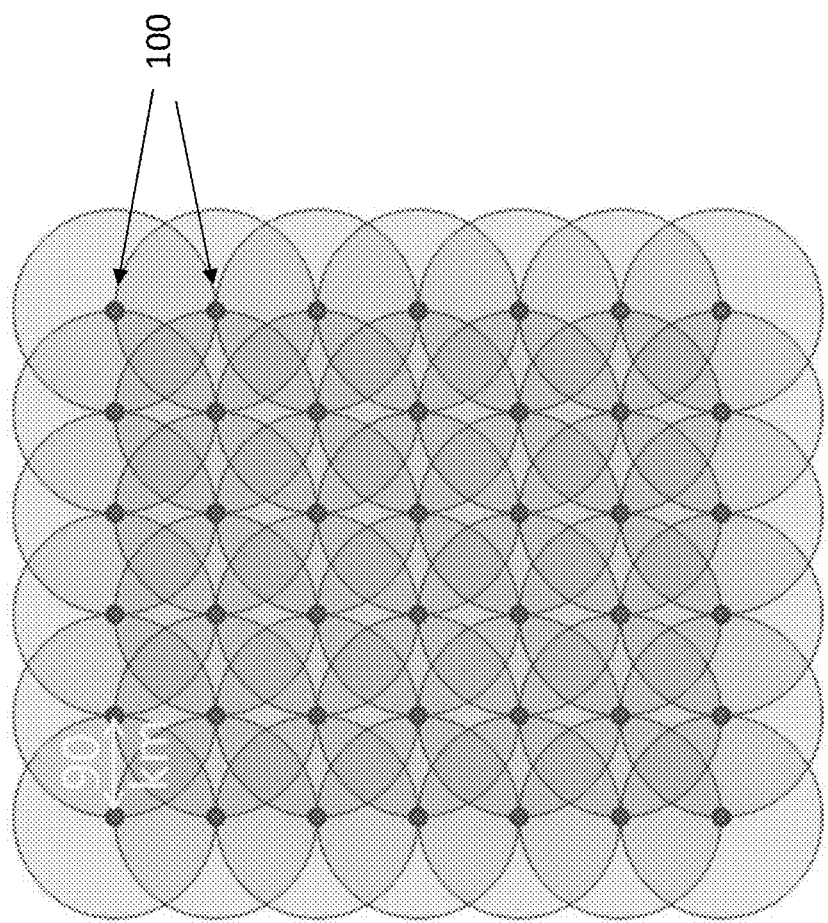
FIG. 9 illustrates an exemplary network of controllable buoys covering a large area.

In some embodiments, the network of buoys and TUVs can form a continuous networked system that can transfer communications from great distances. For example, FIG. 9 shows a wide network formed with a regular grid formed by buoys (100) about 90 km apart (1205).

For example, the buoy's TUVs can be able to descend 1000-2000 m beneath the ocean surface and under the thermocline layer, where the TUVs can communicate with other underwater receivers within a 90 km radial distance (see for example Refs. [13-16]). Hence, the acoustic signal's travel time from a TUV transponder to any underwater node can be 60 seconds or less (since sound travels at about 1.5 km/sec below 1000 m). Since the TUV can be connected to the surface via a fiber-optic link, even with message de-encryption and verification, at most there can be, in some embodiments, a 65 second delay from the receipt of a signal at a mother-buoy and the subsequent receipt of that signal at a underwater node via an acoustic broadcast. Based on these estimates, 120 TUV buoys, separated by roughly 90 km distance, could communicate with any underwater node in a 1,000,000 km$^2$ area.

Figure 10:
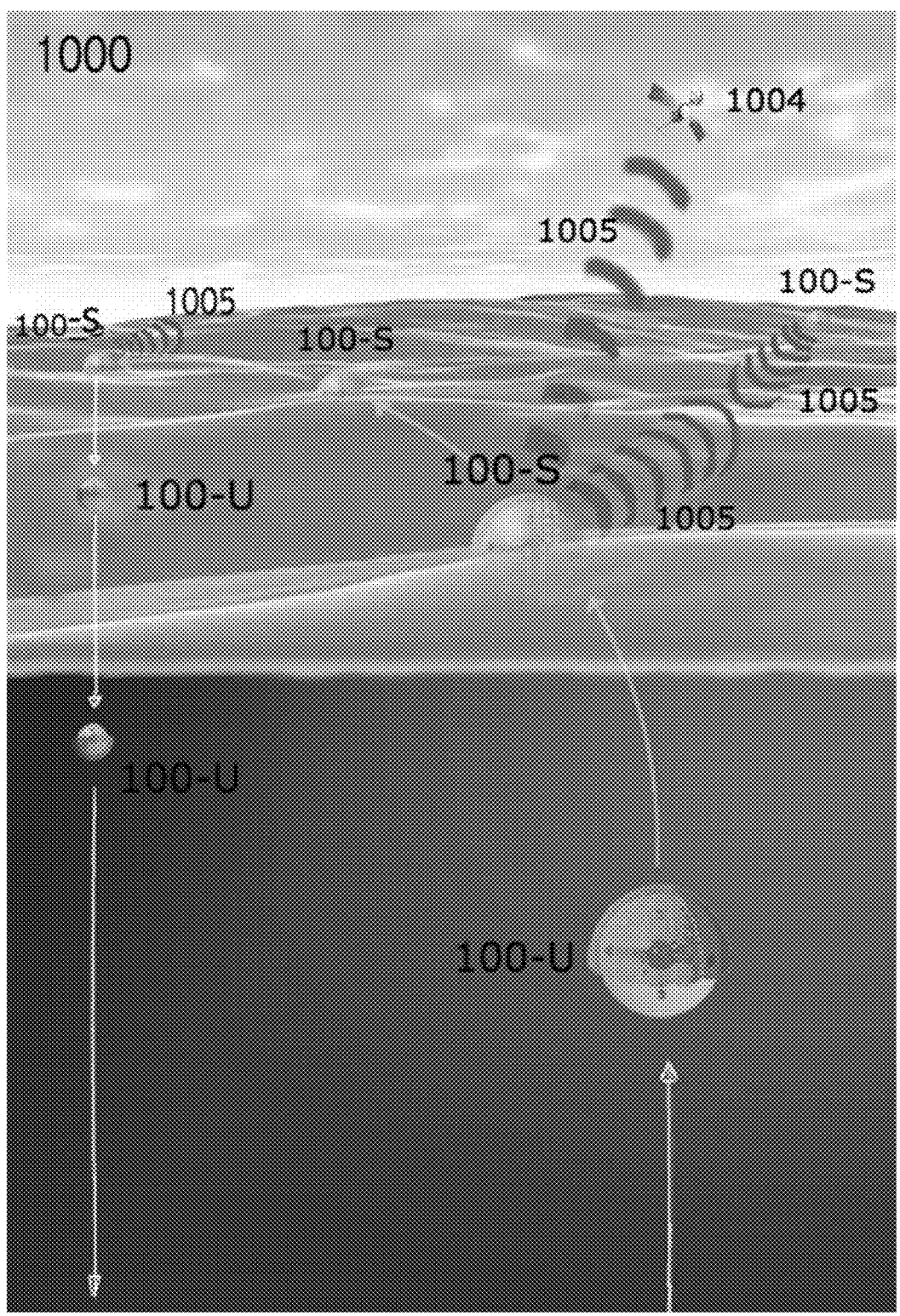
FIG. 10 illustrates an exemplary network of controllable buoys capable of moving up and down under the surface of the water and also moving on the surface

FIG. 10 illustrates an exemplary network of buoys (100-U, 100-S) without TUVs, depicting one floating buoy (100-S) and one other buoy (100-U) going from underwater to the surface then back underwater. These buoys can float on the surface (100-S), or control their buoyancy by submersing at a desired depth (100-U). When required, the buoys (100-U) can resurface, for example to transmit data. The underwater buoys (100-U) could also directly communicate with other buoys (100-S), for example floating buoys, in order to communicate with the surface or a satellite (1004). The buoys without TUVs can comprise any of the features described above for the buoys that can deploy TUVs. The materials, structure, composition and capabilities can all be similar, except for the capacity to deploy TUVs. Therefore, the buoys depicted in FIG. 10 can also network, transmit messages and data, and carry out beam forming together with other buoys.

Figure 11:
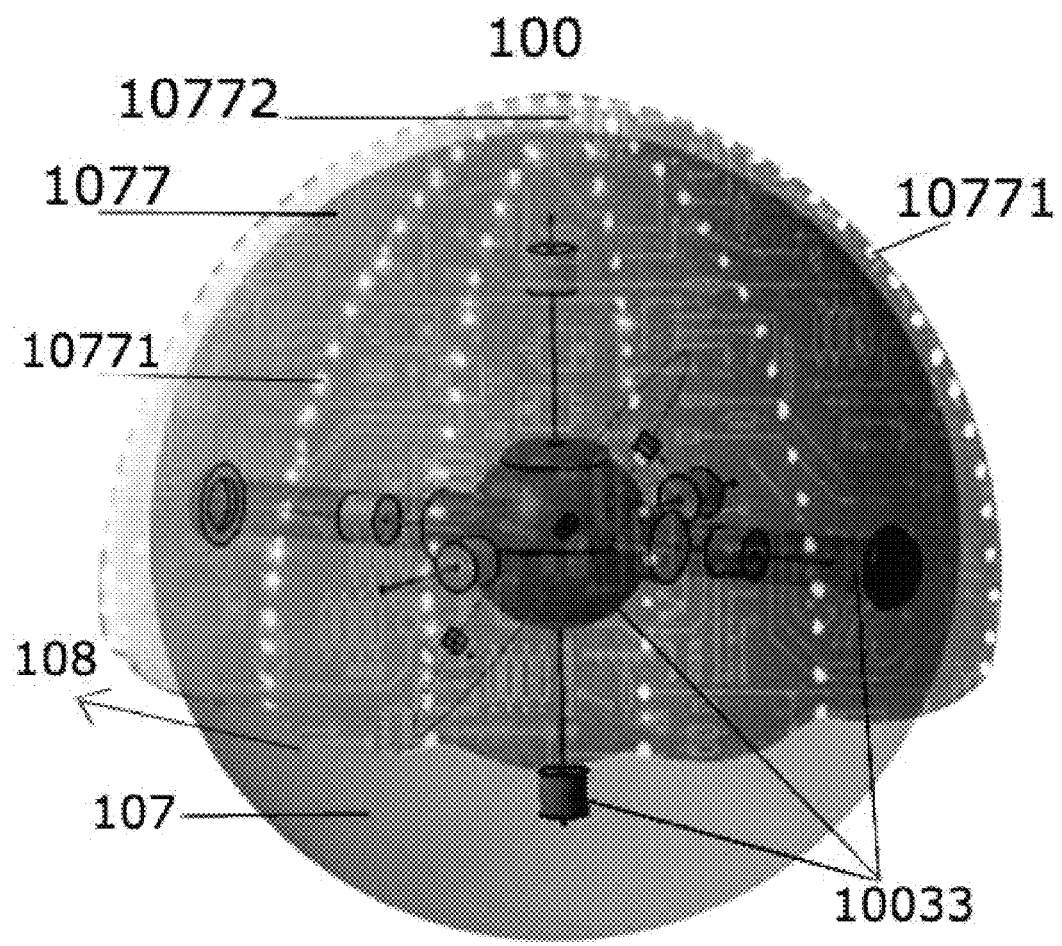
FIG. 11 illustrates an embodiment of a controllable buoy utilizing jellyfish style underwater propulsion.

FIG. 11. demonstrates another embodiment of the controllable buoy (100) which is capable of using various Bio-mimic swimming movements and techniques similar to jellyfish robots such as RoboJellies™ (see www.emdl.mse.vt.edu/projects/alex.html) [35] to swim up and down in the ocean. The outer layer of the buoy (100) could compromise of two parts: a complete spherical layer called inner-shell (107), which covers the entire internal cavity (108) of the buoy (100). There is also an outer-shell (1077) on top of the inner-shell (107) and connected to the inner-shell and the internal structure (10033) at the top of the buoy (10772) using various joints made of ETFE or other materials mentioned herein. Both the inner-shell (107) and outer-shell (1077) could be made of ETFE, or other flexible materials such as Dragon Skin Silicone, EcoFlex Silicone, Bell Mesoglea, in combination with Bio-Inspired Shape memory Alloy Composites (BISMAC) (iopscience.iop.org/0964-1726/19/2/025013) actuators (10771). The outer shell (1077) could use its actuators (10771) actively to expand and contract its structure and mimic the movements of a jellyfish such as *Aurelia Aurita* or similar to RoboJellies™ [35] and therefore to swim up and down in the water. When the buoy (100) is under the surface of the water, its inner-shell (107) could get completely deflated in order to make the entire structure of the buoy more hydrodynamic and therefore easier to swim down. On the other hand when the buoy (100) is on the surface, the inner-shell (107) should be fully inflated to form a shape of an sphere (100-S). The buoy on the surface (100-S) can take advantage of the wind and currents on the surface of the ocean, and also its submergence (as mentioned in this disclosure) in order to adjust its movement (its direction and the speed). One or more mechanical control and energy harvesting systems (10033), such as ones mentioned in the U.S. Pat. No. 8,912,892, could be integrated inside the buoy (100), in order to give the buoy more control for its movements and to help the buoy generate power from the wind-driven and current driven motions. On the other hand the buoy (100) could have neither internal mechanics (10033) nor the internal-shell (107) and would be able to still work. When the buoy (100-U) is under the surface of the water, it can perform swimming. When the buoy (100-S) comes to the surface, the bottom part of the outer-shell (1077) can come together (for example by using Bio-Inspired Shape memory Alloy Composites (BISMAC) (see iopscience.iop.org/0964-1726/19/2/025013) actuators and have them get stiffed together in a point at the bottom of the sphere) in order to form a sphere and therefore, take advantage of the winds and currents on the surface. Various low-mass and low-power electronics such as the imagers, sensors, avionics, communication transceivers and antenna (e.g., for RF, optic, or acoustic), thin-film batteries and solar cells, and other electronics mentioned in Table 1, could be imprinted on Kapton™ or other circuitry printable materials, and laminated inside the ETFE layers which compromise the outer-shell (1077) or the inner-shell (107) of the controllable buoy (100). The disclosed techniques herein allow the entire structure of the buoy (100) to be covered by various sensors, imagers, antenna, and energy harvesting materials (solar) and enable the buoy (100) to be efficient (in terms of the various monitoring tasks it can perform). Having a large antenna can help the buoy have a better communication with other assets in the ocean. Having a large area for solar or other energy harvesting techniques (such as ones mentioned in U.S. Pat. No. 8,912,892) can allow it to generate a large amount of power from the sun (when the buoy (100-S) is on the surface) or from movements or thermoelectricity techniques when the buoy (100-U) is under the surface of the water. The current state-of-art in bio-mimic swimming robots, does not suggest using ETFE and laminated electronics any flexible circuitry printable thin films and imprinted circuits covering and laminated over the flexible their bodies. Instead, they use a small waterproof chamber, usually on top of the robot, in order to hold the electronics and sensors used for the robot: for example, RoboJellies™ [36]. These make space available for the electronics (e.g. sensors), and energy harvesting (e.g. solar cells), and therefore the quality of their performance very limited.

Figure 12A:
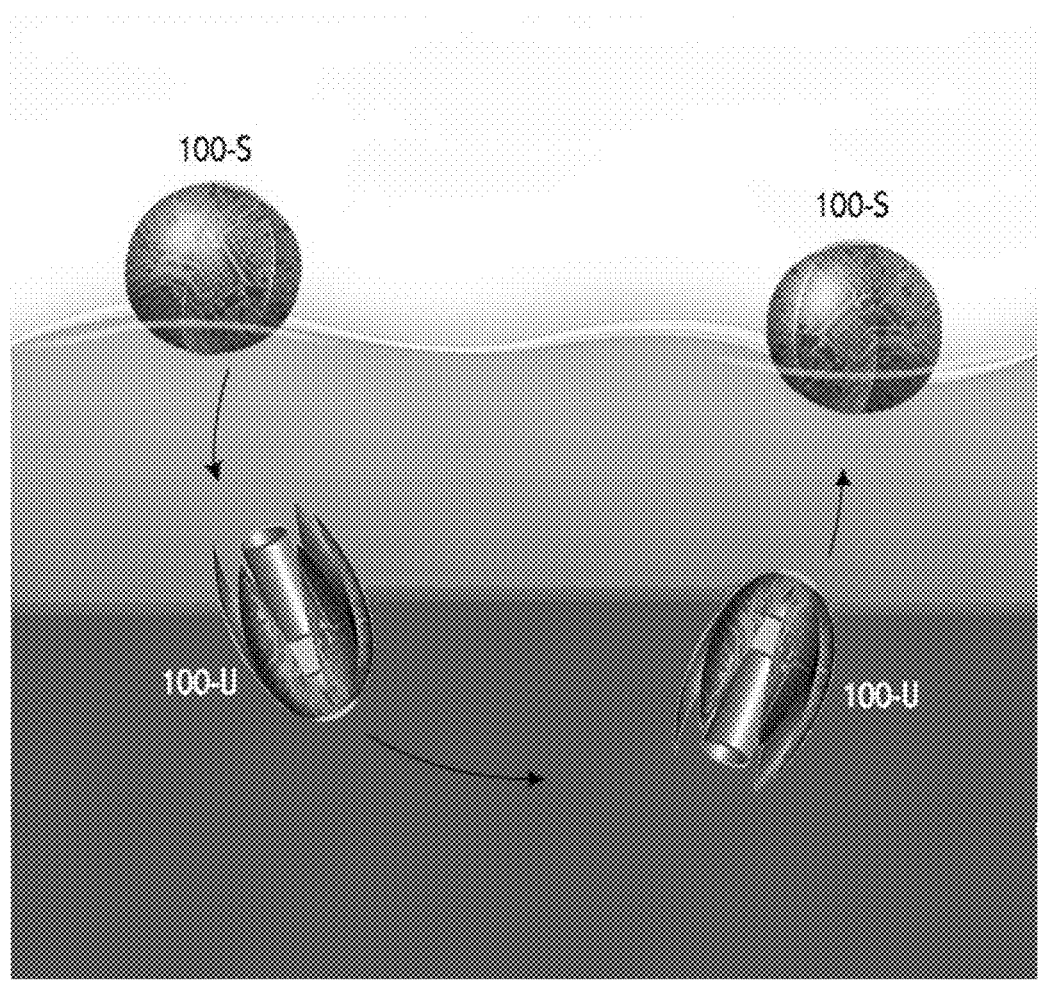
FIG. 12A illustrates an embodiment of the controllable and phase-changing buoy which can change its structure from wind-driven on surface to more hydrodynamic under the surface of the water.
Figure 12B:
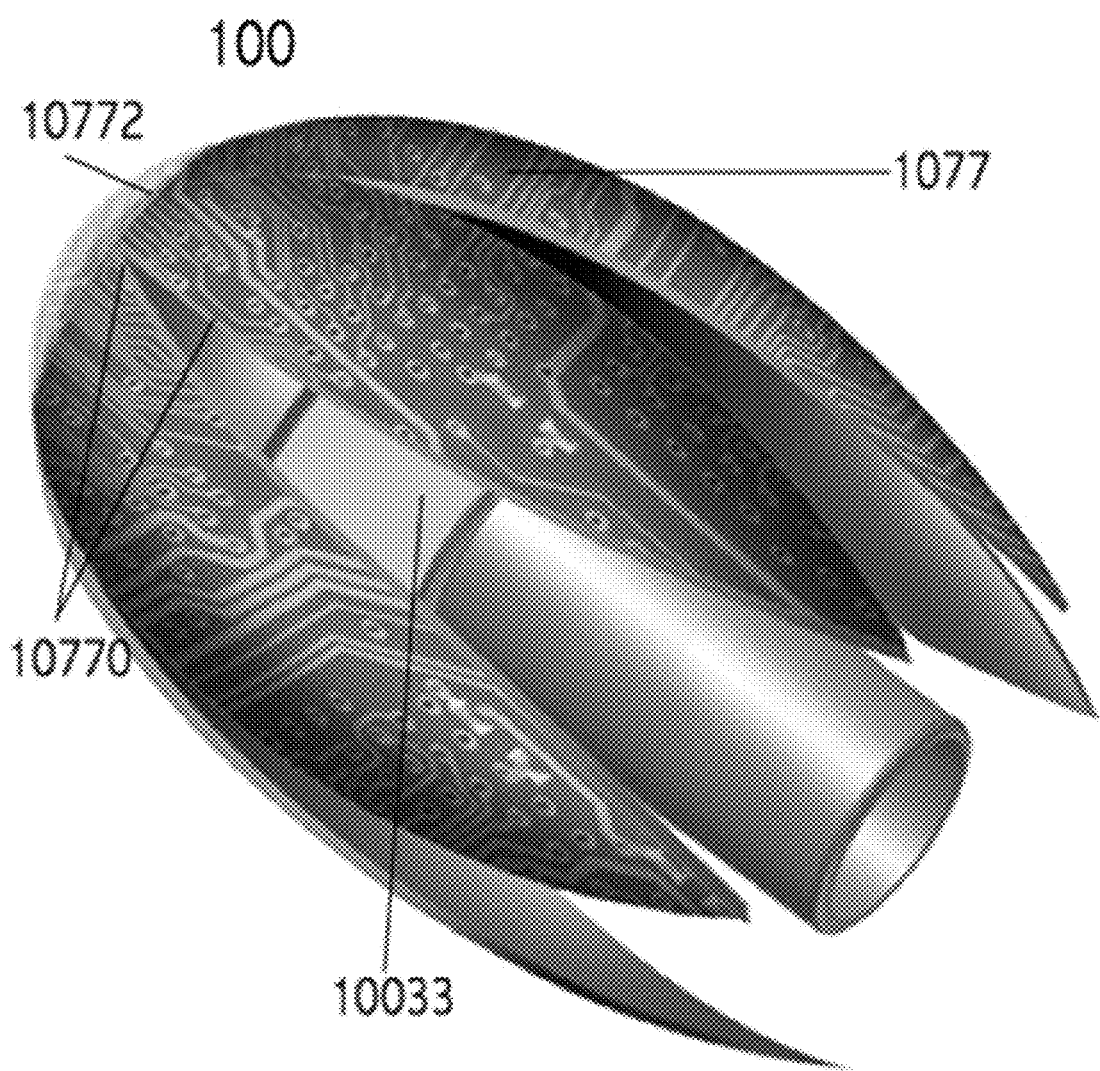
FIG. 12B illustrates a closer view of the buoy depicted in FIG. 12A.

FIGS. 12A and 12B demonstrate another embodiment of the controllable buoy (100). The structure of the buoy (100) is phase changing and can swim up and down in the oceans and move on the surface of the water. The buoy (100) has compromised of two parts: its internal and optionally rigid shell containing various control systems (10033) such as buoyancy engine, the propeller, etc. to help the buoy move in the water; and its outer and preferably flexible shell (10077) in order to mimic the jellyfish-robots and squid-robots and help the buoy swim inside the ocean. The other sell can be made of sturdy and pressure resistant materials such as Titanium, steel, fiberglass, ETFE, PTFE, nano carbon fibers, etc. The outer-shell (10077) could be made of ETFE in combination with other flexible materials such as Dragon Skin™ silicone, EcoFlex™ silicone, Bell Mesoglea™. Various actuators such as the Bio-Inspired Shape memory Alloy Composites (BISMAC™) (iopscience.iop.org/0964-1726/19/2/025013) actuators (10771) could be integrated in the flexible (10077) in order to give it flexibility and control to contract and expand and can use the state-of-the-art bio-mimic swimming methods similar to RoboJellies™ (www.emdl.mse.vt.edu/projects/alex.html) [35] and move inside the water. In this example embodiment, the outer shell (1077) can be comprised of slices (10770) of movable and swimming parts, contrary to the example embodiment in FIG. 11, where the outer-shell was more similar to a skirt or a jellyfish. Several sensors, energy harvesting, and electronics could be integrated and laminated inside the outer shell (1077) using the methods and materials mentioned in FIG. 10 or the U.S. Pat. No. 8,912,892. When the buoy (100-S) is on the surface, the other-shell's slices could come together, using their actuators, to form a sphere. A telescoping chamber (10033), where a buoyancy engine or the propeller can reside, can also be used to transform the shape of the buoy between elongated and spherical. When the buoy is on the surface (100-S) and in spherical shape, it can take advantage of the stronger winds and currents to move faster. The slices (10770) can also help the buoy (100-S) to change its buoyancy and therefore submergence in order to control its speed against the winds and currents, as described herein. Moreover, the slices (10770) could use their actuators in order to change the structure of the buoy against the wind and therefore, to control the buoy's trajectory (similar to sailing).

The internal mechanics (10033) could be such that they would be able to change their structure, in order to make them more hydrodynamic when they need to sink and move into the deeper waters. For example, a longer tube or chamber, containing a propeller or a buoyancy engine, can be elongated when the buoy moves under the surface of the water. Conversely, the longer-tube or chamber can be retracted and become shorter when the buoy returns to the surface, changing its shape to a sphere, or some other aerodynamic shape, to take advantage of the stronger winds and currents on the surface of the sea for their mobility.

Figure 13:
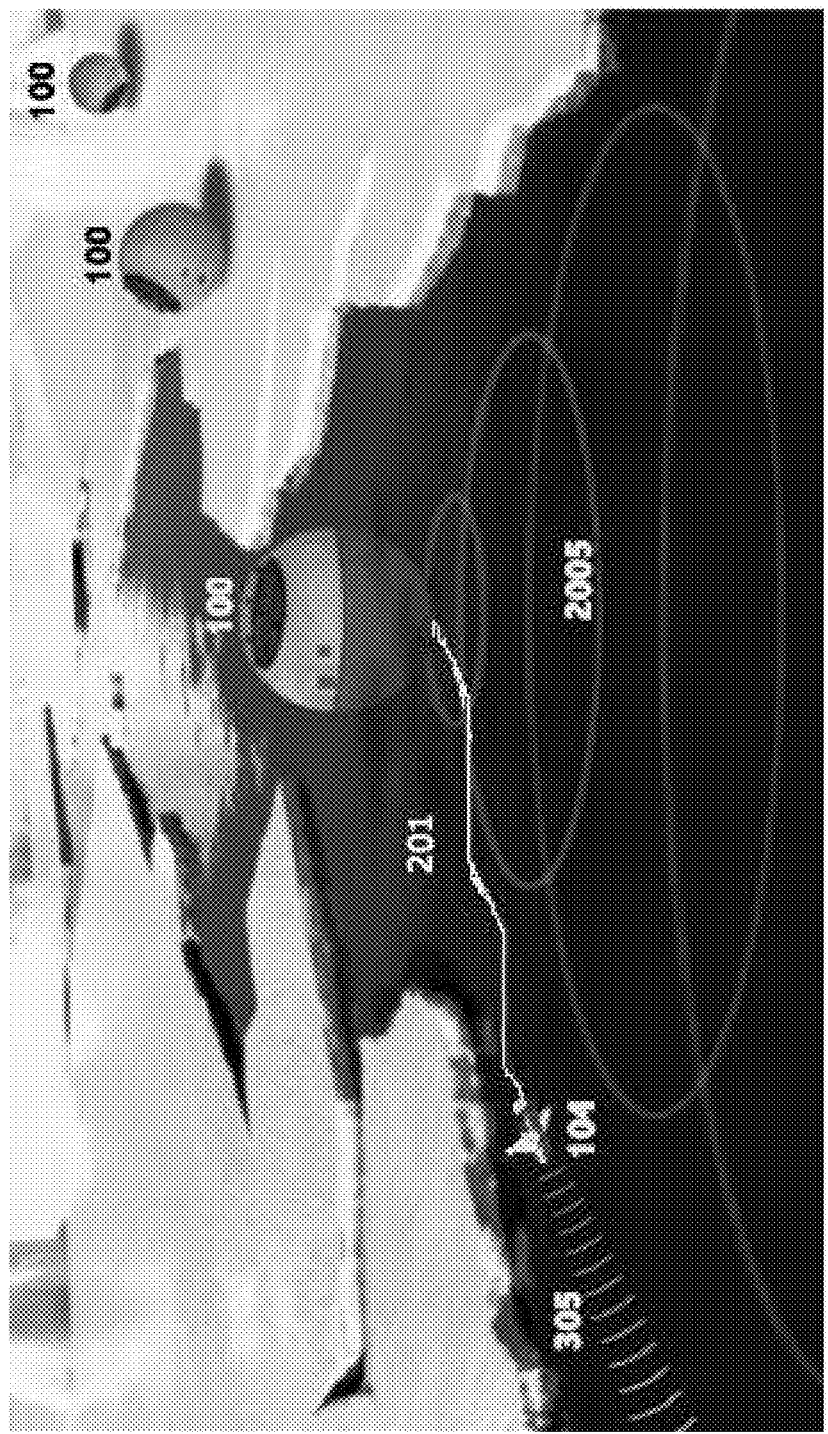
FIG. 13 illustrates an embodiment of a controllable buoy when the buoy can move both on a hard surface and in the water and can send its underwater vehicle to monitor under the water

As shown in FIG. 13, when the controllable buoy is on the water its TUV can be dropped in the water in order to go deeper in the water and perform tasks such as monitoring the area, mapping the ice, or performing sonar detection or acoustic communication (305, 2005) with the under the surface of ice and in the underwater assets. The mother-buoy and TUV can use various detectors, imagers such as sonars, radars, optic and infrared cameras, or sensors for monitoring in the water and under the surface of ice. They can also use various RF, optic, laser, or acoustic modems transceivers to perform communication (e.g., the sensors in Table 1).

Figure 14:
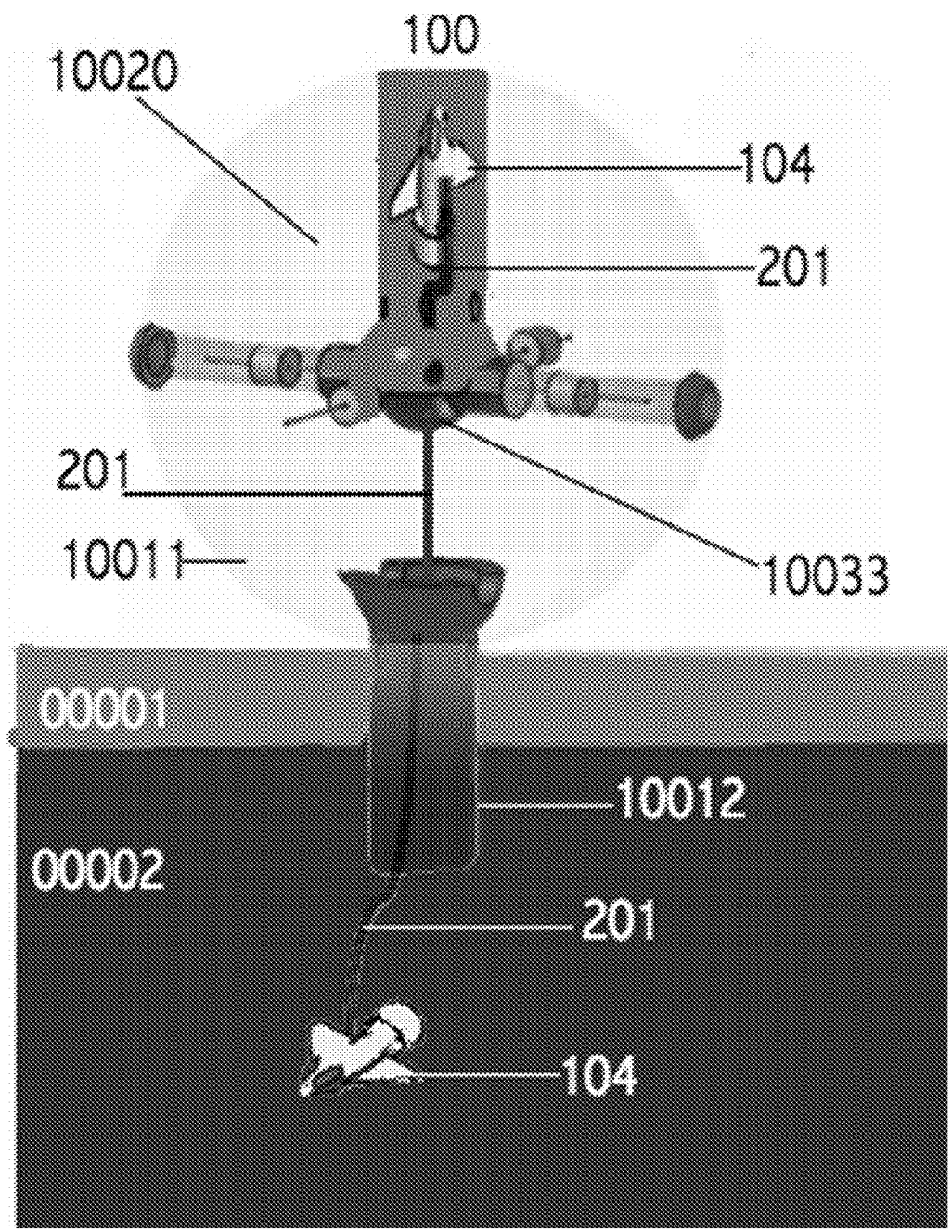
FIG. 14 illustrates the details of an embodiment of a controllable buoy when the buoys can pierce itself into the ice or release itself from the ice and move around

FIG. 14 demonstrates an example embodiment of the controllable and moving buoy (100) and (10020) equipped with an ice penetrating and sticking mechanism and instruments in order to penetrate through and become temporarily stuck in the ice. The ice-penetrating and moving buoy (10020) can use ice-sticking techniques in order to control the movement of the buoy and make it stable in an area of interest (for example, when the wind is blowing and the buoy shouldn't move), or when the buoy needs to monitor under the surface of the ice. The buoy (10020) can use the mechanics (10033), such as ones described in the U.S. Pat. No. 8,912,892, to move around (10055), to harvest the abundance of the wind in the polar region (such as ones as described in the U.S. Pat. No. 8,912,892 and developed and studied in reference [35]), or to stick itself inside the ice. One or more ice-penetrating tubes (10012) holding a TUV (104), a stick, or a drill could be attached to the buoy's internal mechanics (10033). Therefore, the tube can be lowered or retrieved up using the same mechanical control systems mentioned in the U.S. Pat. No. 8,912,892.

The ice-penetrating tube (10012) can be made of titanium, aluminum, fiber glass, carbon fibers, PTFE, etc. and can be equipped with various ice-penetrating tools and materials such as the state of art heaters or electrical coils which generate heats. For example: entire or parts of the tube could be made or covered with electrical heaters such as: Micro Electric™ electrical heaters (see, e.g., www.microelectricheaters.com/tubularheaters.htm) or a coil around the ice-penetrating tube (201) that would generate heat when the electricity passes the coil, radio isotope heater units (see, e.g., solarsystem.nasa.gov/rps/rhu.cfm), a heater unit that utilizes fuels or propellant to generate heat, chemicals that generate heat when in touch with ice and water (e.g., alkali metals), or a silicon heater pad (for example, see www.omega.com/pptst/SRFR_SRFG.html).

After the tube or the stick would successfully finish melting the ice around them, the cold ambient temperature would make the melted ice to freeze around the tube or the stick. This would make the ice-penetrating tube firmly affixed inside the ice (00001), which in turn would make the attached buoys (100) pinned into the ice and become stationary. The buoy (10020) is able to unstick itself from the ice, using the same heating, chemical, or drilling techniques mentioned in above, while using its mechanical control system (10033) to pull its tube (10012) back up inside its inner structure).

When the tube (10012) is penetrated through the ice (00001), and when it reaches the water (00002) beneath the ice, the buoy's central control system, either residing in the buoy itself or controlled by the signals and commands received from the satellite (1004) or the other buoys and assets in the area, can launch the TUV (104) into the water to monitor the under the ice. Various ice and water detecting, temperature, salinity, various chemicals sensors (e.g., the ones mentioned in the U.S. Pat. No. 8,912,892 or in Table 1), can be integrated inside the tube in order to collect the necessary information about the status of ice and water to facilitate the system's (1000) decision to launch or retrieve the TUV (104).

Figure 15:
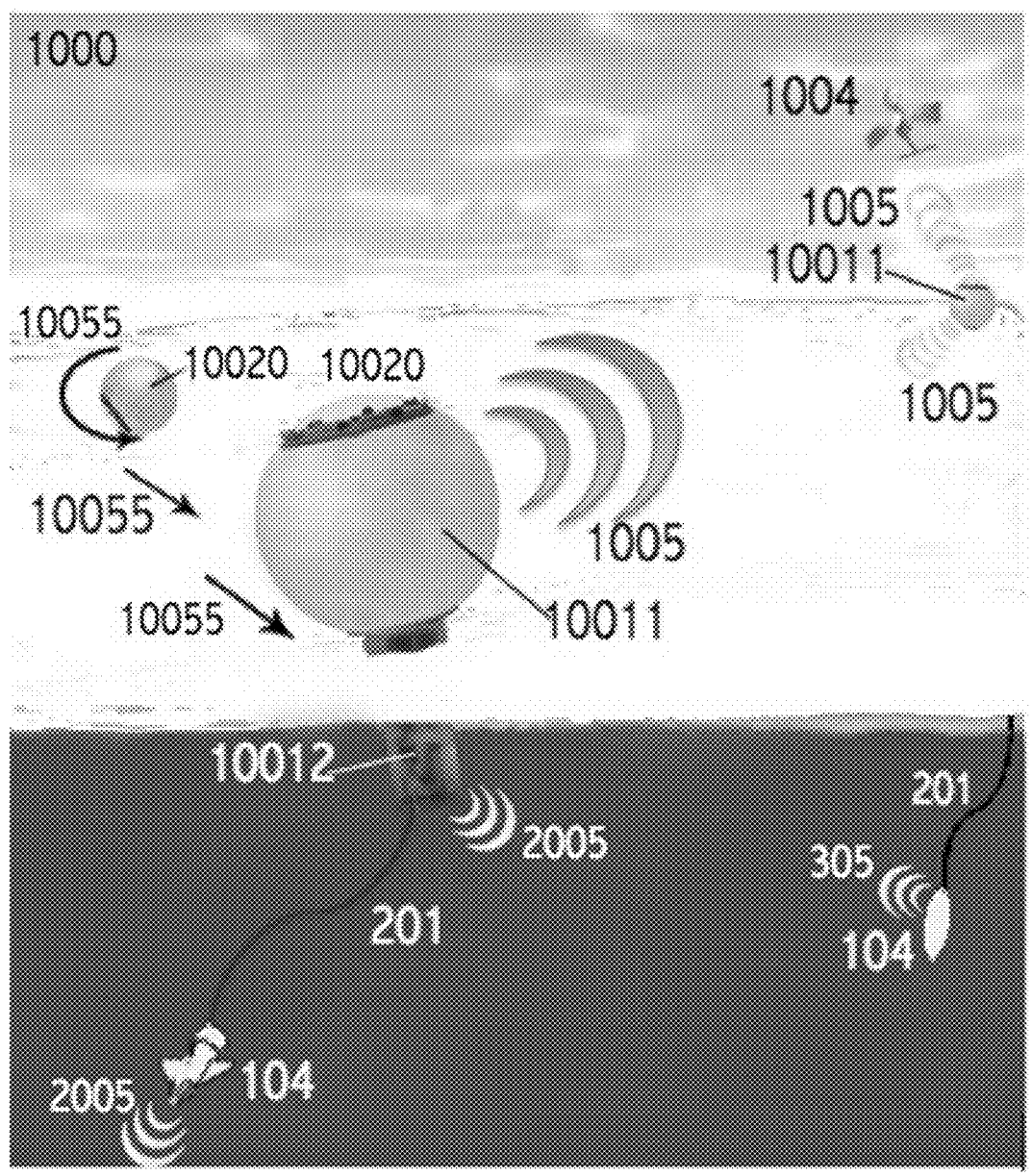
FIG. 15 illustrates an embodiment of a network of controllable buoys when the buoys can pierce themselves into the ice or release themselves from the ice and move around.

FIG. 15 shows an embodiment of the controllable networked buoy system (1000) when the buoy (10020) is capable of moving (10055) on the surface of the ice, or when it gets pinned inside the ice (using the techniques mentioned above). The buoy (10020), when stuck into the ice, has its upper-part (10011) able to communicate (1005) (e.g., RF, optic, laser) with other buoys or assets (1004) on the surface and above the surface of the ice (e.g., satellites, airplanes, etc.). The buoy's lower part (10012), which is inside and under the ice, can use various communication techniques such as acoustic, RF, or laser (e.g., Texas Instruments™ TMS320C5416 DSP or WHOI™ Micro-Modem™ [34] or the ones mentioned in Table. 1), to perform communication (2005) with assets under the surface of the ice. A cable (201) connecting the buoy to its TUV (104) provides wired communications (RF or optic) between the TUVs (104) and their mother-buoys (100). Therefore, the network of buoys (1000) illustrated in the FIG. 15, including the buoys' upper-parts (10011), lower-parts (10012), and their tethered TUVs (104), can perform collaborative positioning, communication, and monitoring tasks the same manner as described herein.

Figure 16:
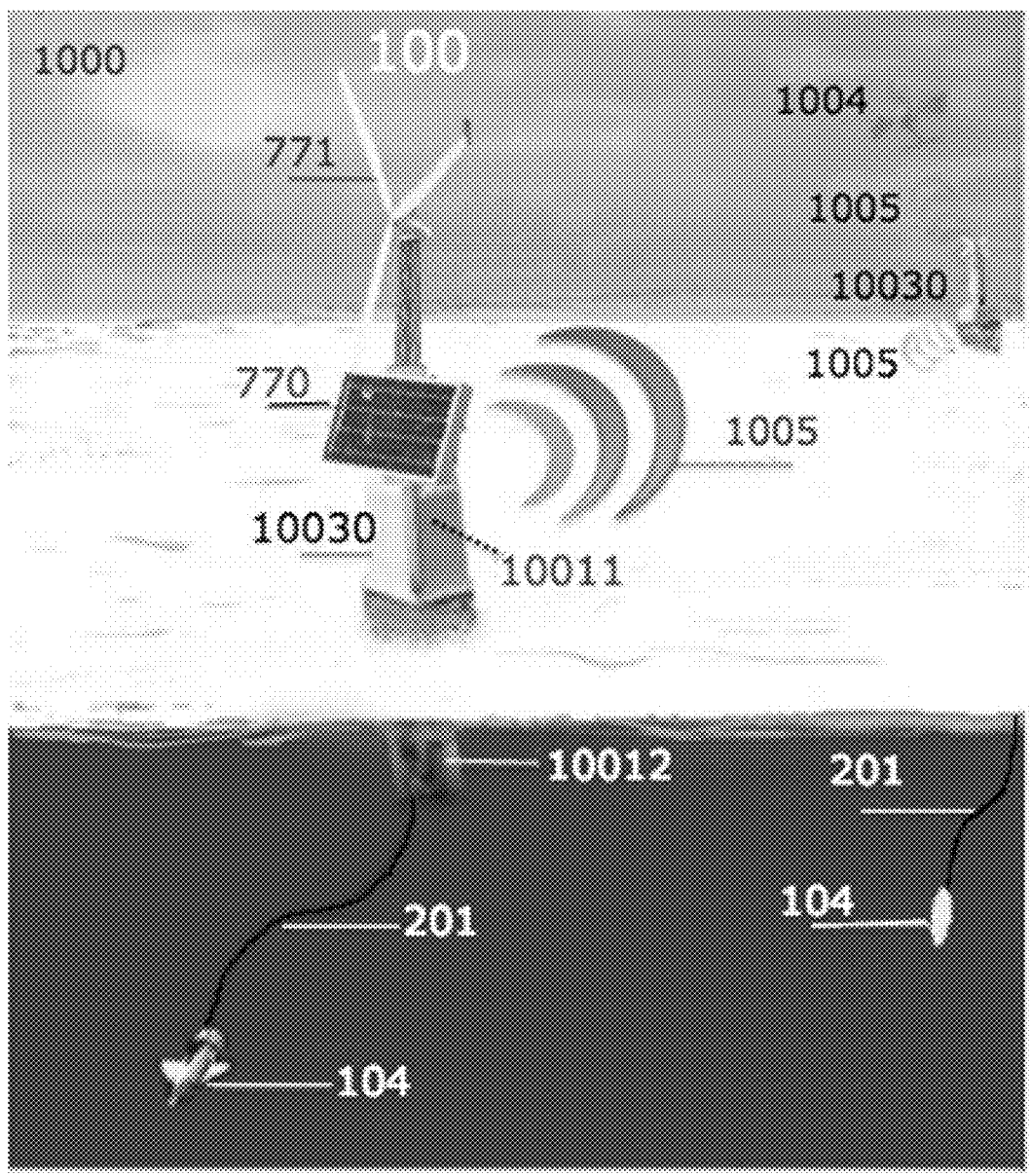
FIG. 16 illustrates an embodiment of a controllable ice piercing buoy with tethered underwater vehicles and energy collecting abilities in use for event detection and communication.
Figure 17:
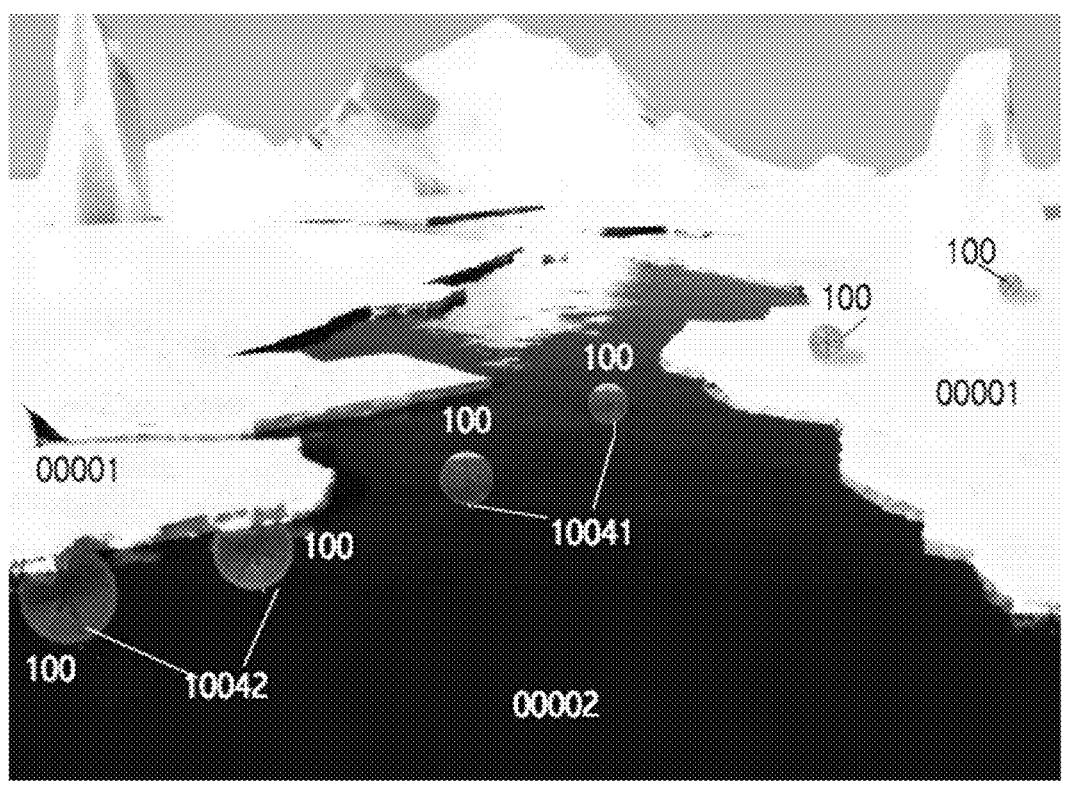
FIG. 17 illustrates an embodiment of a controllable and phase-changing buoy capable of moving on the ice, on the surface of the water, and under the surface of ice.

FIG. 16, shows another example embodiment of the controllable networked buoy system (1000) when the buoys (10030) are stuck into the ice and are not able to get themselves unstuck and move around, as it was the case for the previous example embodiment buoy (10020). The buoys (10030) can penetrate inside the ice by assistance from some personnel or crew, or a robot using various ice-penetrating techniques such as drilling, heating, chemicals. The upper-part (10011) of the buoy can be capable of performing communication (1005) with other buoys (10011) in the networked buoy system (1000) using various RF or laser or optical systems. The lower-part (10012) of the buoy can perform tasks such as positioning, monitoring, and communication (2005) (acoustic, RF, laser, etc.) with other assets under the water. The TUVs (104) connected via a tether (201) to their mother-buoys (10030). The lower-part (10012) of the buoy can be equipped with various sensors and detectors (sonar, infrared, optic, etc.), for example the ones mentioned either in Table 1 or previously suggested in U.S. Pat. No. 8,912,892, to detect ice, detect water, and monitor temperatures and salinity. A smart spooling system as described herein can be integrated inside the upper-part (10011), in order to launch the TUV (104) or retract it based on the information received from the sensors and ice and water detectors, or an external command receives from a satellite (1004) or other buoys (10030) in the area. The buoy (10030) can be equipped with energy harvesting equipment, such as a wind turbine (771) or solar cells (770), for example the ones suggested in Table 1, to generate power for its activities (communication, control, sensing, etc.).

FIG. 16, shows another example embodiment of the controllable buoy (100) which can use its mechanical control systems, such as the ones described at the U.S. Pat. No. 8,912,892 and references [25], [26], and [33], in order to move on the surface of ice (00001), on the surface of the water (00002) and under the surface of the ice (00001). The buoy (10041) on the surface of the water can also use the submergence mechanisms, such as the ones described herein and in the U.S. Pat. No. 8,912,892, to control its movement on the surface of the water (00002). Furthermore, the buoy 10042) can use the submergence and its internal control system in order to sink under the surface of the ice, while its shell would touch the ice from underneath of the ice. The buoy (10042) can use the same mechanical techniques mentioned in the U.S. Pat. No. 8,912,892 to create torque and make the buoy's shell to roll under the surface of the ice. The buoy (10042) can create more positive buoyancy (by getting inflated a bit) in order to facilitate its staying on the surface of the water and under the ice on the surface. Various sensors and electronics, such as sonar, radar, temperature, (for example from Table 1), can be used to survey ice, test for anomaly or chemical species inside the ice and water, or measure the thickness of the ice when positioned under the ice. The buoy (10041) and (10042) could be a number of embodiments of the disclosure have been described. Nevertheless, it is understood that various modifications may be made without departing from the spirit and scope of the present disclosure. Accordingly, other embodiments are within the scope of the following claims.

Figure 18:
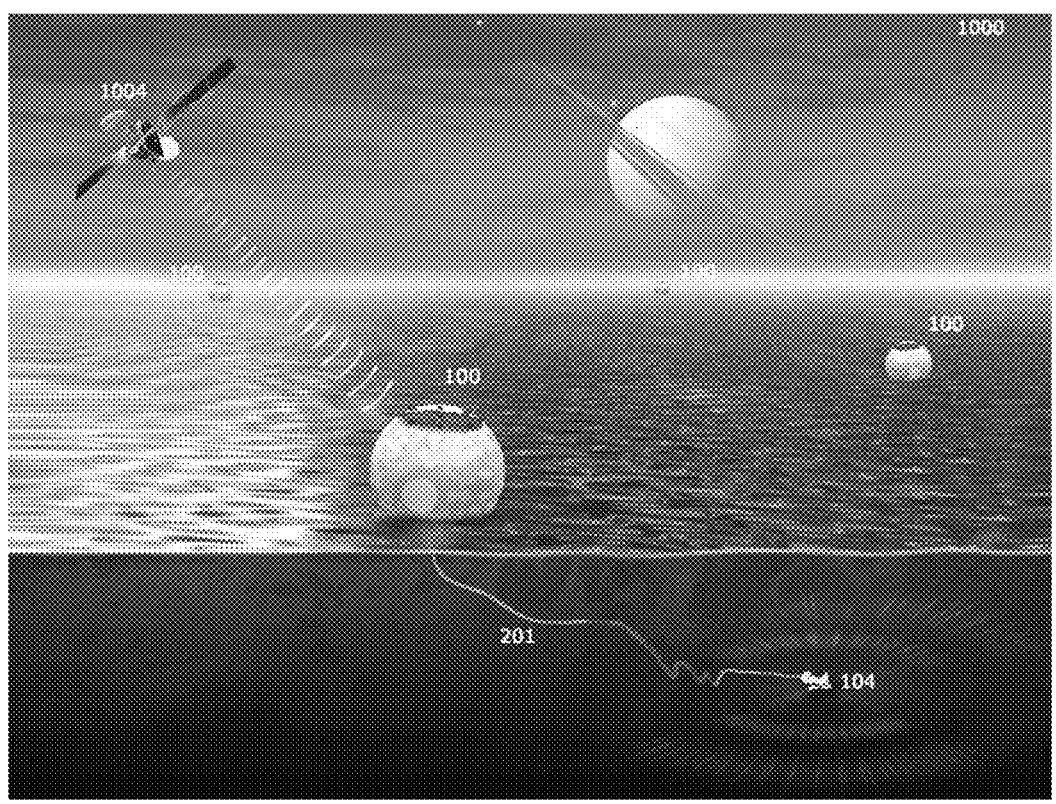
FIG. 18. illustrates an embodiment of a controllable buoy system in a non-terrestrial liquid lake.

FIG. 18, demonstrates and an example embodiment of the controllable networked of buoy systems (1000) in the liquid lakes on the planetary moon, Titan. The spooling-tethered-underwater-vehicle-carrier buoy (100) can be made of materials, electronics, tools, rigidized designs and techniques mentioned in this disclosure or in the U.S. Pat. No. 8,912,892. For example the buoy (100) can be made of ETFE which is chemically, permeability, and abrasion resistant over a temperature range of −300° F. to +300° F. (−185° C. to +150° C.) ETFE (see www.boedeker.com/etfe_p.htm for ETFE specifications). The mother-buoy on the surface (100) can be attached through a wired tethered wire and cords (201) to the TUV (104) which could be a glider, submarine, sounder or other instrument such as radar, sonar, various sensors (including bio-MEMS), and imagers and tools (e.g., the ones mentioned in Table 1) to perform various scientific tests and tasks on or under the surface of the lakes, or at the seafloor of the lakes. The shell of mother-buoy (100) on the surface and also the TUV (104) and their tethers (201), can comprise of various imprinted sensors, and electronic circuits such as antenna, transceivers, batteries, and energy harvesting subsystems, printed on Kapton™ and laminated in ETFE. The mother buoys (100) and its TUV could have wired communication (either optical using fiber optic cables, or RF using copper or silver cables, as explained in this disclosure). This will provide a real-time communication between the TUV (104) and its mother-buoy (100) on the surface and thereby, with the passing by orbiters (1004) when in view. The spooling tethered-underwater-carrier buoys (100) as described here have great advantages over the current exploration concepts suggested for Titan lakes. For example the Titan Mare Explorer (TIME) (see www.nasa.gov/pdf/580675main_02_Ellen_Stofan_TiME_.pdf) or Titan Submarine (TS) concept to discover under the surface of the Titan lakes (see www.nasa.gov/content/titan-submarine-exploring-the-depths-of-kraken/#.VWzDcWRViko). The spooling tethered-under-liquid-vehicle buoy (100) disclosed here could both monitor the surface of the Titan lakes (using the mother-buoy on the surface) and under the surface of the lakes and the seafloor (using its TUVs (104)) at the same time. The disclosed buoy (100) can provide real time communication between the under the surface vehicle TUV (104) and the orbiter. This can have great advantages, as the scientists and technologists on Earth would be able to control the TUV when under the lake in a real time. This is especially important when under the surface vehicle, would witness an important scientific event and the scientists might be interested to have the vehicle stay there for a while and perform further tests and study. Exact positioning and navigation for underwater vehicles, even on the earth and for the known oceans is a very difficult task if not impossible. However, the disclosed buoy (100) and its TUV (104) and the networked buoy (1000), using all the methods mentioned in this disclosure, has reliable positioning for their underwater vehicles (104) and the scientific measurements performs by either the mother-buoy (100) or its TUV (104).

Figure 19:
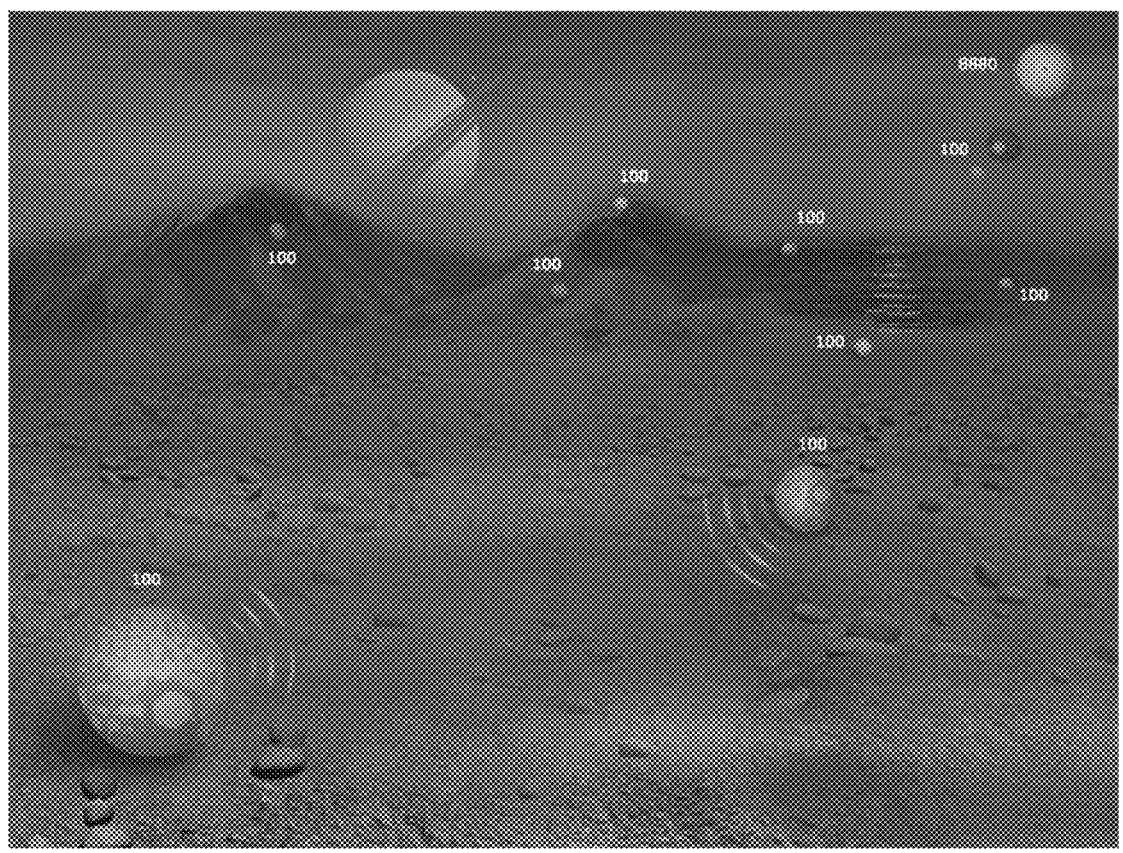
FIG. 19. illustrates an embodiment of a controllable buoy system and its deployment in a non-terrestrial environment.

In FIG. 19, a sample embodiment of a controllable networked-buoys (1000) has been demonstrated while the buoys (100) are getting deployed on Titan, (or any other planetary body such as Europa, comets) using a deployer (8880). The deployer (8880) could be a lander, a parachute, or an aeroshell (similar to ones used for MSL or Philae). The deployer (8880) can carry and deploy several numbers of the controllable buoys (100) and would distribute them over a vast area of the planetary body. The buoys (100) can use the ambient wind or their internal control systems, such as those disclosed herein or in U.S. Pat. No. 8,912,892, in order to move on the hard terrains (mountains, ground, ice etc.). On the other hand, when the buoys (100) drop into the liquid lakes they can function as drifters, using the materials (e.g. ETFE), designs and techniques, as mentioned in this disclosure or in the U.S. Pat. No. 8,912,892. The embodiment buoys (100) which can carry TUVs, are able to launch or release their UTVs (104) in order to discover under the surface of the liquid lakes, where they have dropped (similar to FIG. 18). The example embodiments of the buoy (100) shown in the FIG. 19 can have their sensors, electronics, antenna, imagers, etc. printed or laminated inside its outer layer shell. Similar techniques and material, such as those described herein or in U.S. Pat. No. 8,912,892, could be used to design and manufacture the shell, and to securely integrate the electronics inside the shell. As seen in this disclosure and this picture (FIG. 19), there is an advantage that the buoy (100) has over the TS (the Titan Submarine concept, explained earlier) in that the buoys (100) disclosed herein are able to discover and explore all types of terrains and lakes, such as mountains, sand dunes, lakes, and streams.

Figure 20:
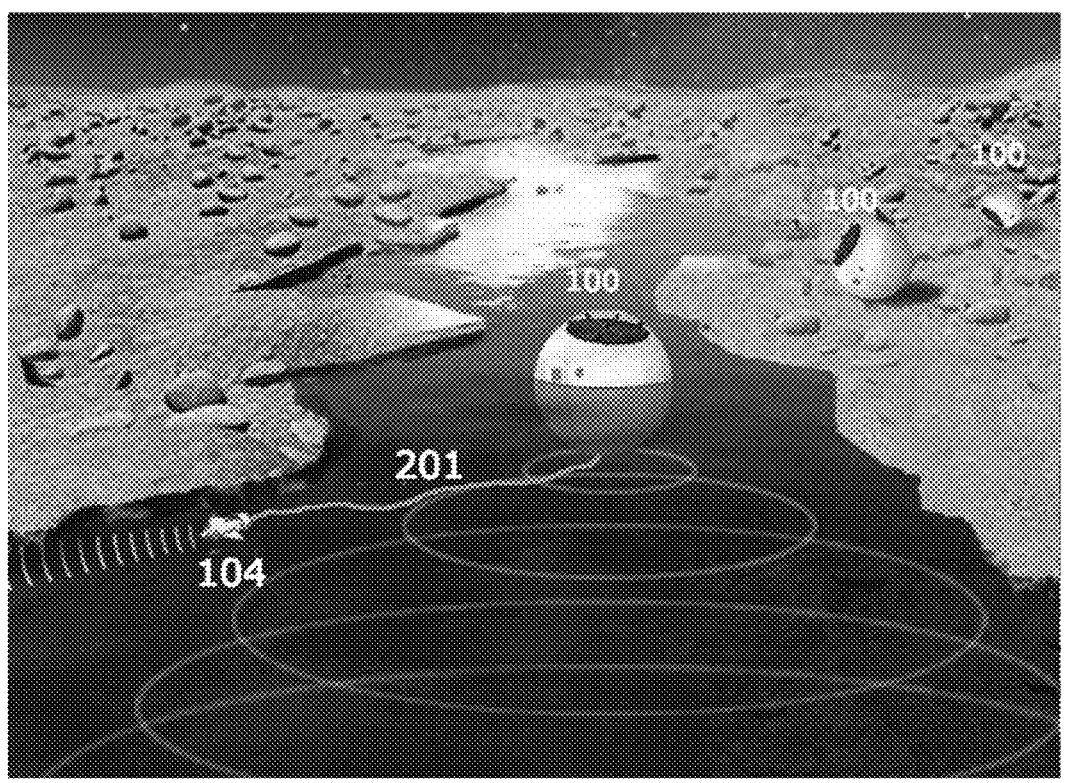
FIG. 20. illustrates an embodiment of a controllable buoy system in a non-terrestrial environment where there is a mix of hard surface and liquid bodies.

FIG. 20 demonstrates that an example embodiment of the controllable buoy (100), which can use its mechanical control system, such as those mentioned herein or in U.S. Pat. No. 8,912,892, to move on the areas comprise of a combination of the hard terrains (such as rocks, sand dunes, or ice sheets) and the liquid (such as puddles, streams or the lakes) on Titan. When the buoy (100) drops in the liquid, it can release its TUV (104) under the surface of the liquid. Both the mother-buoy (100) on the surface and the TUV (104), can use their various sensors imagers, or detectors, (for example some of the ones in Table. 1) to monitor and collect information about the surface and under the surface of the liquid and the ice sheets or the rocks around the lake or the stream. There is an advantage for the buoys disclosed herein over the TS (Titan Submarine) or other drifters suggested for exploring Titan lakes. The buoys (100) disclosed herein are capable of moving from hard surface to a liquid puddle, lake, or stream and vice versa. Moreover, if there are multiple puddles and streams, or lakes in an area, the buoys (100) can explore one lake and then get out of it and move to another liquid lake or area.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The references in the present application, shown in the reference list below, are incorporated herein by reference in their entirety.

LIST OF REFERENCES (ALL INCORPORATED BY REFERENCE HEREIN)

[1] defensetech. org/2009/06/30/submarine-numbers-at-issue/#ixzz2zs3TdeBB

[2] www.noaa.gov/ocean.html

[3] www.cbsnews.com/news/malaysia-airlines-flight-370-25-countries-helping-search-for-missing-plane/[4]

[4] www.google.com/patents/US20030055359

[5] Kenyon, K. E. (1969), Stokes drift for random gravity waves, J. Geophys. Res., 74(28), 6991-6994, doi:10.1029/JC074i028p06991

[6] oceanmotion.org/html/background/ocean-in-motion.htm

[7] Anne H. Clites "Observation of Concurrent Drifting Buoy and Current Meter Measurements In Lake Michigan"; J. Great Lakes Res. 15(2):197-204 www.glerl.noaa.gov/pubs/fulltext/1989/19890001.pdf

[8] M. Burkhardt, F. Davoodi, J. W. Burdick, F. Davoudi, "Harvesting Analysis for Moball, A Self-Propelled Mobile Sensor Platform Capable of Long Duration Operation in Harsh Terrains," (to appear) Proc. IEEE Int. Conf. Robotics and Automation, May-June 2014, Hong Kong.

[9] www2.dupont.com/Teflon_Industrial/en_US/assets/downloads/DuPont_Tefzel_ETFE_Film_Properties_Bulletin_K26943.pdf

[10] ETFE water absorption is almost zero: kmac-plastics.net/data/technical/etfe.htm

[11] M. Stojanovic, "Retrofocusing Techniques for High Rate Acoustic Communications," Journal of the Acoustical Society of America, vol. 117 (3), Pt.1, March 2005, pp. 1173-1185.

[12] M. Stojanovic and L. Freitag, "Multichannel Detection for Wideband Underwater Acoustic CDMA Communications," IEEE Journal of Oceanic Engineering, vol. 31, No. 3, July 2006, pp. 685-695.

[13] H. Ramezani, F. Fazel, M. Stojanovic and G. Leus, "Underwater Acoustic Localization Based on Collision Tolerant Packet Scheduling," submitted to IEEE Trans. Wireless Commun., 2014

[14] M. Stojanovic, J. Catipovic and J. Proakis, "Phase Coherent Digital Communications for Underwater Acoustic Channels," IEEE Journal of Oceanic Engineering, vol. 19, No. 1, January 1994, pp. 100-111

[15] M. Stojanovic, J. Catipovic and J. Proakis, "Adaptive Multichannel Combining and Equalization for Underwater Acoustic Communications," Journal of the Acoustical Society of America, vol. 94~(3), Pt.1, September 1993, pp. 1621-1631.

[16] L. Freitag and M. Stojanovic "Basin-Scale Acoustic Communication: A Feasibility Study Using Tomography M-Sequences," in Proc. IEEE Oceans'01 Conference, Honolulu, Hi., November 2001.

[17] Nesnas, I. A. D.; Matthews, J. B.; Abad-Manterola, J. A.; Burdick, J. W.; Edlund, J. A.; Morrison, J. C.; Peters, R. D.; Tanner, M. M.; Miyake, R. N.; Solish, B. S; 2012, "Axel and DuAxel Rovers for the Sustainable Exploration of Extreme Terrains," J. Field Robotics, vol. 29, no. 4, ppl. 663-685.

[18] Abad-Manterola, P.; Burdick, J. W.; Nesnas, I. A. D.; Cecava, J.; 2009, "Wheel Design and Tension Analysis for the Tethered Axel Rover on Extreme Terrain," Proc. IEEE Aerospace Conf., vols 1-7, pp. 64-71.

[19] Abad-Manterola, P.; Edlund, J.; Burdick, J. W.; Wu, A.; Oliver, T.; Nesnas, I. A. D.; Cecava, J.; 2009, "Axel, A Minimalist Tethered Rover for Exploration of Extreme Planetary Terrains," IEEE Robotics and Automation Magazine, vol. 15, no. 4, pp. 44-52.

[20] Tanner, M. M.; Burdick, J. W.; Nesnas, I. A. D.; "Online Motion Planning For Tethered Robots in Extreme Terrain," Proc. IEEE Int. Conf. Robotics and Automation, pp. 5557-5564.

[21] F. Davoodi et al. "Autonomous and Controllable Systems of Sensors and Methods of Using Such Systems", U.S. patent application Ser. No. 13/776,652, filed on Feb. 22, 2013, issued as U.S. Pat. No. 8,912,892.

[22] Faranak Davoodi "Exploiting Ekman Spiral Phenomena for Locomotion and Controlling the Trajectory and the Speed of the Buoys, AUVs, or Robo Jellies on the Surface and Near the Surface of the Open Seas" Caltech Patent Office CIT File No.: CIT-6531-P-2 Filed: Apr. 24, 2014

[23] U.S. Provisional Application No. 62/006,698 Filed: Jun. 2, 2014

[24] U.S. Provisional Application No. 62/153,322 Filed: Apr. 27, 2015

[25] F. Davoodi, J. Burdick, M. Rais-Zadeh, "A Self-Powered Intelligent Network of Controllable Spherical Sensors to Explore Solar Planets and Moons", AIAA SPACE 2014 Conference and Exposition

[26] F. Davoodi, J. Burdick, Junichi Asama, Alberto Behar, Dimitris Menemenlis, Cyrus Shahabi, Mina Rais-Zadeh, "Moball-Buoy Network: A Near-Real-Time Ground-Truth Distributed Monitoring System to Map Ice, Weather, Chemical Species, and Radiations, in the Arctic"; 11th Annual Polar Technology Conference, March 2015, Denver, Colo. polarpower.org/PTC/2015_pdf/PTC2015_Davoodi.pdf

[27] F. Davoodi, B. Donahue, K. Klaus, B. Acikmese, "Re-Entry Hopper-Aero-Space-Craft System on Mars (REARM-Mars)", AIAA SPACE 2014 Conference and Exposition

[28] Dabiri J O (2005) "On the estimation of swimming and flying forces from wake measurements," *Journal of Experimental Biology* 208 (18): 3519-3532.

[29] Dabiri J O, Colin S P, Costello J H, Gharib M (2005) "Vortex motion in the ocean: in situ visualization of jellyfish swimming and feeding flows," *Physics of Fluids* 17 (9): 091108.

[30] Dabiri J O, Gharib M (2005) "The role of optimal vortex formation in biological fluid transport," *Proceedings of the Royal Society B: Biological Sciences* 272: 1557-1560.

[31] Dabiri J O, Gharib M (2005) "Starting flow through nozzles with temporally variable exit diameter," *Journal of Fluid Mechanics* 538: 111-136.

[32] Dabiri J O, Colin S P, Costello J H, Gharib M (2005) "Flow patterns generated by oblate medusan jellyfish: field measurements and laboratory analyses,"*Journal of Experimental Biology* 208 (7): 1257-1265.

[33] F. Davoodi, F. Davoudi "A Phase-Changing Pendulum to Control Spherical Robots and Buoy Sensors" Tech Brief Journal; Feb. 1, 2015 www.techbriefs.com/component/content/article/1177-moco/techbriefs/21458

[34] Freitag, L.; Grund, M.; Singh, S.; Partan, J.; Koski, P.; Ball, K., "The WHOI micro-modem: an acoustic communications and navigation system for multiple platforms," OCEANS, 2005. Proceedings of MTS/IEEE, vol., no., pp. 1086, 1092 Vol. 2, 17-23 Sep. 2005 doi: 10.1109/OCEANS.2005.1639901

[35] J. Asama, M. Burkhardt, F. Davoodi, J. Burdick "Design Investigation of a Coreless Tubular Linear Generator for a Moball: a Spherical Exploration Robot with Wind-Energy Harvesting Capability" ICRA 2015

[36] www.vtnews.vt.edu/articles/2012/05/052912-engineering-robojelly.html

What is claimed is:

1. A buoy comprising:
a shell;
at least one communication device;
at least one energy-providing device comprising at least one solar cell, magnet configured to move in a solenoid when the buoy moves, or wind turbine;
at least one propulsion control unit; and
an extendible tube or stick comprising a means for penetrating ice, said extendible tube or stick being fully retractable into an inner structure of the shell, said extendible tube or stick being controlled by the propulsion control unit.

2. The buoy of claim 1, wherein the means for penetrating ice comprises a heating element.

3. The buoy of claim 1, wherein the shell is inflatable and comprises a chamber, the chamber configured to contain a fluid, and wherein the chamber comprises a pump to control a volume of the fluid within the chamber, thereby controlling buoyancy, and wherein the buoy further comprises an electronic controller module located in a rigid protective chamber at a center of the inflatable shell, the electronic controller module comprising a processor.

4. The buoy of claim 3, wherein the buoy is configured to deploy at any water depth up to sea floor.

5. The buoy of claim 4, further comprising at least one sensor, wherein the at least one communication device is configured to transmit and receive data from the at least one sensor.

6. The buoy of claim 5, wherein the at least one sensor comprises a camera, a biochemical sensor, a radiation sensor or a pressure sensor.

7. The buoy of claim 3, wherein the buoy is configured to submerge a majority of its shell under the water surface.

8. The buoy of claim 1, wherein the at least one communication device comprises a radio frequency transceiver and an acoustic transceiver.

9. The buoy of claim 1, wherein the at least one energy-providing device further comprises a battery.

10. The buoy of claim 9, wherein the shell is spherical and comprises a transparent dome at its top, and wherein a solar array is located beneath the transparent dome.

11. The buoy of claim 10, wherein the transparent dome comprises a low frequency resonator.

12. The buoy of claim 11, further comprising a hydrophone and an acoustic transceiver.

13. The buoy of claim 9, wherein the energy harvesting device is configured to generate energy from a temperature gradient in water, the temperature gradient being between a temperature at the water surface and a temperature underwater.

14. The buoy of claim 1, wherein the buoy is configured to enter a lower-energy consumption state with reduced activity, and to enter a higher-energy consumption state upon reception of a wake-up signal.

15. The buoy of claim 1, further comprising a propulsion unit controlled by the propulsion control unit, wherein the propulsion unit is an artificial jellyfish propulsion unit.

16. The buoy of claim 1, further comprising a propulsion unit controlled by the propulsion control unit, wherein the propulsion unit comprises a jetting unit and a paddle unit.

17. The buoy of claim 1, wherein the buoy is configured to control its horizontal speed by actively controlling a ratio between an unsubmerged portion of the buoy exposed to wind and a submerged portion of the buoy.

18. A network of buoys comprising a plurality of buoys as in claim 1, the buoys configured to communicate and coordinate among each other.

19. A method to organize a plurality of buoys, the method comprising:
providing a plurality of buoys, each buoy comprising:
a shell;
an extendible tube or stick comprising a means for penetrating ice, said extendible tube or stick being fully retractable into the shell;
at least one sensor;
at least one communication device;
at least one energy-providing device comprising at least one solar cell, magnet configured to move in a solenoid when the buoy moves, or wind turbine;
at least one processor; and
at least one propulsion unit; and
programming the plurality of buoys with a plurality of contingencies and behaviors, said plurality of contingencies and behaviors including using the extendible tube or stick to control the horizontal movement of said each buoy.

20. The method of claim 19, wherein the plurality of contingencies further comprise at least one of: detecting a vehicle entering a designated area, detecting a communication signal within the designated area, detecting a natural event within the designated area, taking a measurement within the designated area, and receiving an assignment to deploy within the designated area for surveillance.

21. The method of claim 20, wherein the designated area is on a non-terrestrial body.

22. The method of claim 21, wherein the non-terrestrial body is Titan.

23. The method of claim 19, wherein the plurality of behaviors comprise assigning a location to each buoy of the plurality of buoys, coordinating signal emissions from a subset of buoys of the plurality of buoys thereby enabling beam forming, deploying a subset of buoys at a specific water depth, or triangulating a position of an object.

24. The method of claim 19, further comprising:
deploying, at a water depth under a thermocline level, a first subset of buoys of the plurality of buoys; and
sending communication signals between the first subset of buoys under the thermocline level.

25. The method of claim 24, further comprising:
transmitting the communication signals from the first subset of buoys to a second subset of buoys of the plurality of buoys.

26. The method of claim 19, further comprising:
detecting or calculating an Ekman spiral of velocity vectors underwater; and
determining a specified water depth based on the detected or calculated Ekman spiral, the specified water depth having a velocity in a desired direction different from a wind velocity at the water top surface; and
submerging at least a subset of the plurality buoys to the specified water depth.

27. The method of claim 19, wherein the plurality of behaviors includes triangulating a position of a buoy, a tethered vehicle, an underwater industrial asset, or a vehicle.

28. The method of claim 19, further comprising:
providing a subset of buoys each with at least one chamber containing at least one biochemical compound;
detecting an industrial pollution accident; and
cleaning a designated area at different depths, with the at least one biochemical compound, by deploying each buoy at the different water depths.

* * * * *